United States Patent
Yamaguchi et al.

(10) Patent No.: US 10,324,374 B2
(45) Date of Patent: *Jun. 18, 2019

(54) ACTIVE LIGHT SENSITIVE OR RADIATION SENSITIVE RESIN COMPOSITION, ACTIVE LIGHT SENSITIVE OR RADIATION SENSITIVE FILM, MASK BLANK PROVIDED WITH ACTIVE LIGHT SENSITIVE OR RADIATION SENSITIVE FILM, PATTERN FORMING METHOD, METHOD FOR MANUFACTURING ELECTRONIC DEVICE, ELECTRONIC DEVICE AND NOVEL COMPOUND

(71) Applicant: FUJIFILM Corporation, Tokyo (JP)

(72) Inventors: Shuhei Yamaguchi, Shizuoka (JP); Tomotaka Tsuchimura, Shizuoka (JP); Natsumi Yokokawa, Shizuoka (JP); Koutarou Takahashi, Shizuoka (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/080,714

(22) Filed: Mar. 25, 2016

(65) Prior Publication Data

US 2016/0209746 A1 Jul. 21, 2016

Related U.S. Application Data

(63) Continuation of application No. PCT/JP2014/075682, filed on Sep. 26, 2014.

(30) Foreign Application Priority Data

Sep. 30, 2013 (JP) .................................. 2013-205970

(51) Int. Cl.
| | | |
|---|---|---|
| G03F 7/038 | (2006.01) |
| C07C 233/36 | (2006.01) |
| C07C 271/16 | (2006.01) |
| C07C 271/24 | (2006.01) |
| C07C 271/34 | (2006.01) |
| C07C 275/10 | (2006.01) |
| C07C 275/24 | (2006.01) |
| C07C 275/26 | (2006.01) |
| C07C 323/60 | (2006.01) |
| C07D 211/26 | (2006.01) |
| C07D 233/32 | (2006.01) |
| C07D 233/36 | (2006.01) |
| C07D 235/26 | (2006.01) |
| C07D 239/10 | (2006.01) |
| C07D 251/30 | (2006.01) |
| C07D 403/12 | (2006.01) |
| C07D 487/04 | (2006.01) |

(52) U.S. Cl.
CPC ............ *G03F 7/038* (2013.01); *C07C 233/36* (2013.01); *C07C 271/16* (2013.01); *C07C 271/24* (2013.01); *C07C 271/34* (2013.01); *C07C 275/10* (2013.01); *C07C 275/24* (2013.01); *C07C 275/26* (2013.01); *C07C 323/60* (2013.01); *C07D 211/26* (2013.01); *C07D 233/32* (2013.01); *C07D 233/36* (2013.01); *C07D 235/26* (2013.01); *C07D 239/10* (2013.01); *C07D 251/30* (2013.01); *C07D 403/12* (2013.01); *C07D 487/04* (2013.01); *G03F 7/0382* (2013.01); *G03F 7/0387* (2013.01); *C07C 2601/14* (2017.05)

(58) Field of Classification Search
CPC ............................... G03F 7/038; G03F 7/0382
See application file for complete search history.

(56) References Cited

U.S. PATENT DOCUMENTS

| | | | |
|---|---|---|---|
| 3,246,002 A | | 4/1966 | Gagliardi et al. |
| 3,773,056 A | * | 11/1973 | Kalopissis ............... A61K 8/42 132/209 |
| 8,470,512 B2 | | 6/2013 | Masunaga et al. |

(Continued)

FOREIGN PATENT DOCUMENTS

| | | |
|---|---|---|
| CN | 102516453 A | 6/2012 |
| EP | 0 613 050 A2 | 8/1994 |

(Continued)

OTHER PUBLICATIONS

English translation of JP, 2006-208607, A (2006) from machine translation from AIPN Japan Patent Office National center for Industrial Property Information and Training, generated Sep. 16, 2017, 79 pages.*

English translation of JP, 2006-091765, A (2006) from machine translation from AIPN Japan Patent Office National center for Industrial Property Information and Training, generated Sep. 16, 2017, 54 pages.*

H. Röschert et al., "DN 21, DN 41: Negative Tone Photoresists for Deep-UV Lithography", SPIE Advances in Resist Technology and Processing IX, 1992, pp. 157-171, vol. 1672.

(Continued)

*Primary Examiner* — Cynthia Hamilton

(74) *Attorney, Agent, or Firm* — Sughrue Mion, PLLC

(57) ABSTRACT

There is provided an active light sensitive or radiation sensitive resin composition which contains (A) an alkali soluble resin and (C) a cross-linking agent represented by the following General Formula (1-0).

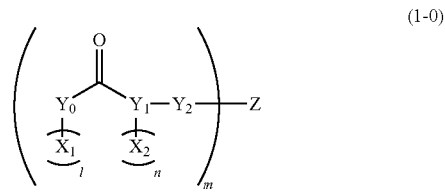

(1-0)

22 Claims, 4 Drawing Sheets

(56) References Cited

U.S. PATENT DOCUMENTS

| | | | |
|---|---|---|---|
| 2005/0215761 A1* | 9/2005 | Codignola | C07C 235/74 528/392 |
| 2010/0183978 A1* | 7/2010 | Yoshidome | G03F 7/405 430/270.1 |
| 2012/0028190 A1 | 2/2012 | Masunaga et al. | |
| 2013/0084518 A1* | 4/2013 | Tsuchimura | G03F 1/76 430/5 |
| 2016/0282720 A1* | 9/2016 | Takahashi | G03F 7/0382 |

FOREIGN PATENT DOCUMENTS

| | | | |
|---|---|---|---|
| EP | 3 106 920 A1 * | 12/2016 | |
| JP | 1-293339 A | 11/1989 | |
| JP | 6-301200 A | 10/1994 | |
| JP | 2002-6500 A | 1/2002 | |
| JP | 2006-91765 A | 4/2006 | |
| JP | 2006-208607 A | 8/2006 | |
| JP | 2008-268935 A | 11/2008 | |
| JP | 2012-46731 A | 3/2012 | |
| KR | 1020120023533 A | 3/2012 | |
| WO | WO 2015/118774 A1 * | 8/2016 | |

OTHER PUBLICATIONS

Qinghuang Lin et al., "Effects of Crosslinking Agent on Lithographic Performance of Negative-Tone Resists Based on Poly(p-hydroxystyrene)", SPIE, 1997, pp. 974-987, vol. 3049.

International Search Report for PCT/JP2014/075682 dated Dec. 22, 2014.

International Preliminary Report on Patentability dated Apr. 14, 2016, issued in counterpart application No. PCT/JP2014/075682.

Communication dated Mar. 14, 2017, from the Korean Intellectual Property Office in counterpart Korean application No. 10-2016-7008254.

Communication dated Aug. 30, 2016, from the Japanese Patent Office in counterpart application No. 2013-205970.

Communication dated Oct. 30, 2017 from the Korean Intellectual Property Office in counterpart application No. 10-2016-7008254.

Communication dated Oct. 31, 2017 from the Taiwanese Intellectual Property Office in counterpart application No. 103133727.

Communication dated Mar. 21, 2019 from the State Intellectual Property Office of the P.R.C. in counterpart Chinese Application No. 201480053035.X.

* cited by examiner

# ACTIVE LIGHT SENSITIVE OR RADIATION SENSITIVE RESIN COMPOSITION, ACTIVE LIGHT SENSITIVE OR RADIATION SENSITIVE FILM, MASK BLANK PROVIDED WITH ACTIVE LIGHT SENSITIVE OR RADIATION SENSITIVE FILM, PATTERN FORMING METHOD, METHOD FOR MANUFACTURING ELECTRONIC DEVICE, ELECTRONIC DEVICE AND NOVEL COMPOUND

CROSS-REFERENCE TO RELATED APPLICATIONS

This application is a Continuation application of PCT Application No. PCT/JP2014/075682, filed Sep. 26, 2014, and based upon and claiming the benefit of priority from Japanese Patent Application No. 2013-205970, filed Sep. 30, 2013, the entire contents of all of which are incorporated herein by reference.

BACKGROUND OF THE INVENTION

1. Field of the Invention

The present invention relates to an active light sensitive or radiation sensitive resin composition that is suitably used for a production process of VLSIs and high-capacity microchips, a fabrication process of molds for nanoimprint, an ultramicrolithography process applicable for a production process of high-density information recording media, and other photofabrication processes, an active light sensitive or radiation sensitive film, a mask blank provided with the active light sensitive or radiation sensitive film, a pattern forming method, a method for manufacturing an electronic device, an electronic device, and a novel compound. More specifically, the present invention relates to an active light sensitive or radiation sensitive resin composition that can be suitably used for microfabrication of semiconductor elements using an electron beam, X-rays, or EUV light, an active light sensitive or radiation sensitive film, a mask blank provided with the active light sensitive or radiation sensitive film, a pattern forming method, a method for manufacturing an electronic device, an electronic device, and a novel compound.

2. Description of the Related Art

In the microfabrication using a resist composition, ultra fine patterns are required to be formed since integrated circuits are increasingly highly integrated. Consequently, exposure wavelengths also tend to be shortened from g-line and i-line to a KrF laser and an ArF laser, and, in recent years, lithography techniques that use an electron beam, X-rays, or EUV light instead of excimer laser light are under development.

However, from the viewpoint of total performance as a resist, it is extremely difficult to find a suitable combination of a resin, a photoacid generator, a basic compound, an additive, and a solvent, used, and, in particular, in view of recent demand for forming an ultra fine (for example, a line width of 50 nm or less) pattern with high performance, the current situation cannot yet be said to be sufficient.

In electron beam (EB) lithography, it is known that the influence of electron scattering, that is, the influence of forward scattering in a resist film is diminished by increasing an accelerating voltage of an EB. Consequently, in recent years, the accelerating voltage of the EB has tended to increase. However, if the accelerating voltage of the EB is increased, while the influence of forward scattering is diminished, the influence of the scattering of electrons reflected in a resist substrate, that is, the influence of backward scattering is increased. The influence of backward scattering is particularly great when an isolated line pattern having a large exposure area is formed. Accordingly, for example, if the accelerating voltage of the EB is increased, resolution of the isolated line pattern is likely to deteriorate.

Particularly, in a case of forming patterns in photomask blanks used for semiconductor exposure, the lower layer of a resist film includes a light shielding film that contains heavy atoms such as chromium, molybdenum, and tantalum. In this case, the influence of backward scattering caused by reflection from the lower layer of a resist is more marked compared to a case of applying a resist onto a silicon wafer. Consequently, in a case where the isolated line pattern is formed on the photomask blanks, there is a possibility that the pattern will be easily influenced particularly by the backward scattering and that the resolution will deteriorate. On the other hand, in EUV (Extreme Ultra Violet) lithography, due to the surface topology of a reflecting mirror configuring the optical system of an exposure device or flare light generated by a phase difference, and unintended light (Out of Band light: OoB light) of a wavelength different from EUV light, which is generated since the reflecting mirror shows a certain degree of reflection characteristics for even light of a wavelength different from the exposure wavelength (typically, 13.5 nm) of the EUV light, decrease in resolution is likely to be caused.

With miniaturization of a pattern to be formed, a problem that a pattern collapses is newly generated, and thus, to prevent this problem, thinning of a resist film also has been studied. However, due to the influence of swelling of a resist film at the time of development, elimination of the pattern collapse is not sufficient. In contrast, it is reported that, in a case where N-methylol melamine, N-methylol glycoluril, or the like is used as a cross-linking agent, cross-linking is formed while the hydroxyl group in the resist film is eliminated (SPIE Vol. 1672 (1992) 157 and SPIE Vol. 3049 (1997) 974). These cross-linking agents are discussed in JP1989-293339A (JP-H01-293339A), JP1994-301200A (JP-H06-301200A), and the like, and by using these cross-linking agents, the effect in which resolution is improved to some extent is obtained, but, in a resist film thinned for forming a fine pattern, it is not possible to obtain satisfactory results.

Microfabrication using a resist composition is not only directly used for producing integrated circuits but also has been applied for fabricating a so-called mold structure for imprint in recent years (for example, refer to JP2008-268935A, JP2002-6500A, and SPIE Vol. 1672 (1992) 157). Accordingly, even in a case where an ultra fine (for example, a line width of 50 nm or less) pattern is formed by using X-rays, soft X-rays, or an electron beam as an exposure light source, it is important to satisfy high resolution and resist performance such as roughness characteristics at the same time, and thus, there is a problem that needs to be solved.

SUMMARY OF THE INVENTION

An object of the present invention is to provide an active light sensitive or radiation sensitive resin composition of which a pattern which satisfies high resolving power, an excellent pattern shape, and low line edge roughness (LER) can be formed, an active light sensitive or radiation sensitive film using this composition, a mask blank having this film, and a pattern forming method.

An object of the present invention is to provide an active light sensitive or radiation sensitive resin composition which exhibits high resolving power, in particular, in formation of an ultra fine (for example, a line width of 50 nm or less) pattern by exposure using an electron beam or extreme ultraviolet rays, an active light sensitive or radiation sensitive film using this composition, a mask blank having this film, and a pattern forming method.

In addition, another object of the present invention is to provide a method for manufacturing an electronic device including the pattern forming method and an electronic device.

An embodiment of the present invention is as follows.

[1] An active light sensitive or radiation sensitive resin composition, containing (A) an alkali soluble resin and (C) a cross-linking agent represented by the following General Formula (1-0).

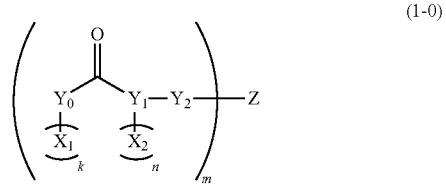

(1-0)

In the formula, each of $X_1$ and $X_2$ independently represents a hydrogen atom, an alkyl group, a hydroxymethyl group, or an alkoxymethyl group.

Each of $Y_0$ and $Y_1$ independently represents a carbon atom, a nitrogen atom, or an oxygen atom.

At least one of k $X_1$'s and n $X_2$'s is a hydroxymethyl group or an alkoxymethyl group, and at least one of $Y_0$ and $Y_1$ is a nitrogen atom substituted with the hydroxymethyl group or the alkoxymethyl group.

$Y_2$ represents a single bond or an alkylene group.

Z represents an m valent connecting group.

k is 3 when $Y_0$ is a carbon atom, is 2 when $Y_0$ is a nitrogen atom, and is 1 when $Y_0$ is an oxygen atom.

When $Y_1$ is a carbon atom, n is 2, when $Y_1$ is a nitrogen atom, n is 1, and when $Y_1$ is an oxygen atom, n is 0.

m represents an integer of 2 to 6.

Two of $X_1$, $X_2$, and $Y_2$ may be bonded to each other to form a ring.

[2] The active light sensitive or radiation sensitive resin composition according to [1], in which the cross-linking agent (C) is represented by the following General Formula (1).

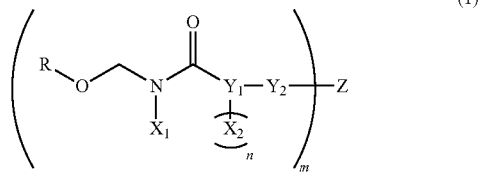

(1)

In the formula, R represents a hydrogen atom or an alkyl group.

Each of $X_1$ and $X_2$ independently represents a hydrogen atom, an alkyl group, a hydroxymethyl group, or an alkoxymethyl group.

$Y_1$ represents a carbon atom, a nitrogen atom, or an oxygen atom.

$Y_2$ represents a single bond or an alkylene group.

Z represents an m valent connecting group.

n is 2 when $Y_1$ is a carbon atom, is 1 when $Y_1$ is a nitrogen atom, and is 0 when $Y_1$ is an oxygen atom.

m represents an integer of 2 to 6.

Two of $X_1$, $X_2$, and $Y_2$ may be bonded to each other to form a ring.

[3] The active light sensitive or radiation sensitive resin composition according to [1] or [2], further containing a compound (B) that generates an acid by irradiation with active light or radiation.

[4] The active light sensitive or radiation sensitive resin composition according to [3], in which the compound (B) that generates an acid by irradiation with active light or radiation is a sulfonium salt.

[5] The active light sensitive or radiation sensitive resin composition according to any one of [1] to [4], in which the molecular weight of the cross-linking agent (C) is 450 or greater.

[6] The active light sensitive or radiation sensitive resin composition according to any one of [1] to [5], in which, in General Formula (1-0) or (1), Z is represented by the following General Formula (2).

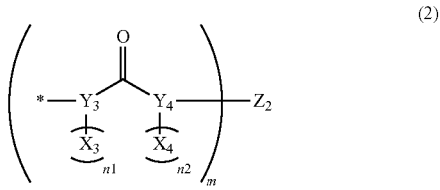

(2)

In the formula, each of $Y_3$ and $Y_4$ independently represents a single bond, a carbon atom, a nitrogen atom, or an oxygen atom.

Each of $X_3$ and $X_4$ independently represents a hydrogen atom or an alkyl group.

When $Y_3$ and $Y_4$ are single bonds or oxygen atoms, each of n1 and n2 is 0, when $Y_3$ and $Y_4$ are nitrogen atoms, each of n1 and n2 is 1, and when $Y_3$ and $Y_4$ are carbon atoms, each of n1 and n2 is 2.

$Z_2$ represents a chain or cyclic saturated hydrocarbon group, an aromatic hydrocarbon group, or a group obtained by combining two or more types thereof.

m represents an integer of 2 to 6, and corresponds to m in General Formula (1).

* represents a linking site with $Y_2$ in General Formula (1-0) or (1).

[7] An active light sensitive or radiation sensitive film which is formed of the active light sensitive or radiation sensitive resin composition according to any one of [1] to [6].

[8] A mask blank provided with the active light sensitive or radiation sensitive film according to [7].

[9] A pattern forming method, including a step of forming a film by applying the active light sensitive or radiation sensitive resin composition according to any one of [1] to [6] to a substrate, a step of exposing the film, and a step of forming a negative-type pattern by developing the exposed film.

[10] A method for manufacturing an electronic device, including the pattern forming method according to [9].

[11] An electronic device manufactured by the method for manufacturing an electronic device according to [10].

[12] A compound represented by General Formula (1).

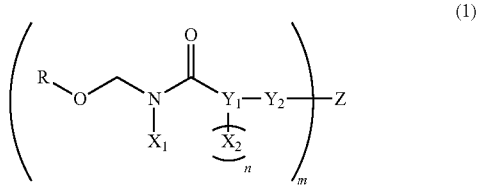

In the formula, R represents a hydrogen atom or an alkyl group.

Each of $X_1$ and $X_2$ independently represents a hydrogen atom, an alkyl group, a hydroxymethyl group, or an alkoxymethyl group.

$Y_1$ represents a carbon atom, a nitrogen atom, or an oxygen atom.

$Y_2$ represents a single bond or an alkylene group.

Z represents an m valent connecting group.

n is 2 when $Y_1$ is a carbon atom, is 1 when $Y_1$ is a nitrogen atom, and is 0 when $Y_1$ is an oxygen atom.

m represents an integer of 2 to 6.

Two of $X_1$, $X_2$, and $Y_2$ may be bonded to each other to form a ring.

[13] The compound according to [12], in which at least one $Y_1$ in General Formula (1) is a nitrogen atom.

[14] The compound according to [12] or [13], in which, in General Formula (1), Z is represented by the following General Formula (2).

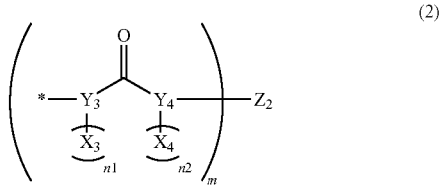

In the formula, each of $Y_3$ and $Y_4$ independently represents a single bond, a carbon atom, a nitrogen atom, or an oxygen atom.

Each of $X_3$ and $X_4$ independently represents a hydrogen atom or an alkyl group.

When $Y_3$ and $Y_4$ are single bonds or oxygen atoms, each of n1 and n2 is 0, when $Y_3$ and $Y_4$ are nitrogen atoms, each of n1 and n2 is 1, and when $Y_3$ and $Y_4$ are carbon atoms, each of n1 and n2 is 2.

$Z_2$ represents a chain or cyclic saturated hydrocarbon group, an aromatic hydrocarbon group, or a group obtained by combining two or more types thereof.

m represents an integer of 2 to 6, and corresponds to m in General Formula (1).

* represents a linking site with $Y_2$ in General Formula (1-0) or (1).

By the present invention, it is possible to provide an active light sensitive or radiation sensitive resin composition of which a pattern which satisfies high resolving power, an excellent pattern shape, and low line edge roughness (LER) can be formed, an active light sensitive or radiation sensitive film using this composition, a mask blank having this film, and a pattern forming method. According to the present invention, it is possible to suppress reduction in resolution even in a case where an ultra fine (for example, a line width of 50 nm or less) pattern is formed by exposure using an electron beam or extreme ultraviolet rays.

DESCRIPTION OF THE PREFERRED EMBODIMENTS

Figure 1:
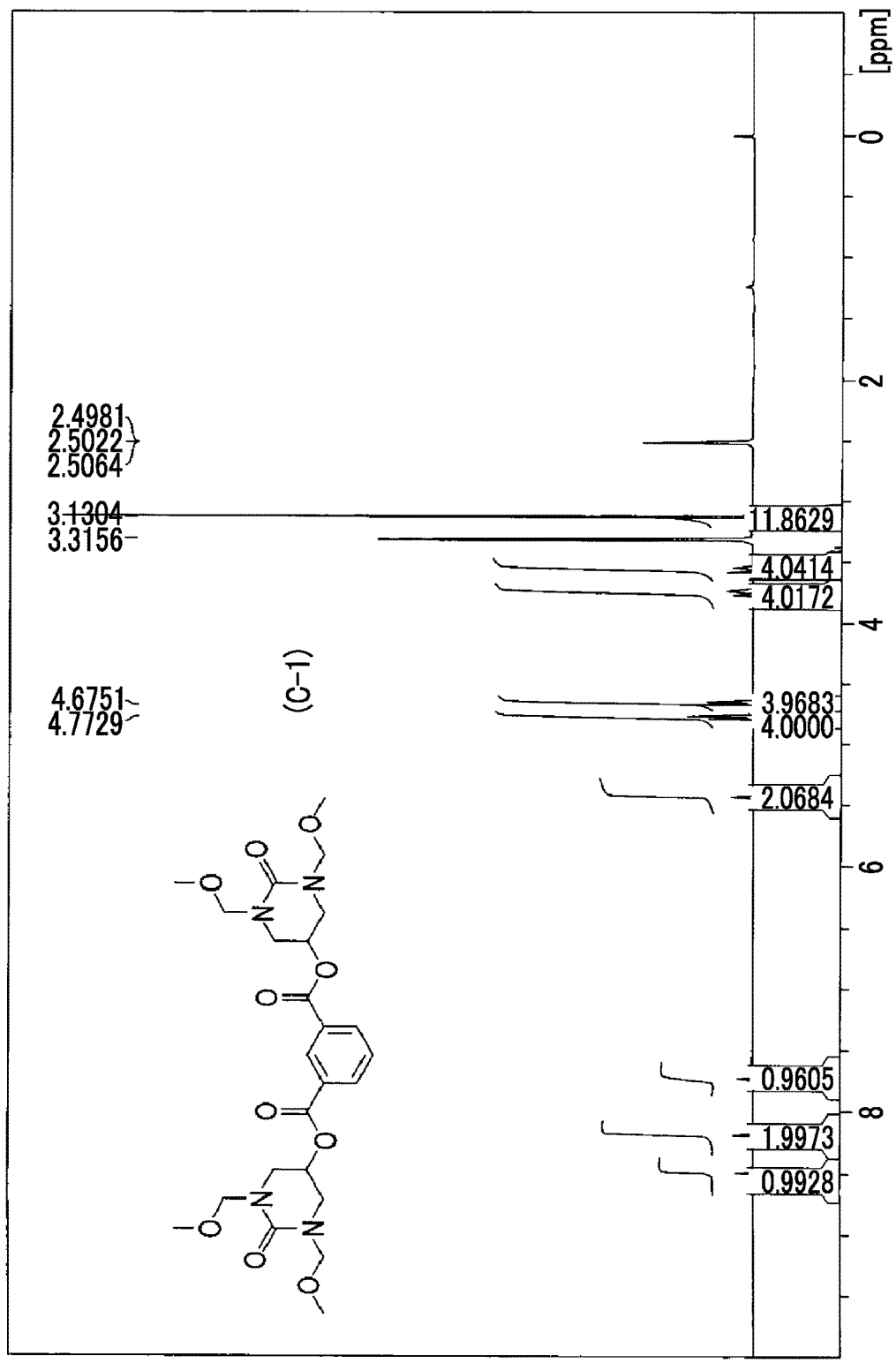
FIG. 1 is a view showing an NMR chart (DMSO-d6) of a compound (C-1) synthesized in the example.

Regarding the description of a group (atomic group) in the present specification, when the description does not indicate whether a group is substituted or unsubstituted, the description includes both a group having a substituent and a group not having a substituent. For example, "alkyl group" includes not only an alkyl group (an unsubstituted alkyl group) which does not have a substituent but also an alkyl group (a substituted alkyl group) which has a substituent.

Moreover, the term "active light" or "radiation" described here refers to, for example, a bright line spectrum of a mercury lamp, far-ultraviolet rays represented by an excimer laser, extreme ultraviolet rays (EUV light), X-rays, an electron beam (EB), or the like. In addition, the light in the present invention refers to the active light or the radiation.

In addition, the term "exposure" described here includes not only the exposure performed using a mercury lamp, far-ultraviolet rays represented by an excimer laser, extreme ultraviolet rays (EUV light), or X-rays, but also drawing performed using a particle beam such as an electron beam, an ion beam, or the like, unless otherwise specified.

Hereinafter, embodiments of the present invention will be described in detail.

<Cross-Linking Agent (C)>

The active light sensitive or radiation sensitive resin composition of the present invention contains a cross-linking agent (C) represented by General Formula (1-0). As a result of intensive studies, the present inventors found that, in a case where N-methylol melamine, N-methylol glycoluril, or the like disclosed in JP1989-293339A (JP-H01-293339A) or JP1994-301200A (JP-H06-301200A) is used as a cross-linking agent, since the compound has a low molecular weight, and due to this, the compound is volatilized from a film at the time of drying after film formation or at the time of post exposure bake, it is not possible to obtain the desired resolution, pattern shape, and roughness characteristics in an ultra fine region. In contrast, in a case where the cross-linking agent (C) represented by General Formula (1-0) (hereinafter, simply referred to as "cross-linking agent (C)") is used, it is possible to obtain the desired resolution, pattern shape, and roughness characteristics, while suppressing swelling even in a resist film thinned to form a fine pattern.

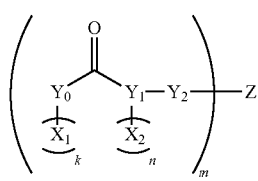

(1-0)

In the formula, each of $X_1$ and $X_2$ independently represents a hydrogen atom, an alkyl group, a hydroxymethyl group, or an alkoxymethyl group.

Each of $Y_0$ and $Y_1$ independently represents a carbon atom, a nitrogen atom, or an oxygen atom.

At least one of l $X_1$'s and n $X_2$'s is a hydroxymethyl group or an alkoxymethyl group, and at least one of $Y_0$ and $Y_1$ is a nitrogen atom substituted with the hydroxymethyl group or the alkoxymethyl group.

$Y_2$ represents a single bond or an alkylene group.

Z represents an m valent connecting group.

k is 3 when $Y_0$ is a carbon atom, is 2 when $Y_0$ is a nitrogen atom, and is 1 when $Y_0$ is an oxygen atom.

n is 2 when $Y_1$ is a carbon atom, is 1 when $Y_1$ is a nitrogen atom, and is 0 when $Y_1$ is an oxygen atom.

m represents an integer of 2 to 6.

Two of $X_1$, $X_2$, and $Y_2$ may be bonded to each other to form a ring.

The alkyl group represented by $X_1$ or $X_2$ in General Formula (1-0) may be a chain alkyl group or a cycloalkyl group, and is preferably an alkyl group having 1 to 30 carbon atoms or a cycloalkyl group having 3 to 30 carbon atoms. Specific examples thereof include a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group, and a bornyl group.

The alkyl group represented by $X_1$ or $X_2$ may have a substituent.

The alkyl portion of the alkoxy group in the alkoxymethyl group represented by $X_1$ or $X_2$ may be a chain alkyl group or a cycloalkyl group, and examples thereof include the same as the specific examples of the alkyl group represented by $X_1$ or $X_2$ described above. As the alkoxy group in the alkoxymethyl group, a methoxy group or an ethoxy group is more preferable, and a methoxy group is particularly preferable.

The alkylene group represented by $Y_2$ may be a chain alkylene group or a cycloalkylene group. The chain alkylene group preferably has 1 to 10 carbon atoms, and more preferably has 1 to 5 carbon atoms, and examples thereof include a methylene group, an ethylene group, and a propylene group. The cycloalkylene group is preferably a cycloalkylene group having 3 to 20 carbon atoms, and examples thereof include a cyclohexylene group, a cyclopentylene group, a norbornylene group, and an adamantylene group.

Examples of the connecting group represented by Z include a linear or branched alkylene group, a cycloalkylene group, an arylene group, an ether bond, a thioether bond, an ester bond, an amide bond, a urethane bond, a urea bond, and a group obtained by combining two or more types thereof in a case where Z is a divalent connecting group (m=2). In a case where Z is a tri- or higher valent connecting group (m≥3), tri- or higher valent connecting group corresponding to these specific examples is exemplified.

In one aspect of the present invention, Z is preferably a structure represented by the following General Formula (2).

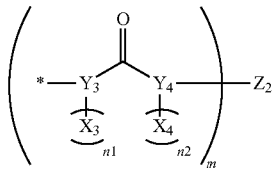

(2)

In the formula, each of $Y_3$ and $Y_4$ independently represents a single bond, a carbon atom, a nitrogen atom, or an oxygen atom.

Each of $X_3$ and $X_4$ independently represents a hydrogen atom or an alkyl group.

When $Y_3$ and $Y_4$ are single bonds or oxygen atoms, each of n1 and n2 is 0, when $Y_3$ and $Y_4$ are nitrogen atoms, each of n1 and n2 is 1, and when $Y_3$ and $Y_4$ are carbon atoms, each of n1 and n2 is 2.

$Z_2$ represents a chain or cyclic saturated hydrocarbon group, an aromatic hydrocarbon group, or a group obtained by combining two or more types thereof.

m represents an integer of 2 to 6, and corresponds to m in General Formula (1).

* represents a linking site with $Y_2$ in General Formula (1-0) or (1).

Examples of the alkyl group represented by $X_3$ or $X_4$ include a methyl group, an ethyl group, a propyl group, an n-butyl group, a sec-butyl group, a hexyl group, an octyl group, a cyclopropyl group, a cyclobutyl group, a cyclopentyl group, a cyclohexyl group, a cyclooctyl group, an adamantyl group, a norbornyl group, an isobornyl group, a camphanyl group, a dicyclopentyl group, an α-pinel group, a tricyclodecanyl group, a tetracyclododecyl group, and an androstanyl group.

Examples of the chain or cyclic saturated hydrocarbon group represented by $Z_2$ include a methyl group, an ethyl group, a propyl group, an n-butyl group, a sec-butyl group, a hexyl group, an octyl group, a cyclopropyl group, a cyclobutyl group, a cyclopentyl group, a cyclohexyl group, a cyclooctyl group, an adamantyl group, a norbornyl group, an isobornyl group, a camphanyl group, a dicyclopentyl group, an α-pinel group, a tricyclodecanyl group, a tetracyclododecyl group, and an androstanyl group.

In addition, examples of the aromatic hydrocarbon group represented by $Z_2$ include a phenyl group, a naphthyl group, a phenanthryl group, and an anthryl group.

In one aspect of the present invention, the cross-linking agent (C) is preferably represented by General Formula (1).

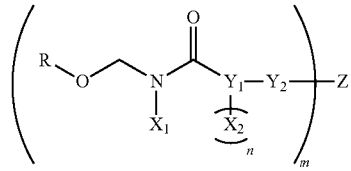

(1)

In the formula, R represents a hydrogen atom or an alkyl group.

Each of $X_1$ and $X_2$ independently represents a hydrogen atom, an alkyl group, a hydroxymethyl group, or an alkoxymethyl group.

$Y_1$ represents a carbon atom, a nitrogen atom, or an oxygen atom.

$Y_2$ represents a single bond or an alkylene group.

Z represents an m valent connecting group.

n is 2 when $Y_1$ is a carbon atom, is 1 when $Y_1$ is a nitrogen atom, and is 0 when $Y_1$ is an oxygen atom.

m represents an integer of 2 to 6.

Two of $X_1$, $X_2$, and $Y_2$ may be bonded to each other to form a ring.

Examples of the alkyl group represented by R in General Formula (1) include a methyl group, an ethyl group, a propyl group, an n-butyl group, a sec-butyl group, a hexyl group, an octyl group, a cyclopropyl group, a cyclobutyl group, a cyclopentyl group, a cyclohexyl group, a cyclooctyl group, an adamantyl group, a norbornyl group, an isobornyl group, a camphanyl group, a dicyclopentyl group, an α-pinel group, a tricyclodecanyl group, a tetracyclododecyl group, and an androstanyl group.

The specific examples and preferable aspect of $X_1$, $X_2$, $Y_2$, Z, and m in General Formula (1) are the same as those of each group in General Formula (1-0).

In one aspect of the present invention, the cross-linking agent (C) is preferably represented by the following General Formula (1-1).

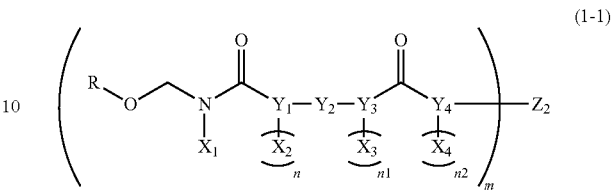

Each symbol in the formula has the same meaning as corresponding each group in General Formulas (1) and (2).

The molecular weight (Mw) of the cross-linking agent (C) is preferably 450 or greater, and particularly preferably 450 to 1500, from the viewpoint of non-volatility at the time of post exposure bake during film formation.

Specific examples of the cross-linking agent (C) are shown below, but the present invention is not limited thereto.

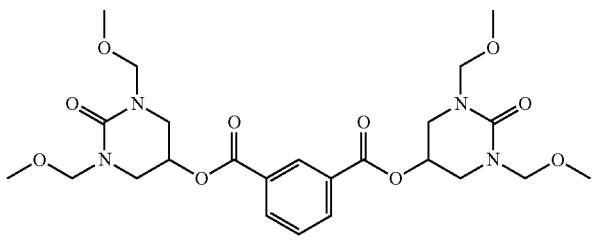
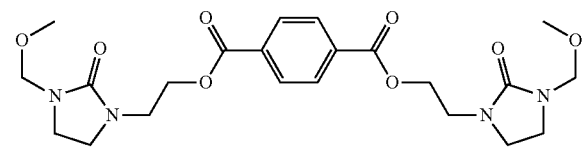

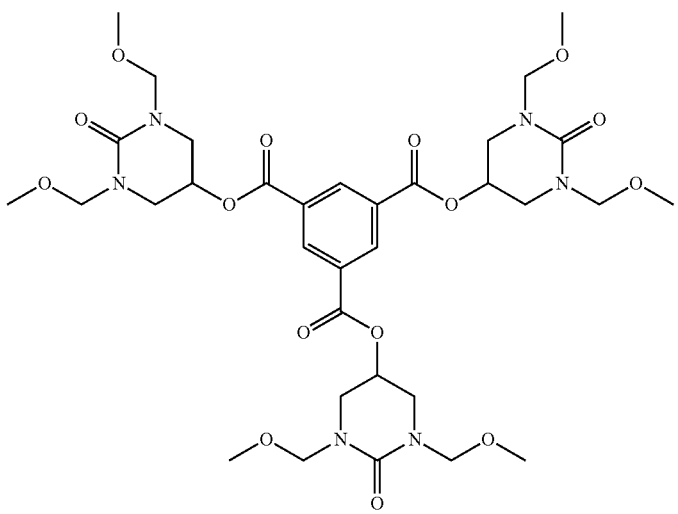

-continued
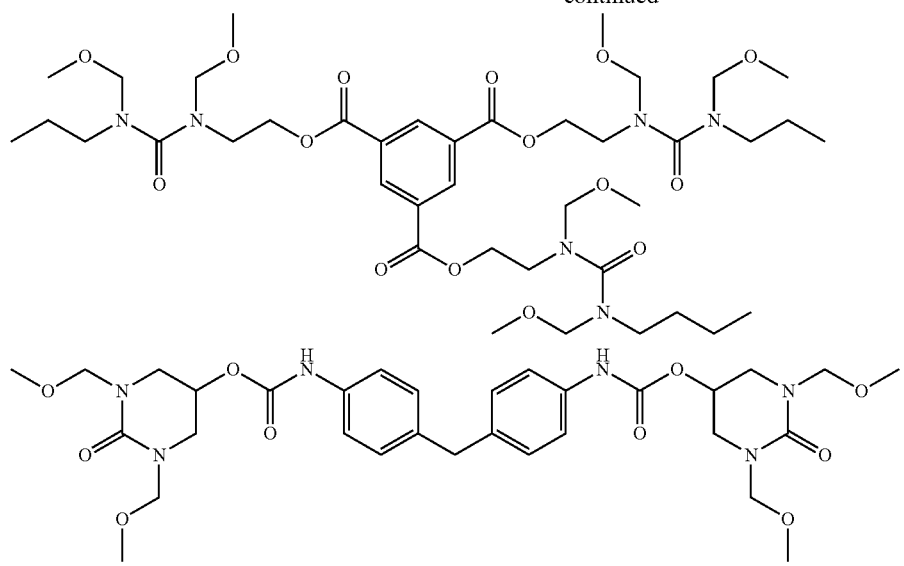
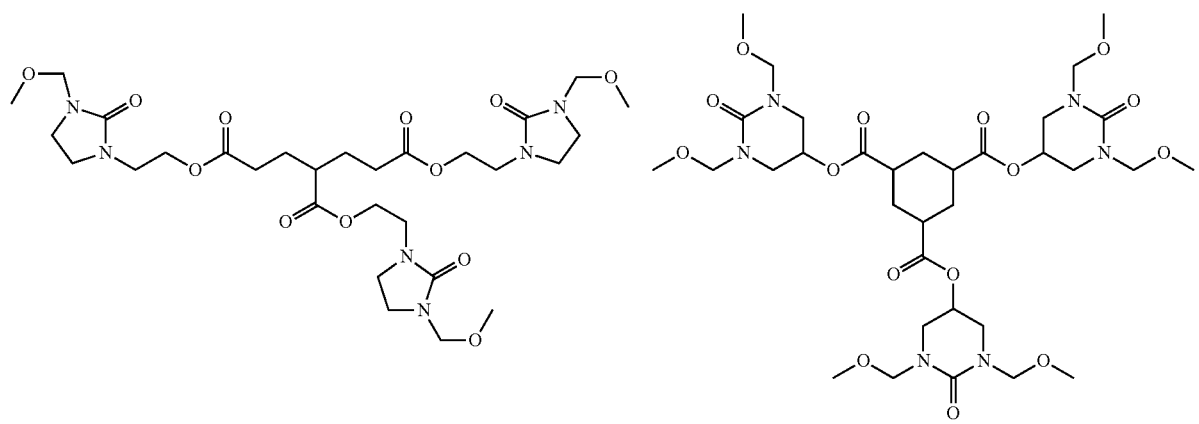
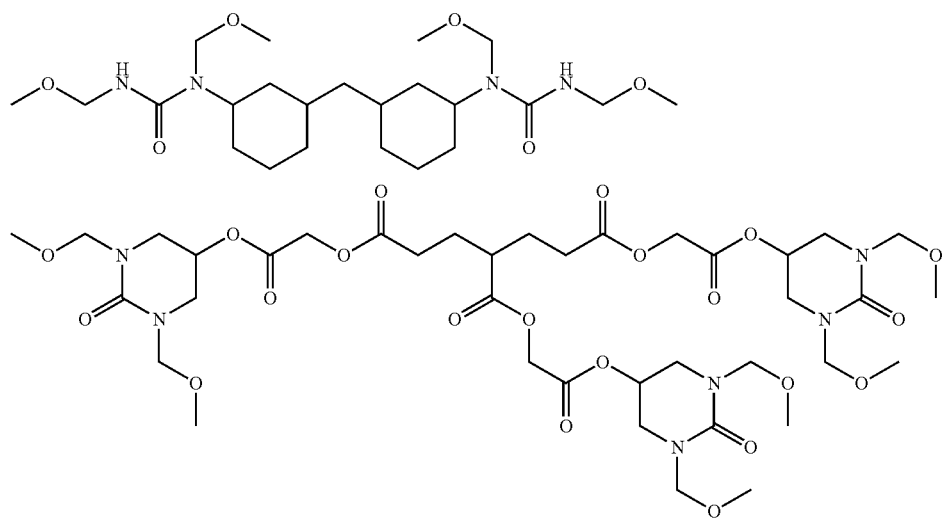

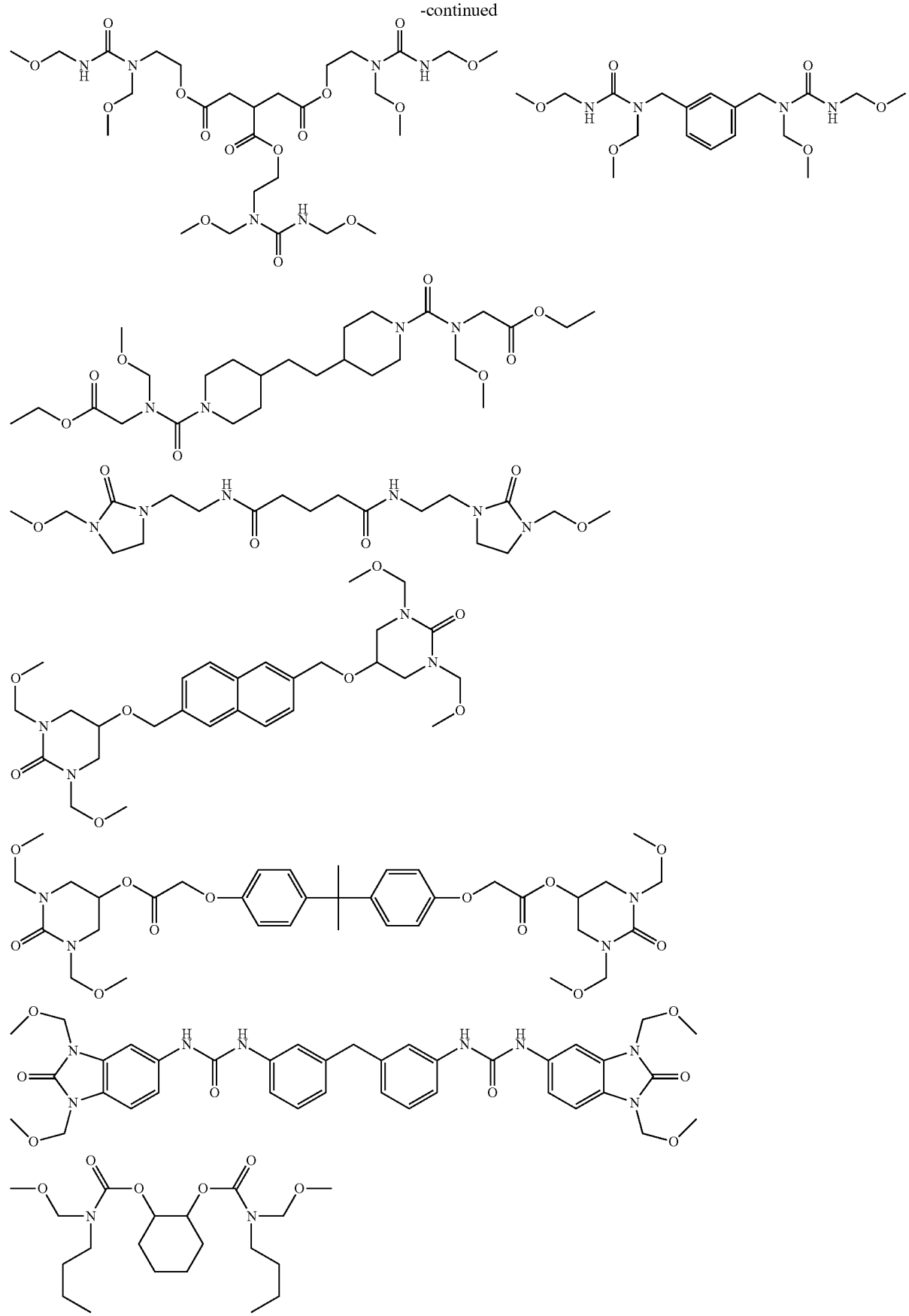

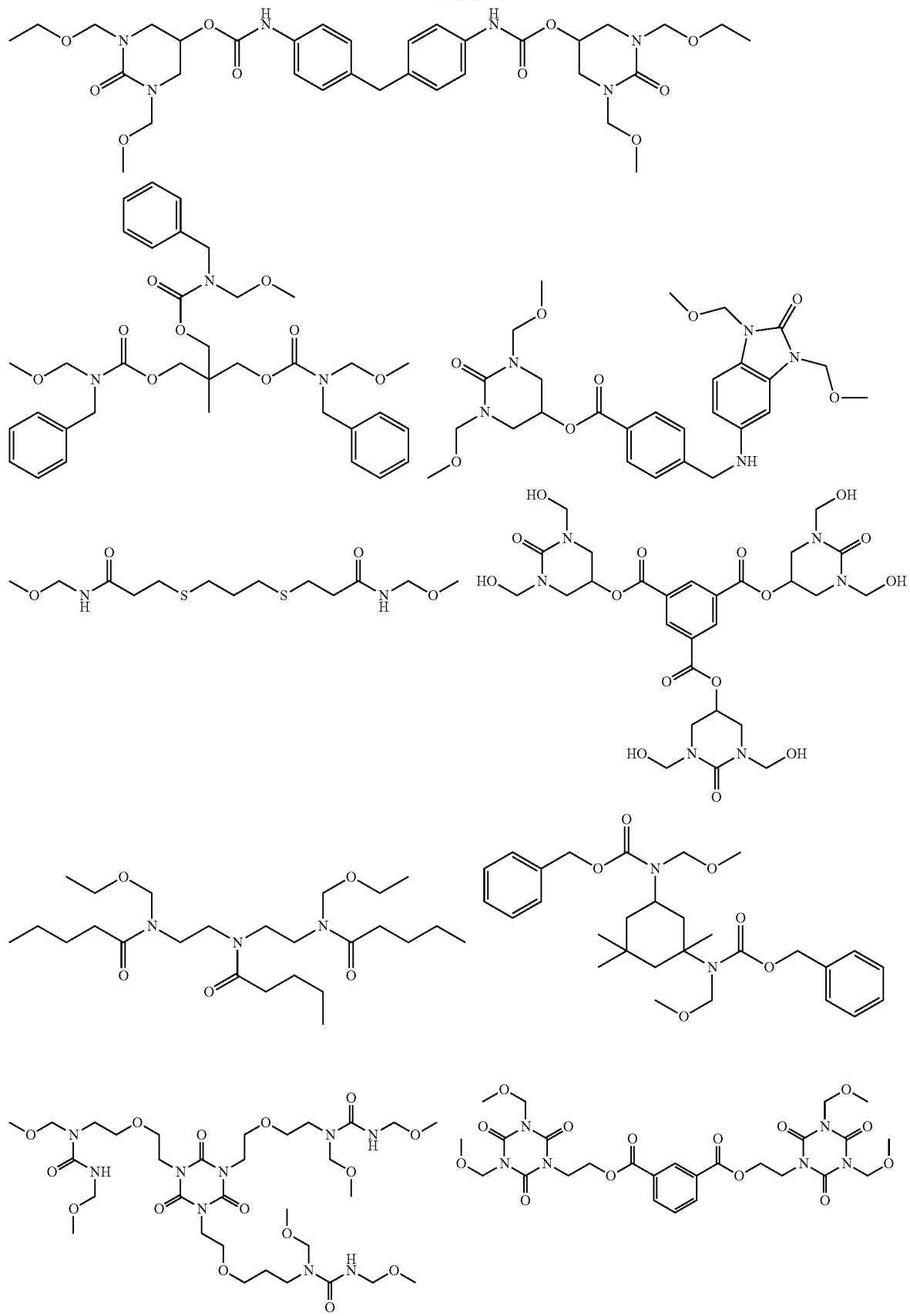

The content of the cross-linking agent (C) in the present invention is preferably 3% by mass to 65% by mass and more preferably 5% by mass to 50% by mass, based on the solid content of the composition.

In addition, in the present invention, the cross-linking agent (C) may be used alone, or two or more kinds thereof may be used in combination.

For example, the cross-linking agent (C) of the present invention can be synthesized by the following method. That is, in the method, urea, urethane, or an amide group having a hydrogen atom on the nitrogen atom in the compound (I) is alkoxymethylated or hydroxymethylated by the method described in JP2012-31233A or Bull. Chem. Soc. Jpn., 62, 2657 (1989) (compound (II)) and then connection is performed by an arbitrary method, or connection is performed by an arbitrary method (compound (III)) and then alkoxymethylation or hydroxymethylation is performed.

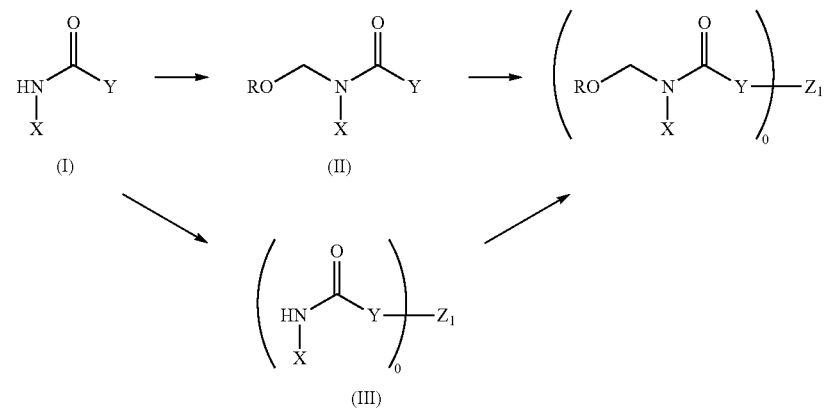

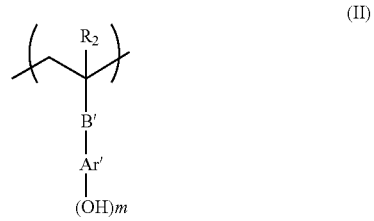

In the formula, $R_2$ represents a hydrogen atom, a methyl group which may have a substituent, or a halogen atom.

B' represents a single bond or a divalent connecting group.

Ar' represents an aromatic ring group.

m represents an integer of 1 or greater.

<(A) Alkali Soluble Resin>

The composition of the present invention contains an alkali soluble resin (A). Although the resin (A) is not particularly limited as long as it is alkali soluble, the resin (A) is preferably a resin containing a phenolic hydroxyl group.

The phenolic hydroxyl group in the present invention is a group obtained by substituting a hydrogen atom of an aromatic ring group with a hydroxy group. The aromatic ring of the aromatic ring group may be a monocyclic or polycyclic aromatic ring, and examples thereof include a benzene ring and a naphthalene ring.

The composition of the present invention formed by containing the resin (A) and the cross-linking agent (C) is preferably used to form a negative-type pattern. For example, in a case where the compositions of the present invention further contains an acid generator (B) described below, in the exposed portion, a cross-linking reaction proceeds between the resin (A) and the cross-linking agent (C) due to the action of an acid generated from the acid generator, whereby a negative-type pattern is formed.

The resin (A) preferably contains a repeating unit having at least one type of phenolic hydroxyl group. Although the repeating unit having a phenolic hydroxyl group is not particularly limited, the repeating unit is preferably a repeating unit represented by the following General Formula (II).

Examples of the methyl group which may have a substituent represented by $R_2$ include a trifluoromethyl group and a hydroxymethyl group.

$R_2$ is preferably a hydrogen atom or a methyl group, and preferably a hydrogen atom from the viewpoint of developability.

Preferable examples of the divalent connecting group represented by B' include a carbonyl group, an alkylene group (preferably having 1 to 10 carbon atoms, and more preferably having 1 to 5 carbon atoms), a sulfonyl group (—S(=O)$_2$—), —O—, —NH—, or a divalent connecting group obtained by combining these.

B' preferably represents a single bond, a carbonyloxy group (—C(=O)—O—), or a —C(=O)—NH—, more preferably represents a single bond or a carbonyloxy group (—C(=O)—O—), and particularly preferable represents a single bond, from the viewpoint of improvement of dry etching resistance.

The aromatic ring represented by Ar' is a monocyclic or polycyclic aromatic ring, and examples thereof include an aromatic hydrocarbon ring which may have a substituent having 6 to 18 carbon atoms, such as a benzene ring, a naphthalene ring, an anthracene ring, a fluorene ring, or a phenanthrene ring, and an aromatic hetero ring including a hetero ring, such as a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring, or a thiazole ring. Among these, a benzene ring or a naphthalene ring is preferable from the viewpoint of resolution, and a benzene ring is most preferable from the viewpoint of sensitivity.

m is preferably an integer of 1 to 5, and most preferably 1. Although, when m is 1 and Ar' is a benzene ring, the substitution position of —OH may be an ortho position, a meta position, or the para position with respect to the bonding position with B' of the benzene ring (in a case where B' is a single bond, the polymer main chain), the substitution position is preferably the para position or a meta position and more preferably the para position, from the viewpoint of cross-linking reactivity.

The aromatic ring represented by Ar' may have a substituent other than the group represented by —OH described above, and examples of the substituent include an alkyl group, a cycloalkyl group, a halogen atom, a hydroxyl group, an alkoxy group, a carboxyl group, an alkoxycarbonyl group, an alkylcarbonyl group, an alkylcarbonyloxy group, an alkyl sulfonyloxy group, and an arylcarbonyl group.

The repeating unit having a phenolic hydroxyl group is more preferably a repeating unit represented by the following General Formula (2) from the viewpoint of cross-linking reactivity, developability, and dry etching resistance.

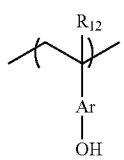

(2)

In General Formula (2), $R_{12}$ represents a hydrogen atom or a methyl group.

Ar represents an aromatic ring.

$R_{12}$ represents a hydrogen atom or a methyl group, and preferably a hydrogen atom from the viewpoint of developability.

Ar in General Formula (2) has the same meaning as Ar' in General Formula (II), and the preferable range thereof is also the same. The repeating unit represented by General Formula (2) is preferably a repeating unit derived from hydroxystyrene (that is, a repeating unit in which $R_{12}$ is a hydrogen atom, and Ar is a benzene ring, in General Formula (2)) from the viewpoint of sensitivity.

The resin (A) may be configured of only the repeating unit having a phenolic hydroxyl group as described above. The resin (A) may have a repeating unit as described below other than the repeating unit having a phenolic hydroxyl group as described above. In this case, the content of the repeating unit having a phenolic hydroxyl group is preferably 10 mol % to 98 mol %, more preferably 30 mol % to 97 mol %, and still more preferably 40 mol % to 95 mol %, with respect to the entirety of repeating units of the resin (A). Thus, in particular, in a case where the resist film is a thin film (for example, a case where the thickness of the resist film is 10 nm to 150 nm), the dissolution rate into an alkali developer of the exposed portion of the active light sensitive or radiation sensitive film of the present invention formed by using the resin (A) can be more reliably reduced (that is, the dissolution rate of the active light sensitive or radiation sensitive film formed by using the resin (A) can be more reliably controlled to become optimum). As a result, it is possible to more reliably improve the sensitivity.

Examples of the repeating unit having a phenolic hydroxyl group are shown below, but the present invention is not limited thereto.

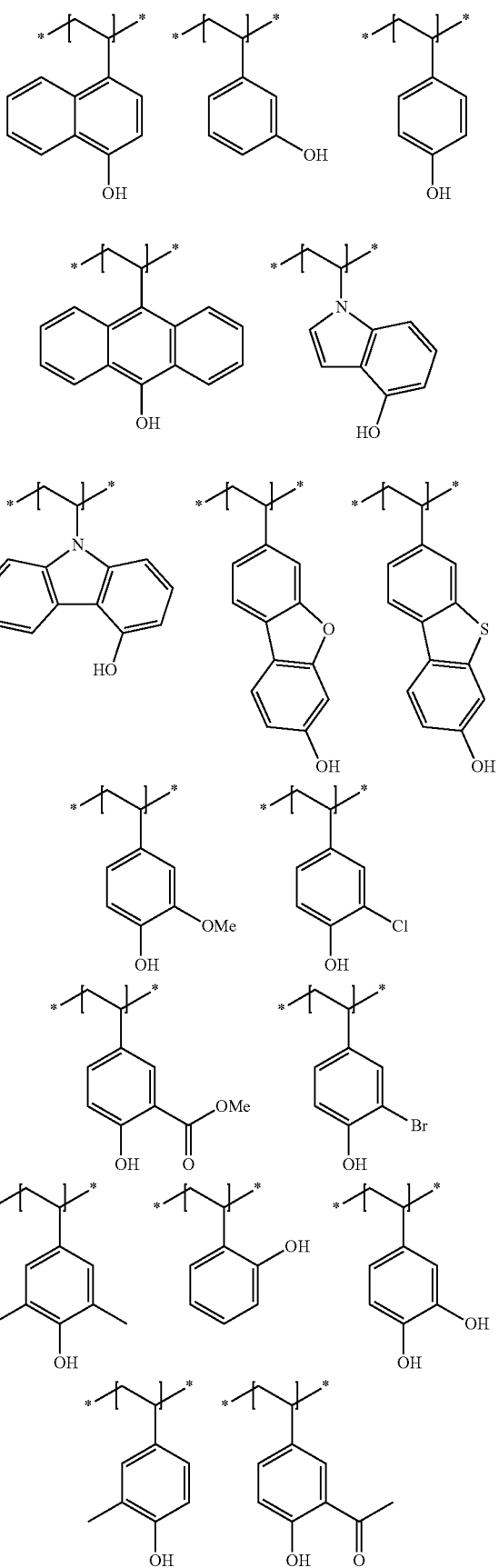

21
-continued
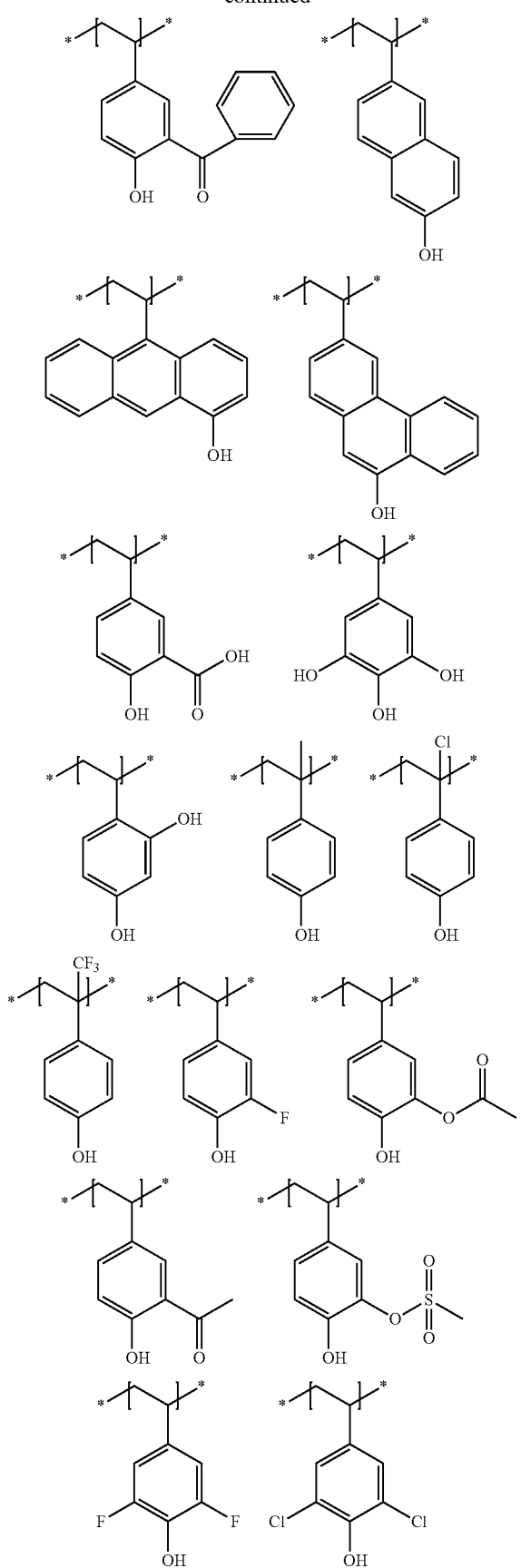
22
-continued
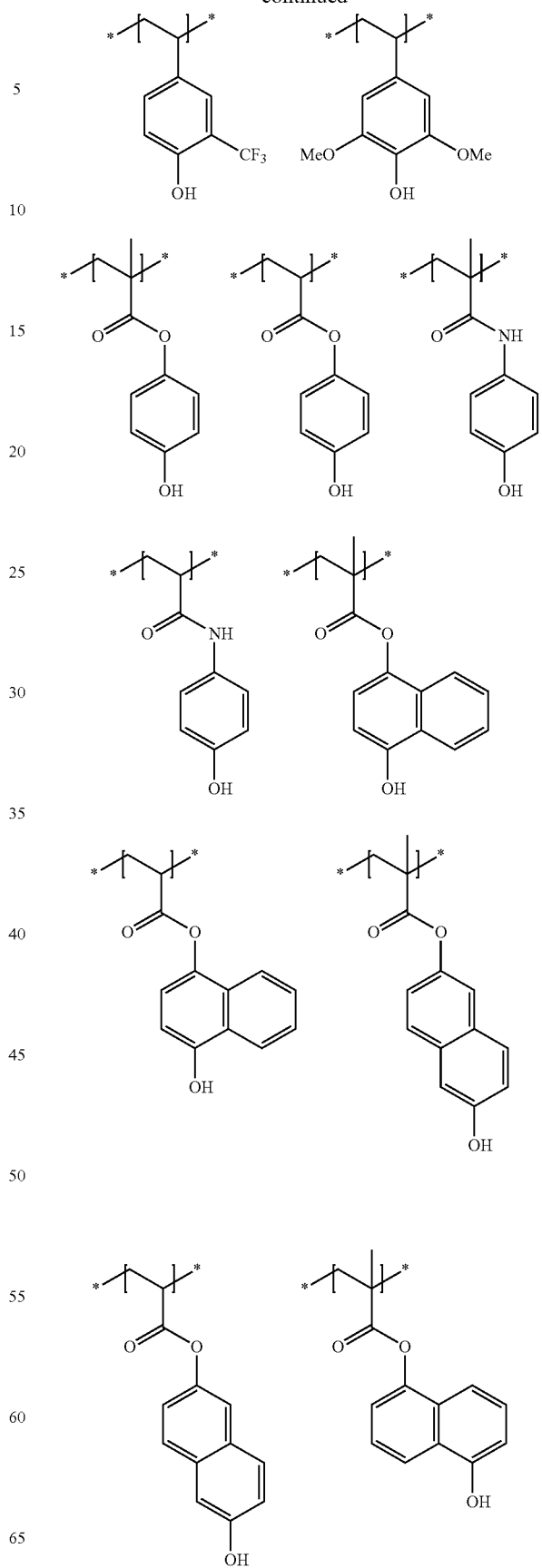

-continued

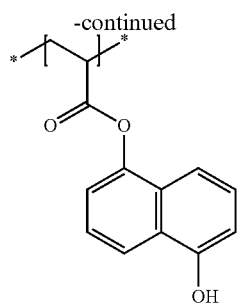

It is preferable that the resin (A) is a group having a nonacid degradable polycyclic alicyclic hydrocarbon structure and has a structure in which the hydrogen atoms of the phenolic hydroxyl group has been substituted, from the viewpoint that a high glass transition temperature (Tg) is obtained, and dry etching resistance is improved.

When the resin (A) has a specific structure described above, the glass transition temperature (Tg) of the resin(A) becomes high, it is possible to form a very hard resist film, and it is possible to control the diffusibility of an acid and dry etching resistance. Therefore, the diffusibility of an acid in the exposed portion to active light or radiation such as an electron beam or extreme ultraviolet rays is extremely suppressed, and as a result, the resolving power, a pattern shape, and LER of a fine pattern are further improved. In addition, it is thought that the resin (A) having a nonacid degradable polycyclic alicyclic hydrocarbon structure contributes to further improvement of dry etching resistance. Furthermore, details are not clear, but, it is estimated that since the polycyclic alicyclic hydrocarbon structure has high hydrogen radical donating properties and becomes a hydrogen source at the time of decomposition of a photoacid generator, decomposition efficiency of a photoacid generator is further improved, and acid generation efficiency is further increased, and it is thought that this contributes to excellent sensitivity.

In the above-described specific structure which the resin (A) according to the present invention may have, an aromatic ring such as a benzene ring and a group having a nonacid degradable polycyclic alicyclic hydrocarbon structure are connected through an oxygen atom derived from a phenolic hydroxyl group. As described above, it is estimated that this structure not only contributes to the high dry etching resistance, but also can raise the glass transition temperature (Tg) of the resin (A), and by the effects of combination thereof, higher resolving power is provided.

In the present invention, the nonacid degradability means a property that a decomposition reaction does not occur by an acid generated by a photoacid generator.

More specifically, a group having a nonacid degradable polycyclic alicyclic hydrocarbon structure is preferably a group stable with respect to an acid and an alkali. The group stable with respect to an acid and an alkali means a group which does not exhibit acid-decomposability or alkali-decomposability. The acid-decomposability described here means a property that a decomposition reaction occurs due to the action of an acid generated by a photoacid generator.

In addition, the alkali-decomposability means a property that a decomposition reaction occurs due to the action of an alkali developer, and as a group which exhibits the alkali-decomposability, a group (for example, a group having a lactone structure or the like) of which the dissolution rate in an alkali developer is increased due to decomposition by the action of the alkali developer known in the related art, included in a resin suitably used in a positive chemical amplified resist composition is exemplified.

Although the group having a polycyclic alicyclic hydrocarbon structure is not particularly limited as long as it is a monovalent group having a polycyclic alicyclic hydrocarbon structure, the group preferably has 5 to 40 total carbon atoms, and more preferably has 7 to 30 total carbon atoms. The polycyclic alicyclic hydrocarbon structure may have an unsaturated bond in the ring.

The polycyclic alicyclic hydrocarbon structure in a group having a polycyclic alicyclic hydrocarbon structure means a structure having a plurality of monocyclic type alicyclic hydrocarbon groups or a polycyclic type alicyclic hydrocarbon structure, and may be a bridged type. The monocyclic type alicyclic hydrocarbon group is preferably a cycloalkyl group having 3 to 8 carbon atoms, and examples thereof include a cyclopropyl group, a cyclopentyl group, a cyclohexyl group, a cyclobutyl group, and a cyclooctyl group, and the structure having a plurality of monocyclic type alicyclic hydrocarbon groups has a plurality of these groups. The structure having a plurality of monocyclic type alicyclic hydrocarbon groups preferably has 2 to 4 monocyclic type alicyclic hydrocarbon groups, and particularly preferably has 2 monocyclic type alicyclic hydrocarbon groups.

Examples of the polycyclic type alicyclic hydrocarbon structure include a bicyclo structure, a tricyclo structure, and a tetracyclo structure, having 5 or more carbon atoms, and the polycyclic type alicyclic hydrocarbon structure is preferably a polycyclic cyclo structure having 6 to 30 carbon atoms, and examples thereof include an adamantane structure, a decalin structure, a norbornane structure, a norbornene structure, a cedrol structure, an isobornane structure, a bornane structure, a dicyclopentane structure, an α-pinene structure, a tricyclodecane structure, a tetracyclododecane structure, and an androstane structure. Moreover, some of the carbon atoms in a monocyclic or polycyclic cycloalkyl group may be substituted with a heteroatom such as an oxygen atom.

Preferable examples of the polycyclic alicyclic hydrocarbon structure include an adamantane structure, a decalin structure, a norbornane structure, a norbornene structure, a cedrol structure, a structure having a plurality of cyclohexyl groups, a structure having a plurality of cycloheptyl groups, a structure having a plurality of cyclooctyl groups, a structure having a plurality of cyclodecanyl groups, a structure having a plurality of cyclododecanyl groups, and a tricyclodecane structure, and an adamantane structure is most preferable from the viewpoint of dry etching resistance (that is, the group having a nonacid degradable polycyclic alicyclic hydrocarbon structure is most preferably a group having a nonacid degradable adamantane structure).

The chemical formulas of these polycyclic alicyclic hydrocarbon structure (for the structure having a plurality of monocyclic type alicyclic hydrocarbon groups, a monocyclic type alicyclic hydrocarbon structure corresponding to the monocyclic type alicyclic hydrocarbon group (specifically, structures of the following Formulas (47) to (50))) are shown below.

 (1)

 (2)

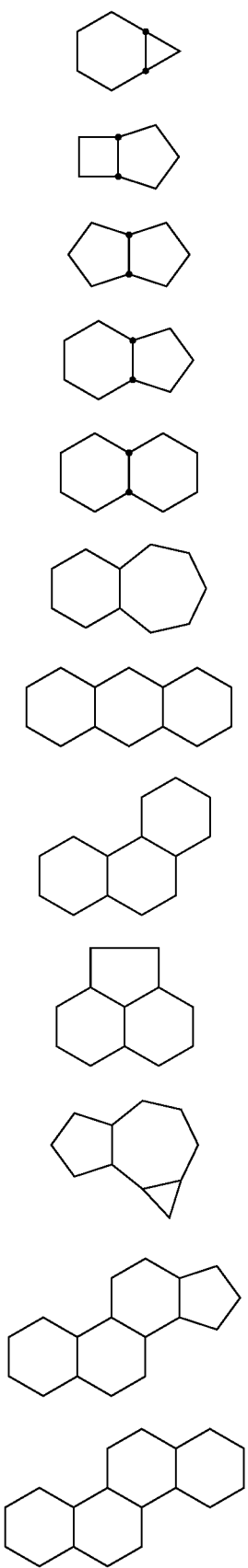
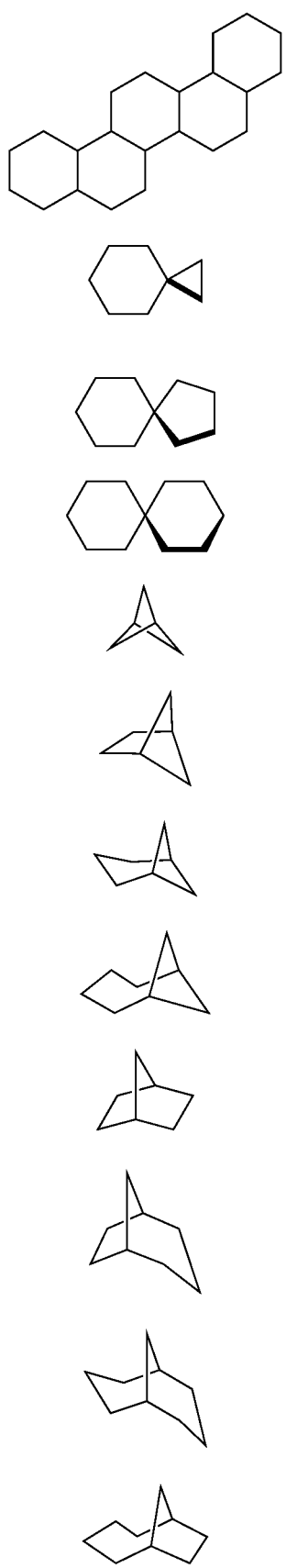

-continued
(27)
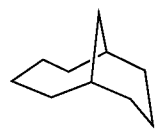
(28)
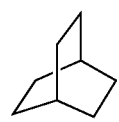
(29)
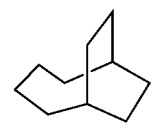
(30)
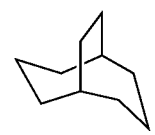
(31)
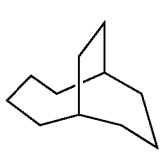
(32)
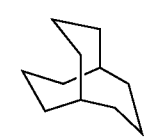
(33)
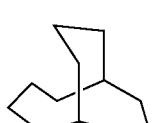
(34)
(35)
(36)
(37)
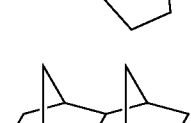
(38)
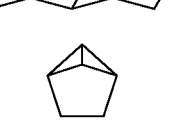
-continued
(39)
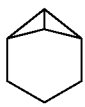
(40)
(41)
(42)
(43)
(44)
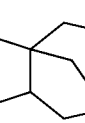
(45)
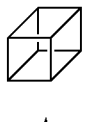
(46)
(47)
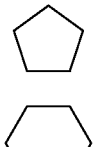
(48)
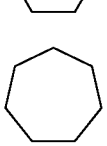
(49)
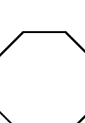
(50)
(51)

The polycyclic alicyclic hydrocarbon structure may have a substituent, and examples of the substituent include an alkyl group (preferably having 1 to 6 carbon atoms), a cycloalkyl group (preferably having 3 to 10 carbon atoms), an aryl group (preferably having 6 to 15 carbon atoms), a halogen atom, a hydroxyl group, an alkoxy group (preferably having 1 to 6 carbon atoms), a carboxyl group, a carbonyl group, a thiocarbonyl group, an alkoxycarbonyl group (preferably having 2 to 7 carbon atoms), and a group obtained by combining these groups (preferably having 1 to 30 total carbon atoms and more preferably 1 to 15 total carbon atoms).

The polycyclic alicyclic hydrocarbon structure is preferably a structure represented by any one of Formulas (7), (23), (40), (41), and (51) or a structure having two monovalent groups in which an arbitrary hydrogen atom in the structure of Formula (48) is used as a direct bond, more preferably the structure represented by any one of Formulas (23), (40), and (51) or the structure having two monovalent groups in which an arbitrary hydrogen atom in the structure of Formula (48) is used as a direct bond, and most preferably the structure represented by Formula (40).

A group having the polycyclic alicyclic hydrocarbon structure is preferably a monovalent group in which an arbitrary hydrogen atom in the polycyclic alicyclic hydrocarbon structure is used as a direct bond.

A structure in which a hydrogen atom of an phenolic hydroxyl group has been substituted with the group having the nonacid degradable polycyclic alicyclic hydrocarbon structure is preferably contained in the resin (A) as a repeating unit having a structure in which a hydrogen atom of an phenolic hydroxyl group has been substituted with the group having the nonacid degradable polycyclic alicyclic hydrocarbon structure, and more preferably contained in the resin (A) as a repeating unit represented by the following General Formula (3).

The aromatic ring represented by $Ar_1$ may have a substituent other than the group represented by —OX described above, and examples of the substituent include an alkyl group (preferably having 1 to 6 carbon atoms), a cycloalkyl group (preferably having 3 to 10 carbon atoms), an aryl group (preferably having 6 to 15 carbon atoms), a halogen atom, a hydroxyl group, an alkoxy group (preferably having 1 to 6 carbon atoms), a carboxyl group, and an alkoxycarbonyl group (preferably having 2 to 7 carbon atoms). The substituent is preferably an alkyl group, an alkoxy group, or an alkoxycarbonyl group, and more preferably an alkoxy group.

X represents a group having a nonacid degradable polycyclic alicyclic hydrocarbon structure. The specific examples and the preferable range of the group having a nonacid degradable polycyclic alicyclic hydrocarbon structure represented by X are the same as those described above. X is more preferably a group represented by —Y—$X_2$ in the following General Formula (4).

m2 is preferably an integer of 1 to 5, and most preferably 1. Although, when m2 is 1 and $Ar_1$ is a benzene ring, the substitution position of —OX may be the para position, a meta position, or an ortho position, with respect to the bonding position with the polymer main chain of the benzene ring, and the substitution position is preferably the para position or a meta position, and more preferably the para position.

In the present invention, the repeating unit represented by General Formula (3) is preferably a repeating unit represented by the following General Formula (4).

When the resin (A) having the repeating unit represented by General Formula (4) is used, the Tg of the resin(A) becomes high, and a very hard resist film is formed, and thus, it is possible to more reliably control the diffusibility of an acid and dry etching resistance.

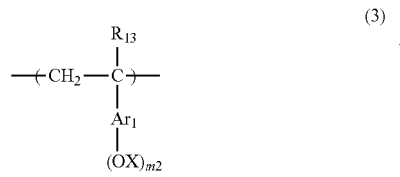

(3)

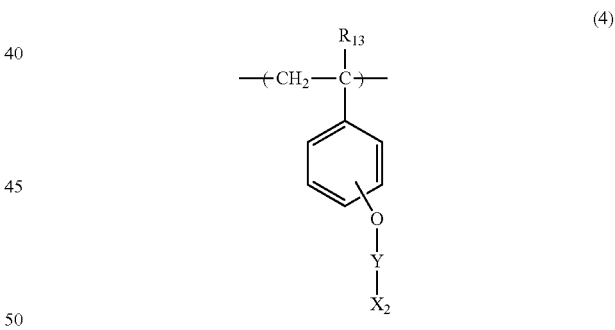

(4)

In General Formula (3), $R_{13}$ represents a hydrogen atom or a methyl group.

X represents a group having a nonacid degradable polycyclic alicyclic hydrocarbon structure.

$Ar_1$ represents an aromatic ring.

m2 is an integer of 1 or greater.

In General Formula (3), $R_{13}$ represents a hydrogen atom or a methyl group, and particularly preferably represents a hydrogen atom.

Examples of the aromatic ring represented by $Ar_1$ in General Formula (3) include an aromatic hydrocarbon ring which may have a substituent having 6 to 18 carbon atoms, such as a benzene ring, a naphthalene ring, an anthracene ring, a fluorene ring, and a phenanthrene ring, or an aromatic hetero ring including a hetero ring, such as a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring, or a thiazole ring. Among these, a benzene ring or a naphthalene ring is preferable from the viewpoint of resolution, and a benzene ring is most preferable.

In General Formula (4), $R_{13}$ represents a hydrogen atom or a methyl group.

Y represents a single bond or a divalent connecting group.

$X_2$ represents a nonacid degradable polycyclic alicyclic hydrocarbon group.

Preferable examples of the repeating unit represented by General Formula (4) used in the present invention are described below.

In General Formula (4), $R_{13}$ represents a hydrogen atom or a methyl group, and particularly preferably represents a hydrogen atom.

In General Formula (4), Y is preferably a divalent connecting group. The divalent connecting group represented by Y is preferably a carbonyl group, a thiocarbonyl group, an alkylene group (preferably having 1 to 10 carbon atoms, and more preferably having 1 to 5 carbon atoms), a sulfonyl group, —COCH₂—, —NH—, or a divalent connecting group formed by combining these (preferably having 1 to 20 total carbon atoms, and more preferably having 1 to 10 total carbon atoms), more preferably a carbonyl group, —COCH₂—, a sulfonyl group, —CONH—, or —CSNH—, still more preferably a carbonyl group or —COCH₂—, and particularly preferably a carbonyl group.

$X_2$ represents a polycyclic alicyclic hydrocarbon group, and is nonacid degradable. The polycyclic alicyclic hydrocarbon group preferably has 5 to 40 total carbon atoms, and more preferably 7 to 30 total carbon atoms. The polycyclic alicyclic hydrocarbon group may have an unsaturated bond in the ring.

Such a polycyclic alicyclic hydrocarbon group is a group having a plurality of monocyclic type alicyclic hydrocarbon groups or a polycyclic type alicyclic hydrocarbon group, and may be a bridged type. The monocyclic type alicyclic hydrocarbon group is preferably a cycloalkyl group having 3 to 8 carbon atoms, and examples thereof include a cyclopropyl group, a cyclopentyl group, a cyclohexyl group, a cyclobutyl group, and a cyclooctyl group, and the monocyclic type alicyclic hydrocarbon group has a plurality of these groups. The group having a plurality of monocyclic type alicyclic hydrocarbon groups preferably has 2 to 4 monocyclic type alicyclic hydrocarbon groups, and particularly preferably has 2 monocyclic type alicyclic hydrocarbon groups.

Examples of the polycyclic type alicyclic hydrocarbon group include a group having a bicyclo structure, a tricyclo structure, or a tetracyclo structure, having 5 or more carbon atoms, and the polycyclic type alicyclic hydrocarbon group is preferably a group having a polycyclic cyclo structure having 6 to 30 carbon atoms, and examples thereof include an adamantyl group, a norbornyl group, a norbornenyl group, an isoboronyl group, a camphanyl group, a dicyclopentyl group, an α-pinel group, a tricyclodecanyl group, a tetracyclododecyl group, and an androstanyl group. Moreover, some of the carbon atoms in a monocyclic or polycyclic cycloalkyl group may be substituted with a heteroatom such as an oxygen atom.

The polycyclic alicyclic hydrocarbon group represented by $X_2$ is preferably an adamantyl group, a decalin group, a norbornyl group, a norbornenyl group, a cedrol group, a group having a plurality of cyclohexyl groups, a group having a plurality of cycloheptyl groups, a group having a plurality of cyclooctyl groups, a group having a plurality of cyclodecanyl groups, a group having a plurality of cyclododecanyl groups, or a tricyclodecanyl group, and most preferably an adamantyl group from the viewpoint of dry etching resistance. Examples of the chemical formula of the polycyclic alicyclic hydrocarbon structure in the polycyclic alicyclic hydrocarbon group represented by $X_2$ include the same as the chemical formula of the polycyclic alicyclic hydrocarbon structure in the group having a polycyclic alicyclic hydrocarbon structure described above, and the preferable range thereof is also the same. Examples of the polycyclic alicyclic hydrocarbon group represented by $X_2$ include a monovalent group in which an arbitrary hydrogen atom in the polycyclic alicyclic hydrocarbon structure is used as a direct bond.

The alicyclic hydrocarbon group may have a substituent, and examples of the substituent include the same as those described above as a substituent which the polycyclic alicyclic hydrocarbon structure may have.

The substitution position of —O—Y—$X_2$ in General Formula (4) may be the para position, a meta position, or an ortho position, with respect to the bonding position with the polymer main chain of the benzene ring, and the substitution position is preferably the para position.

In the present invention, the repeating unit represented by General Formula (3) is most preferably a repeating unit represented by the following General Formula (4').

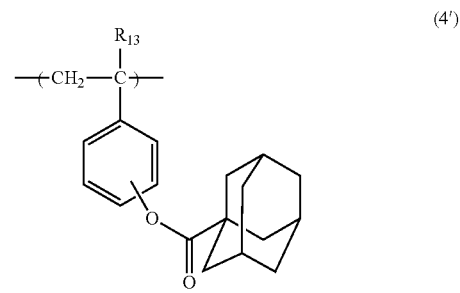

In General Formula (4'), $R_{13}$ represents a hydrogen atom or a methyl group.

In General Formula (4'), $R_{13}$ represents a hydrogen atom or a methyl group, and particularly preferably represents a hydrogen atom.

The substitution position of the adamantyl ester group in General Formula (4') may be the para position, a meta position, or an ortho position, with respect to the bonding position with the polymer main chain of the benzene ring, and the substitution position is preferably the para position.

Specific examples of the repeating unit represented by General Formula (3) include repeating units exemplified below.

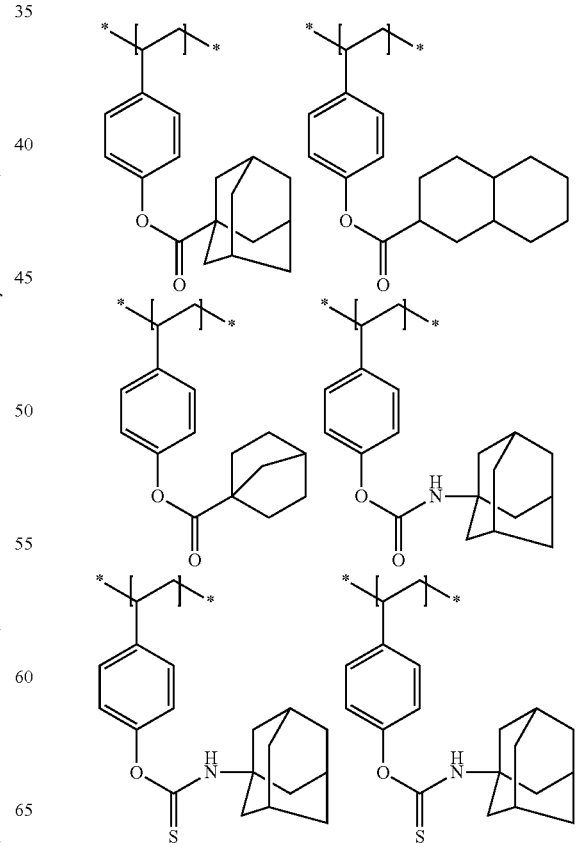

-continued
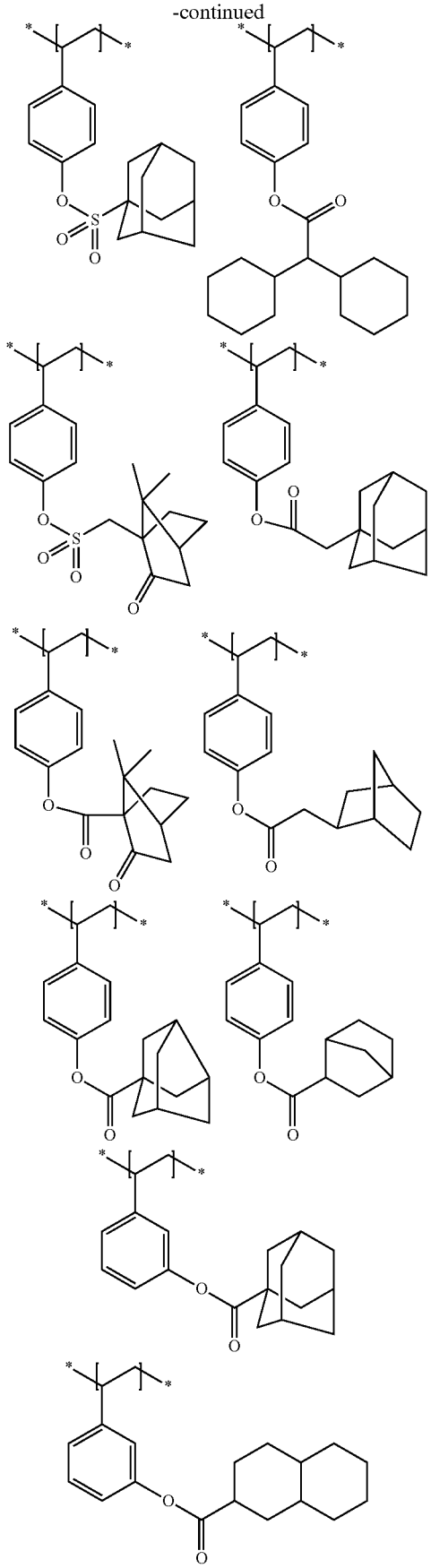
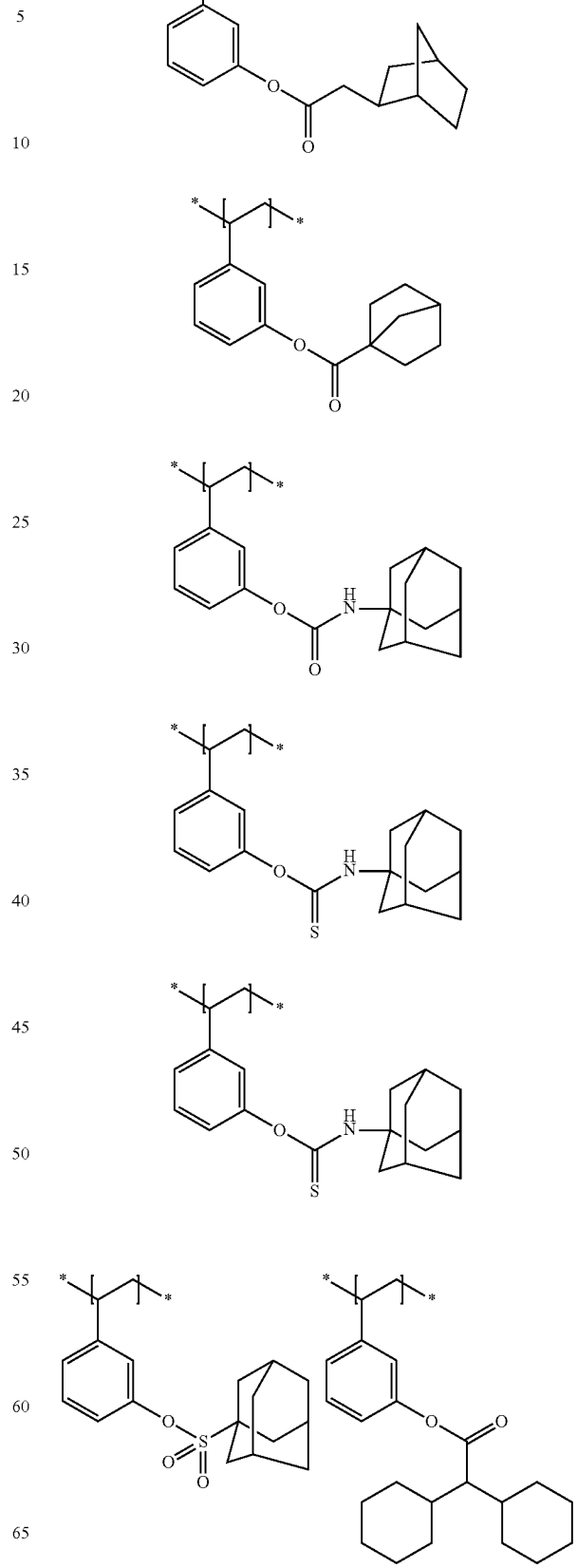

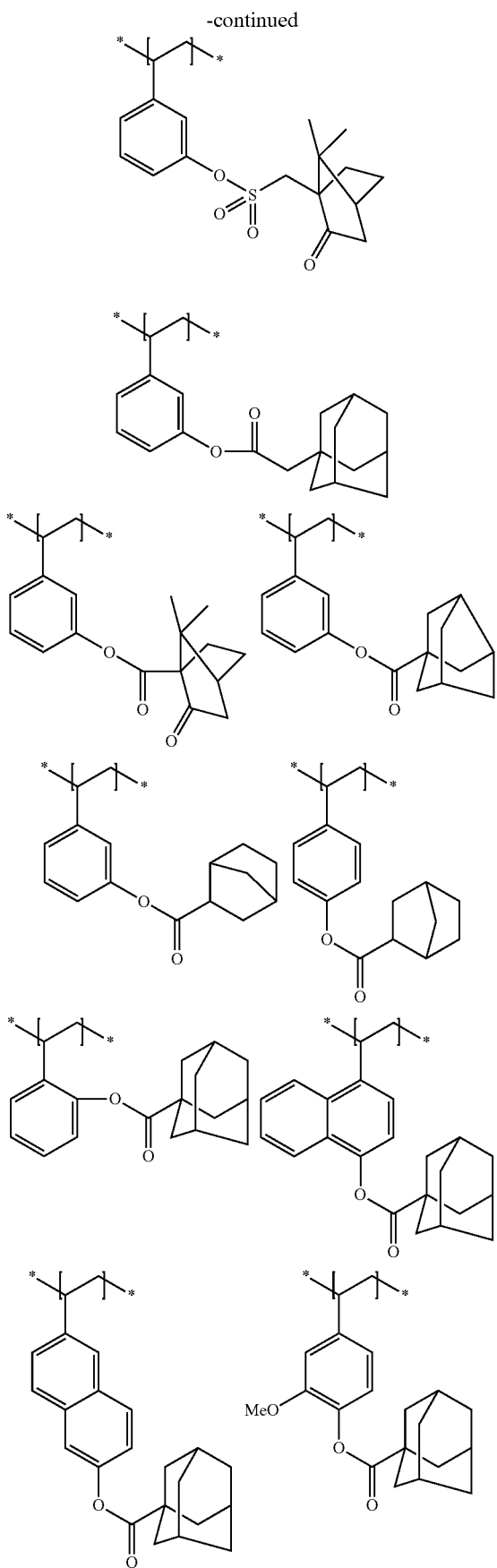

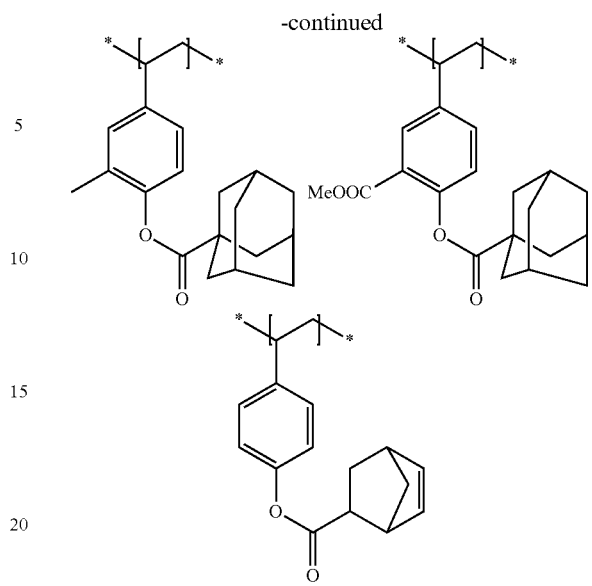

In a case where the resin (A) is a group having the nonacid degradable polycyclic alicyclic hydrocarbon structure and contains a repeating unit having a structure in which the hydrogen atoms of the phenolic hydroxyl group has been substituted, the content of the repeating unit is preferably 1 mol % to 40 mol % and more preferably 2 mol % to 30 mol %, with respect to the entirety of repeating units in the resin (A).

The resin (A) used in the present invention preferably further has a repeating unit (hereinafter, also referred to as "other repeating units") described below as a repeating unit other than the above-described repeating units.

Examples of the polymerizable monomer for forming other repeating units include styrene, alkyl-substituted styrene, alkoxy-substituted styrene, halogen-substituted styrene, O-alkylated styrene, O-acylated styrene, hydrogenated hydroxystyrene, maleic anhydride, an acrylic acid derivative (acrylic acid, acrylic acid ester, or the like), a methacrylic acid derivative (methacrylic acid, methacrylic acid ester, or the like), N-substituted maleimide, acrylonitrile, methacrylonitrile, vinyl naphthalene, vinyl anthracene, and indene which may have a substituent.

Although the resin (A) may contain or may not contain these other repeating units, in the case of containing, the content of these other repeating units in the compound (D) as a polymer compound is generally 1 mol % to 30 mol %, preferably 1 mol % to 20 mol %, and more preferably 2 mol % to 10 mol %, with respect to the entirety of repeating units constituting the compound (D) as a polymer compound.

The resin (A) can be synthesized by a known radical polymerization method, an anionic polymerization method, or a living radical polymerization method (an iniferter method). For example, in the anionic polymerization method, a vinyl monomer is dissolved in a suitable organic solvent, and the resultant product is reacted, typically, under cooling conditions using a metal compound (butyllithium or the like) as an initiator, whereby a polymer is obtained.

As the resin (A), a polyphenol compound prepared by a condensation reaction of aromatic ketone or aromatic aldehydes and a compound containing 1 to 3 phenolic hydroxyl groups (for example, JP2008-145539A), a calixarene derivative (for example, JP2004-18421A), a Noria derivative (for example, JP2009-222920A), or a polyphenol derivative (for example, JP2008-94782A) is also applicable, and the resin (A) may be synthesized by modifying using a polymer reaction.

In addition, the resin (A) is preferably synthesized by modifying a polymer synthesized by a radical polymerization method or an anionic polymerization method using a polymer reaction.

The weight average molecular weight of the resin (A) is preferably 1000 to 200000, more preferably 2000 to 50000, and still more preferably 2000 to 15000.

The dispersity (molecular weight distribution) (Mw/Mn) of the resin (A) is preferably 2.0 or less, and from the viewpoint of improvement of sensitivity and resolution, the dispersity of the resin (A) is preferably 1.0 to 1.80, more preferably 1.0 to 1.60, and most preferably 1.0 to 1.20. It is preferable to use living polymerization such as living anionic polymerization since the dispersity (molecular weight distribution) of the obtained polymer compound becomes uniform. The weight average molecular weight and dispersity of the resin (A) can be determined by using, for example, HLC-8120 (manufactured by TOSOH CORPORATION), TSK gel Multipore HXL-M (manufactured by TOSOH CORPORATION, 7.8 mmHD×30.0 cm) as a column, and THF (tetrahydrofuran) or NMP (N-methyl-2-pyrrolidone) as an eluent.

The content of the resin (A) in the composition of the present invention is preferably 30% by mass to 95% by mass, more preferably 40% by mass to 90% by mass, and particularly preferably 50% by mass to 85% by mass, with respect to the total solid content of the composition.

Specific examples of the resin (A) will be shown below, but the present invention is not limited thereto.

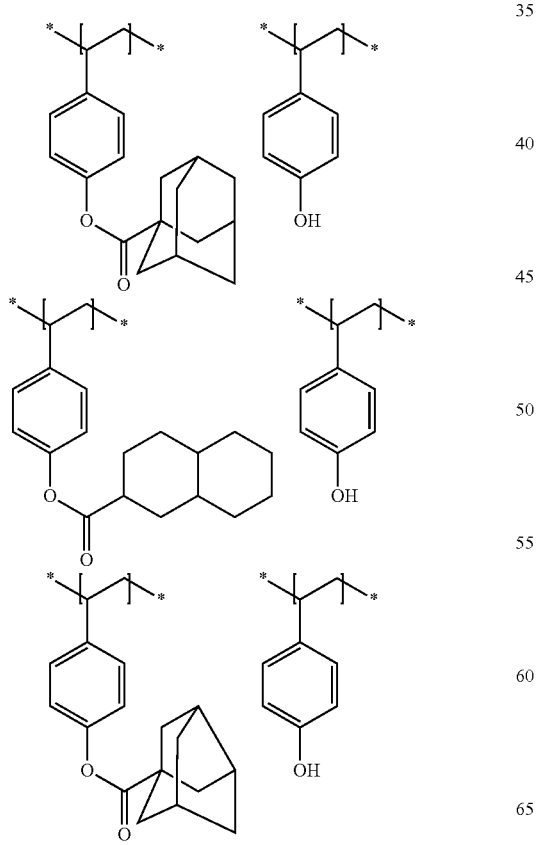

-continued

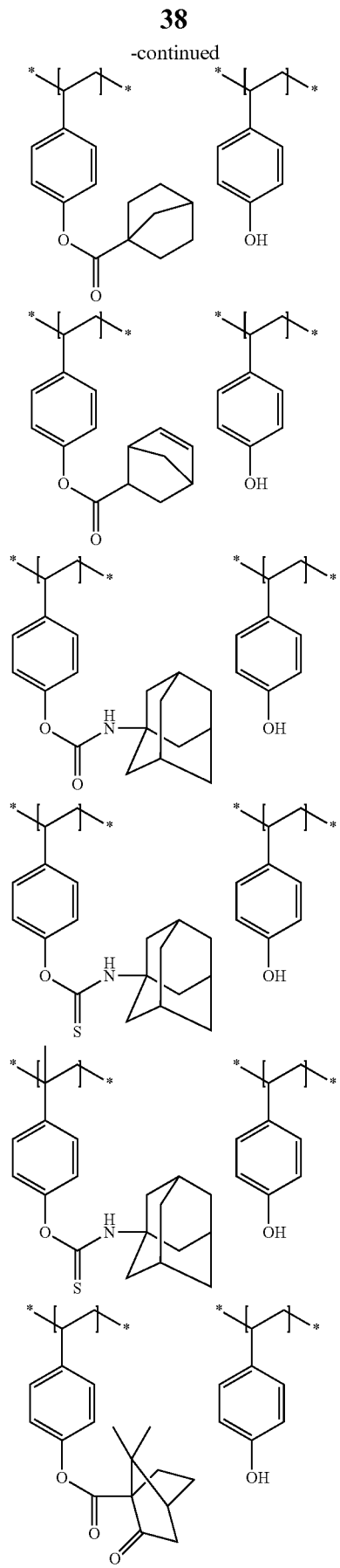

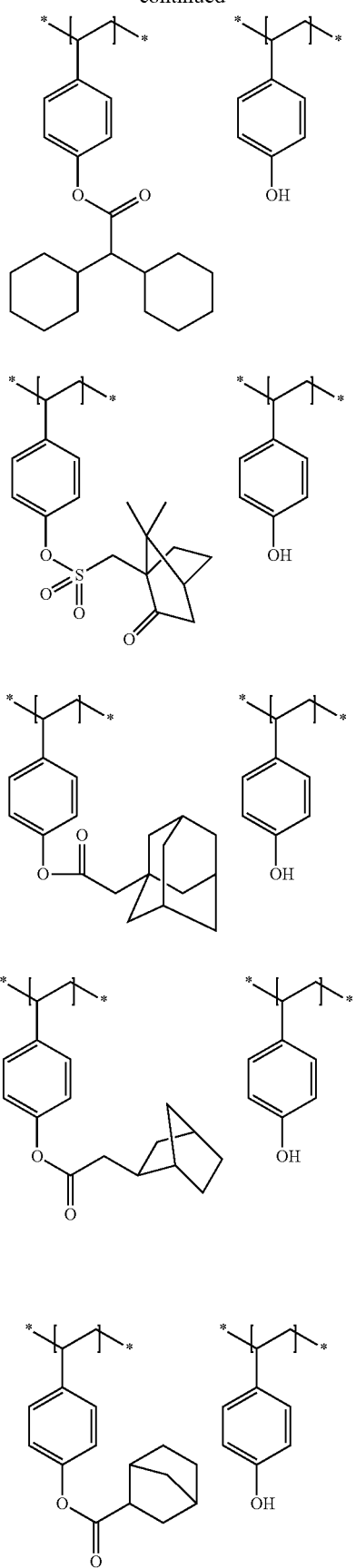
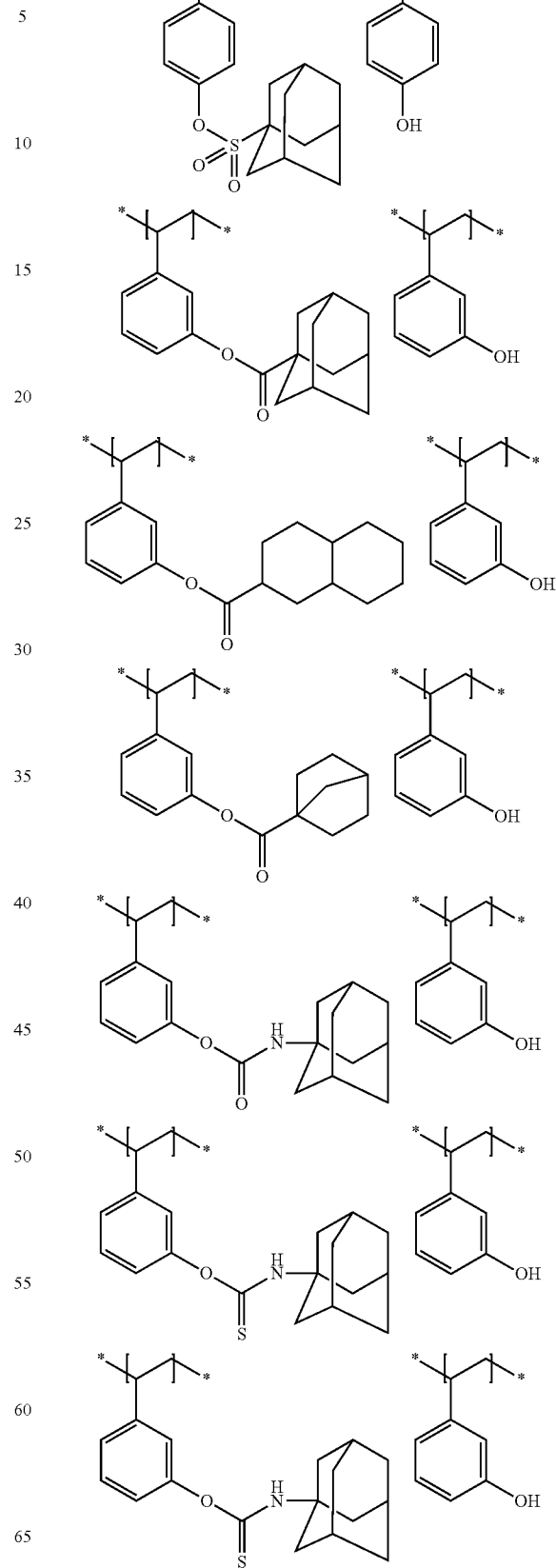

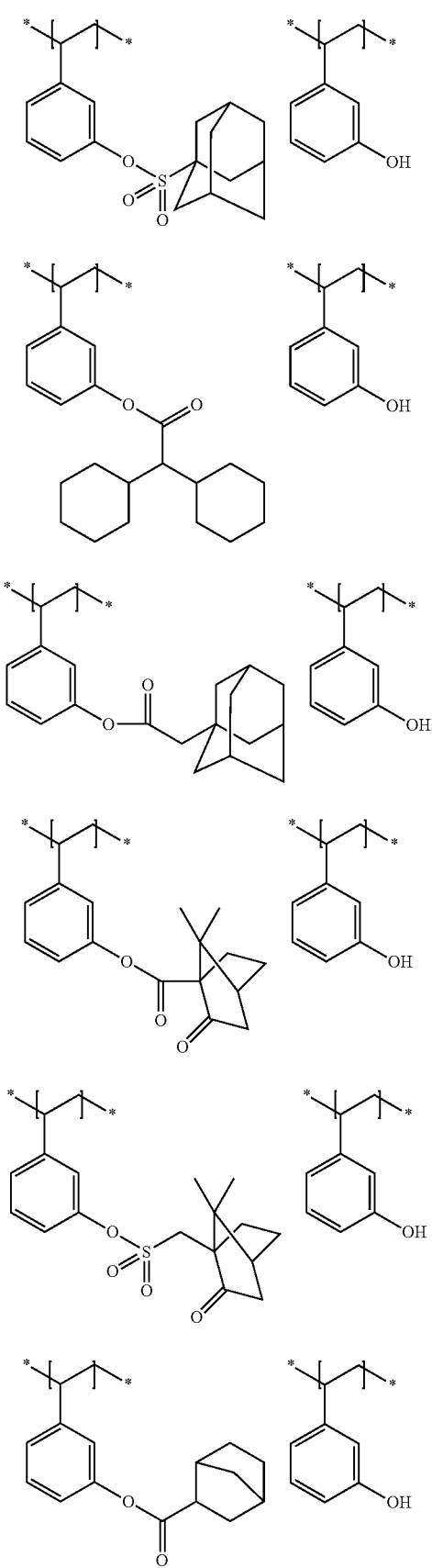
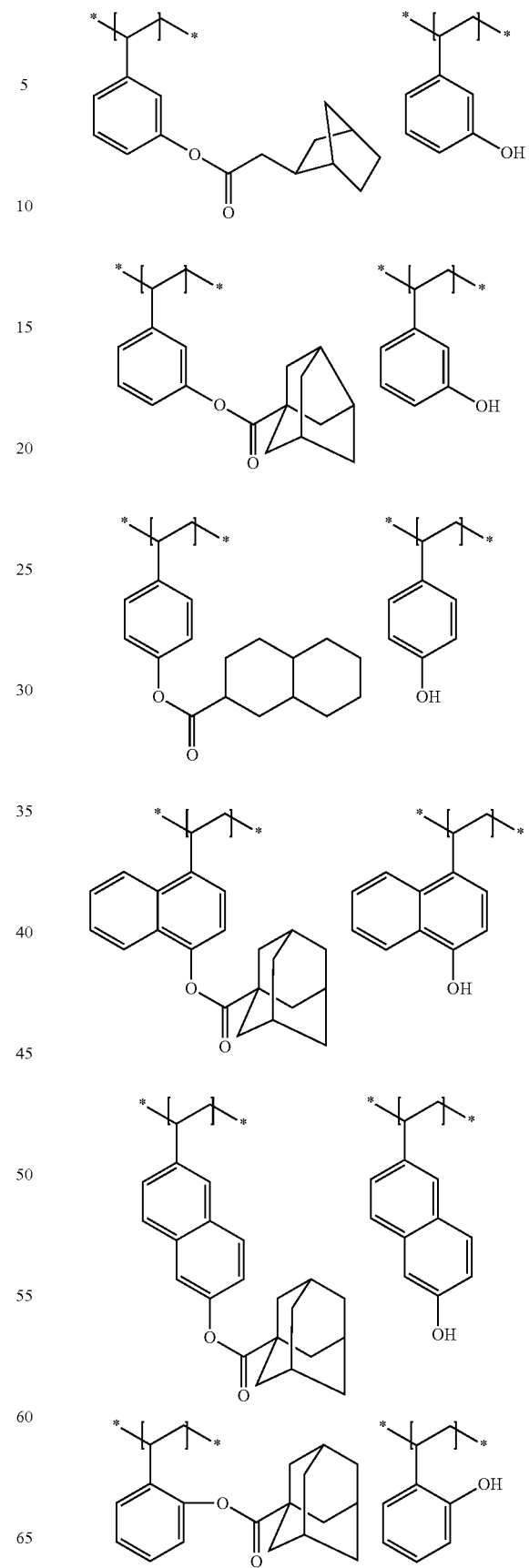

-continued
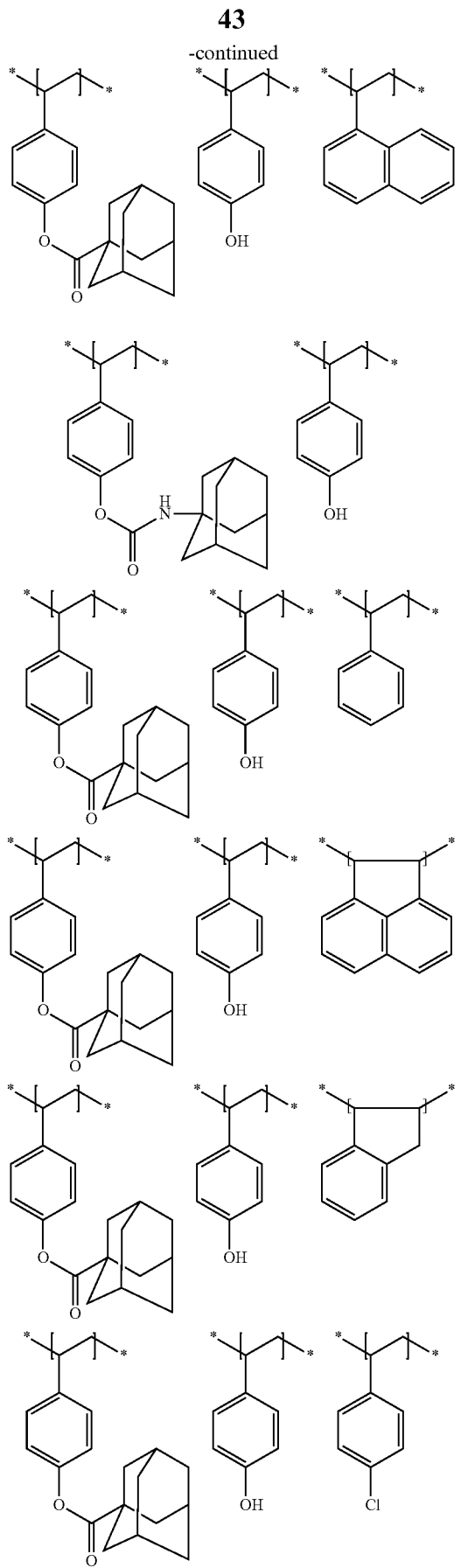
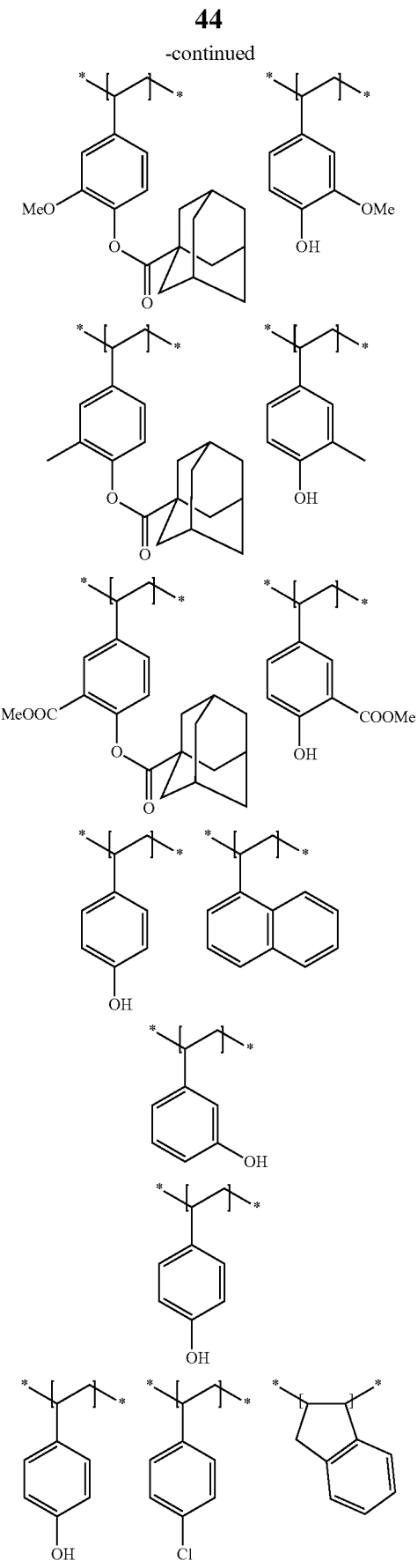

<Compound (B) that Generates Acid by Irradiation with Active Light or Radiation>

The composition of the present invention can contain a compound that generates an acid by irradiation with active light or radiation (hereinafter, also referred to as an "compound (B)", an "acid generator", or a "photoacid generator").

As a preferable aspect of the acid generator, an onium salt compound can be exemplified. Examples of such an onium salt compound include a sulfonium salt, an iodonium salt, and a phosphonium salt.

In addition, as another preferable aspect of the acid generator, a compound that generates sulfonic acid, imidic acid, or methide acid by irradiation with active light or radiation can be exemplified. Examples of the acid generator in the form include a sulfonium salt, an iodonium salt, a phosphonium salt, oxime sulfonate, and imidosulfonate.

The acid generator which can be used in the present invention is not limited to a low molecular weight compound, and a compound obtained by introducing a group that generates an acid by irradiation with active light or radiation into the main chain or a side chain of a polymer compound can also be used.

The acid generator is preferably a compound that generates an acid by irradiation with an electron beam or extreme ultraviolet rays.

In the present embodiment, examples of a preferable onium salt compound include a sulfonium compound represented by the following General Formula (7) and an iodonium compound represented by General Formula (8).

(7)

(8)

In General Formulas (7) and (8), Each of $R_{a1}$, $R_{a2}$, $R_{a3}$, $R_{a4}$, and $R_{a5}$ independently represents an organic group.

$X^-$ represents an organic anion.

The sulfonium compound represented by General Formula (7) and the iodonium compound represented by General Formula (8) are described in more detail below.

Each of $R_{a1}$, $R_{a2}$, and $R_{a3}$ in General Formula (7) and $R_{a4}$ and $R_{a5}$ in General Formula (8), as described above, independently represents an organic group, and preferably, at least one of $R_{a1}$, $R_{a2}$, and $R_{a3}$, and at least one of $R_{a4}$ and $R_{a5}$ is an aryl group, respectively. The aryl group is preferably a phenyl group or a naphthyl group, and more preferably a phenyl group.

Examples of the organic anion represented by $X^-$ in General Formulas (7) and (8) include a sulfonate anion, a carboxylate anion, a bis(alkylsulfonyl)amide anion, and a tris(alkylsulfonyl)methide anion, and the organic anion is preferably an organic anion represented by the following General Formula (9), (10), or (11), and more preferably an organic anion represented by the following General Formula (9).

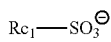

(9)

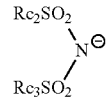

(10)

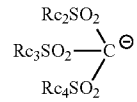

(11)

In General Formulas (9), (10), and (11), each of $R_{c1}$, $R_{c2}$, $R_{c3}$, and $R_{c4}$ independently represents an organic group.

The organic anion represented by $X^-$ corresponds to a sulfonic acid, imidic acid, methide acid, or the like which is an acid generated by active light or radiation such as an electron beam or extreme ultraviolet rays.

Examples of the organic group represented by each of $R_{c1}$, $R_{c2}$, $R_{c3}$, and $R_{c4}$ include an alkyl group, an aryl group, and a group obtained by connecting a plurality of these. Among these organic groups, an alkyl group in which the 1 position has been substituted with a fluorine atom or a fluoroalkyl group or a phenyl group substituted with a fluorine atom or a fluoroalkyl group is more preferable. By having a fluorine atom or a fluoroalkyl group, the acidity of the acid generated by irradiation with light is increased, and the sensitivity is improved. The terminal group preferably does not contain a fluorine atom as a substituent.

In the present invention, the compound (B) is preferably a compound that generates an acid (more preferably sulfonic acid) having a volume of 130 Angstrom$^3$ or greater, more preferably a compound that generates an acid (more preferably sulfonic acid) having a volume of 190 Angstrom$^3$ or greater, still more preferably a compound that generates an acid (more preferably sulfonic acid) having a volume of 270 Angstrom$^3$ or greater, and particularly preferably a compound that generates an acid (more preferably sulfonic acid) having a volume of 400 Angstrom$^3$ or greater, from the viewpoint of suppressing diffusion of the exposed acid to the unexposed portion and improving resolution or a pattern shape. Here, from the viewpoint of sensitivity and coating solvent solubility, the volume is preferably 2000 Angstrom$^3$ or less, and more preferably 1500 Angstrom$^3$ or less. The volume value is determined by using "WinMOPAC" manufactured by FUJITSU. That is, first, the chemical structure of the acid according to each compound is input, then, using this structure as an initial structure, the most stable conformation of each acid is determined by molecular force field calculation using an MM3 method, and then, by performing molecular orbital calculation using a PM3 method on these most stable conformations, the "accessible volume" of each acid can be calculated.

In the present invention, particularly preferable acid generators are exemplified below. Calculated volume values are given to some examples (unit Angstrom$^3$). Moreover, the calculated value determined here is a volume value of an acid in which a proton is bonded to the anionic portion.

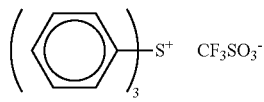

(z1)

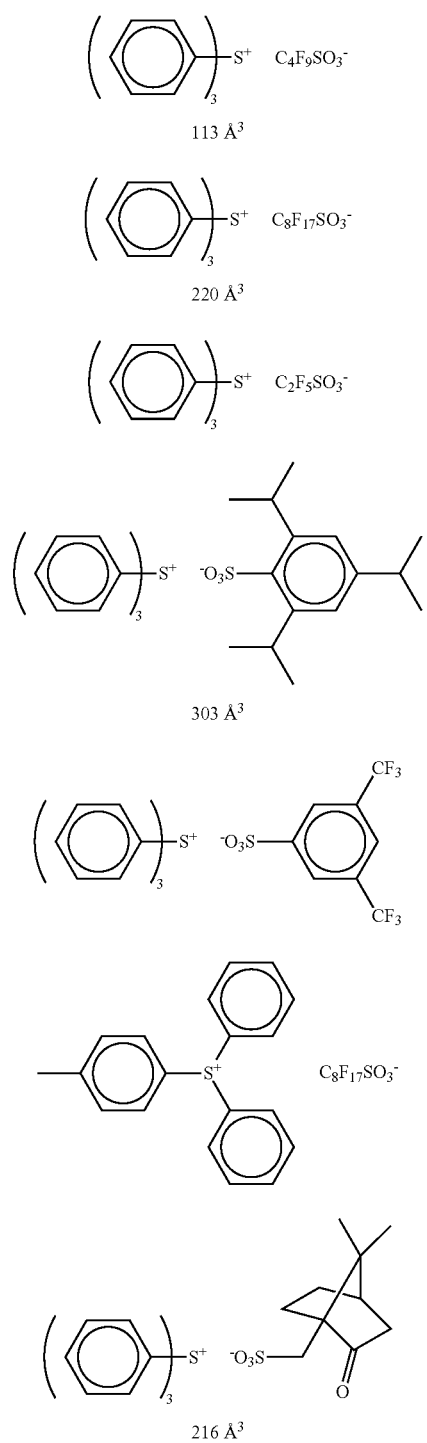
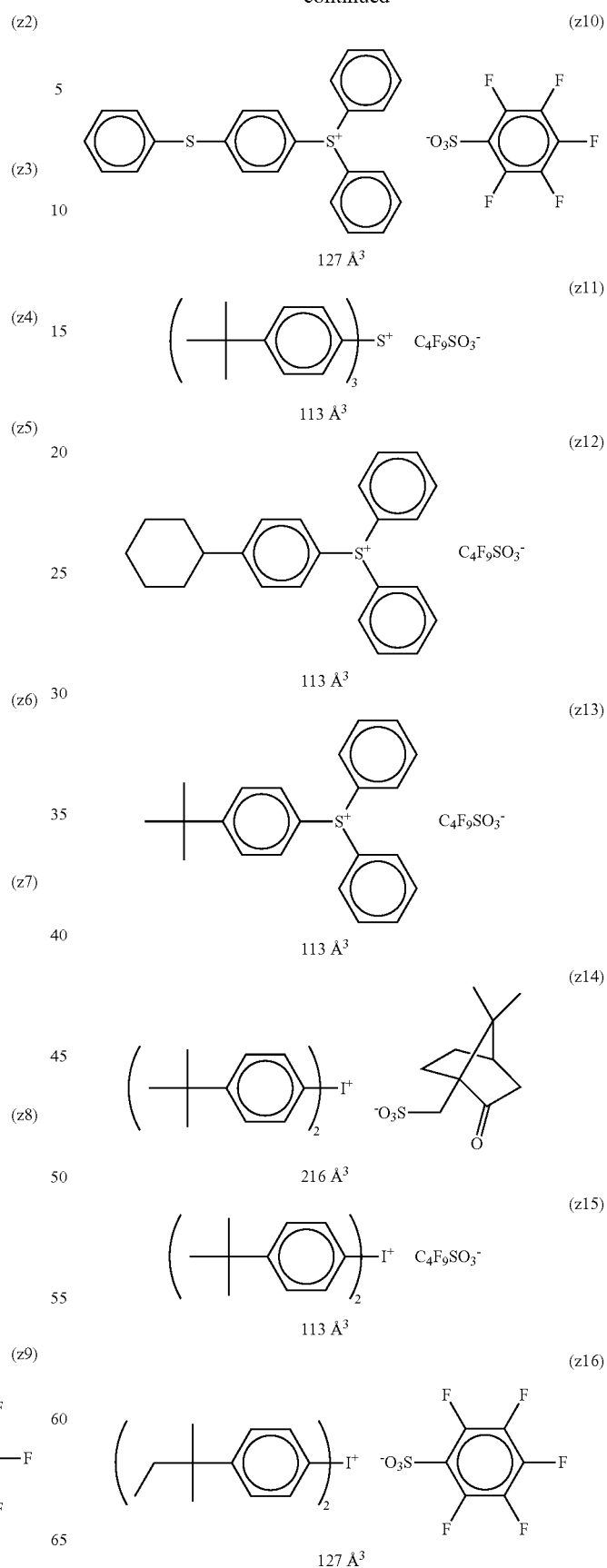

-continued
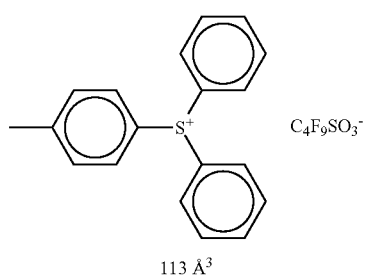
(z17)
113 Å³
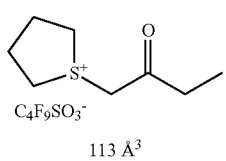 (z18)
113 Å³
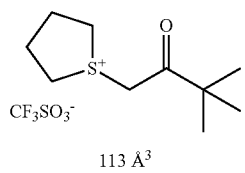 (z19)
113 Å³
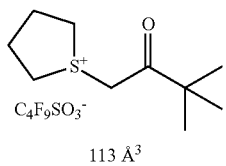 (z20)
113 Å³
 (z21)
113 Å³
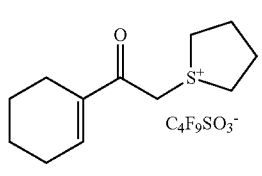 (z22)
113 Å³
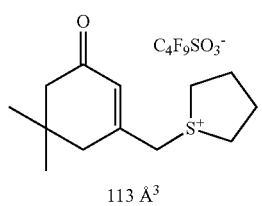 (z23)
113 Å³
-continued
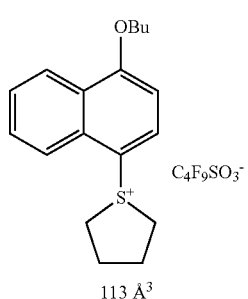 (z24)
113 Å³
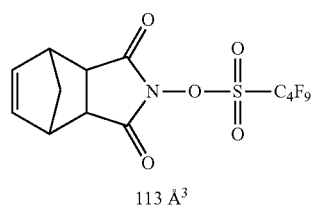 (z25)
113 Å³
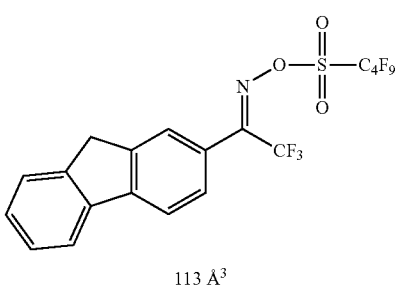 (z26)
113 Å³
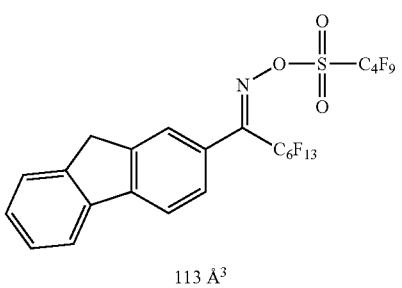 (z27)
113 Å³
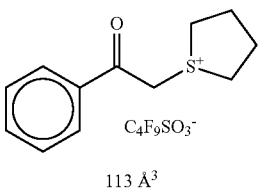 (z28)
113 Å³
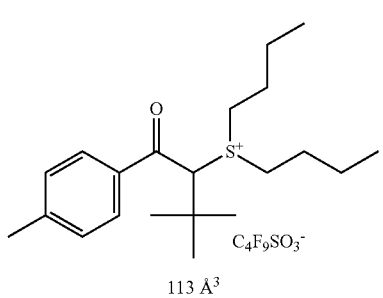 (z29)
113 Å³

-continued
(z30)
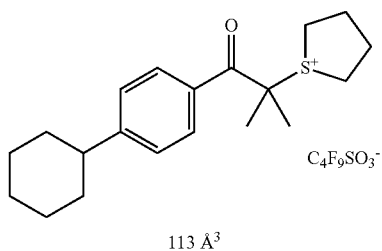
C₄F₉SO₃⁻
113 Å³
(z31)
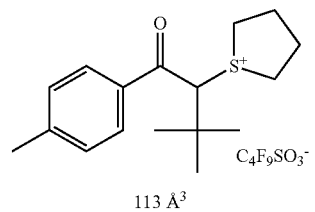
C₄F₉SO₃⁻
113 Å³
(z32)
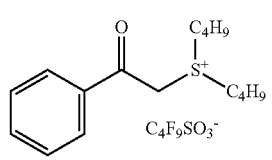
C₄F₉SO₃⁻
113 Å³
(z33)
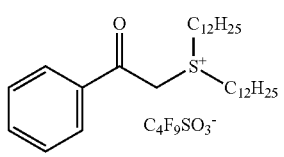
C₄F₉SO₃⁻
113 Å³
(z34)
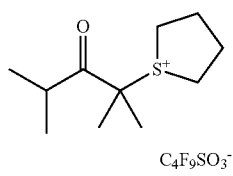
C₄F₉SO₃⁻
113 Å³
(z35)
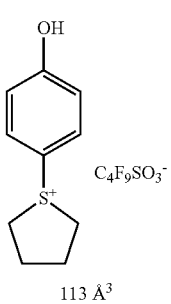
C₄F₉SO₃⁻
113 Å³
(z36)
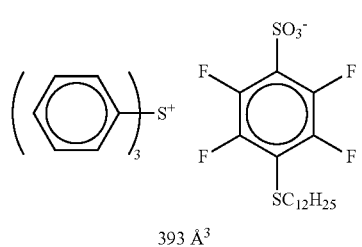
393 Å³
-continued
(z37)
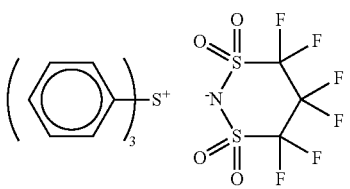
136 Å³
(z38)
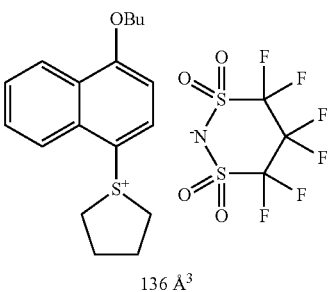
136 Å³
(z40)
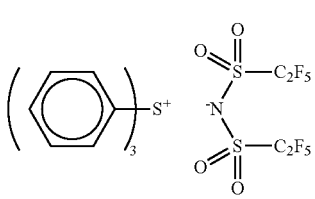
173 Å³
(z42)
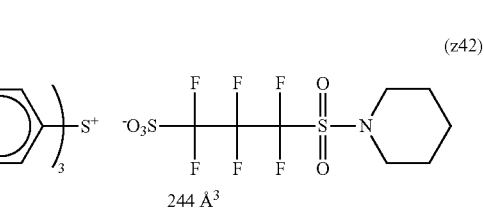
244 Å³
(z43)
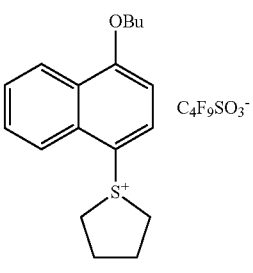
C₄F₉SO₃⁻
113 Å³
(z44)
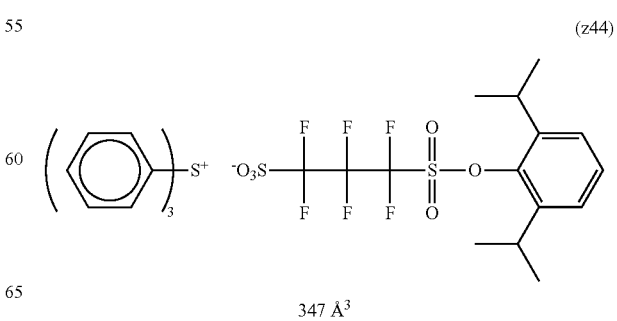
347 Å³

(z45)
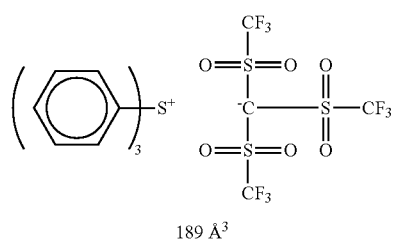
189 Å³
(z46)
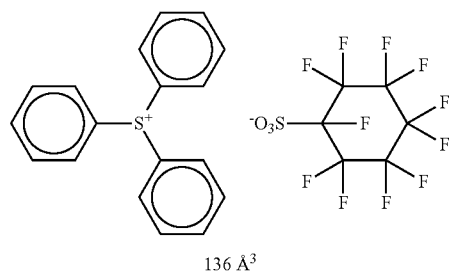
136 Å³
(z47)
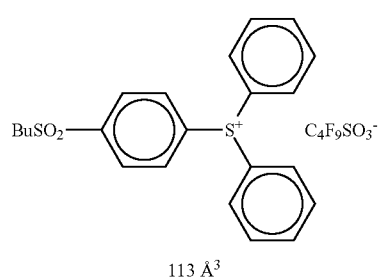
113 Å³
(z48)
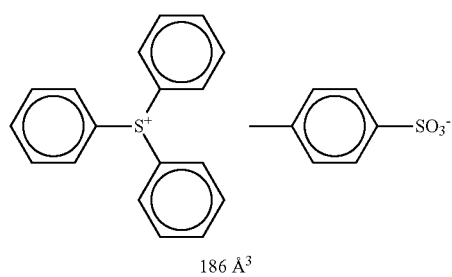
186 Å³
(z49)
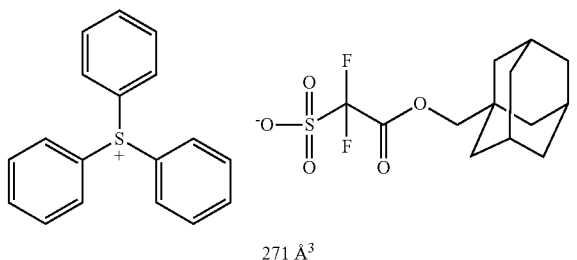
271 Å³
(z50)
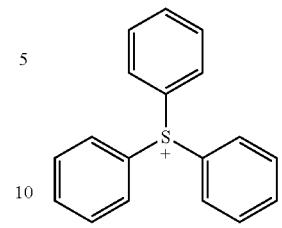
291 Å³
(z51)
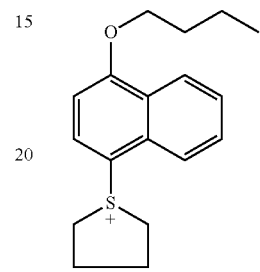
271 Å³
(z52)
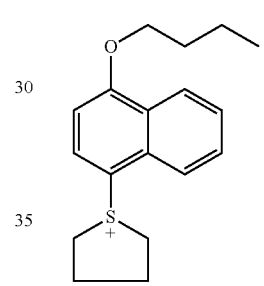
244 Å³
(z53)
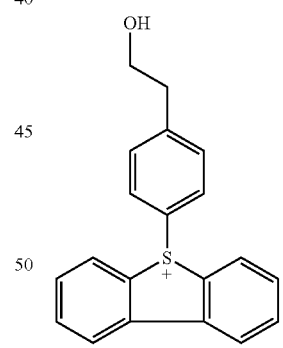
437 Å³
(z54)
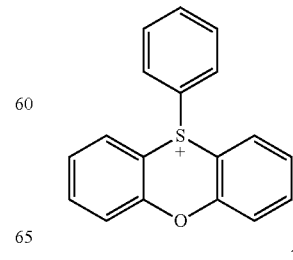
303 Å³

(z55)
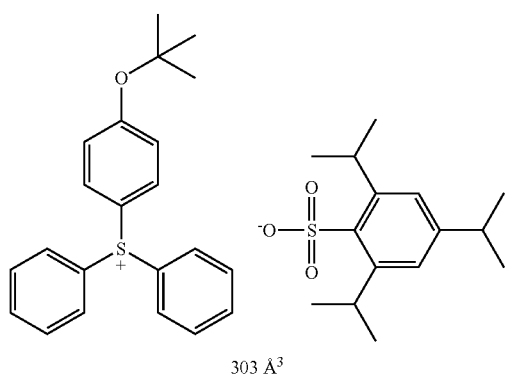
303 Å³
(z56)
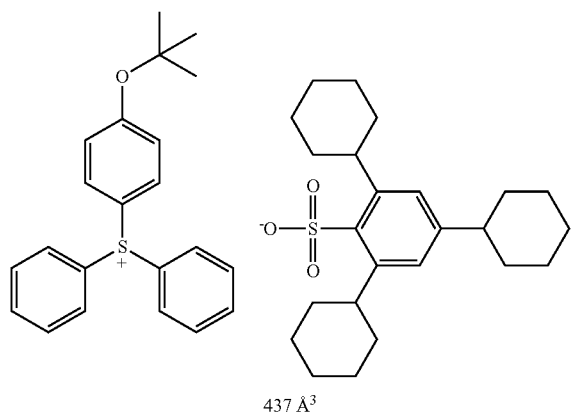
437 Å³
(z57)
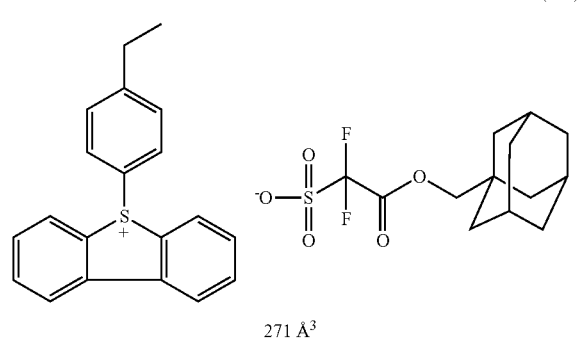
271 Å³
(z58)
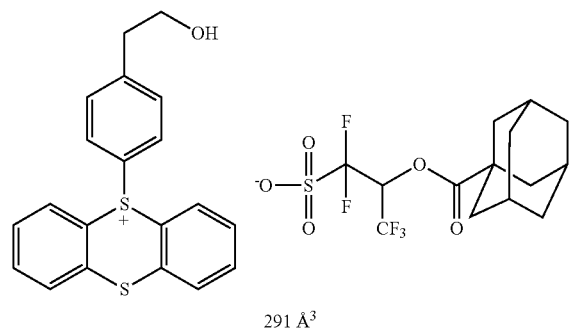
291 Å³
(z59)
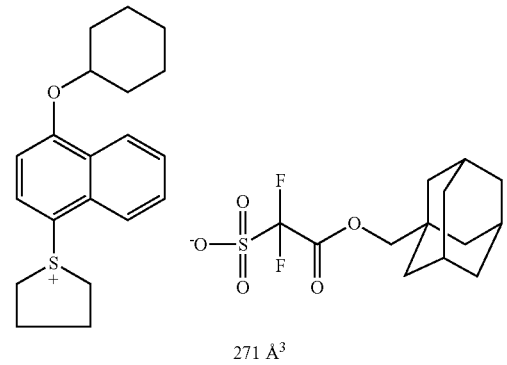
271 Å³
(z60)
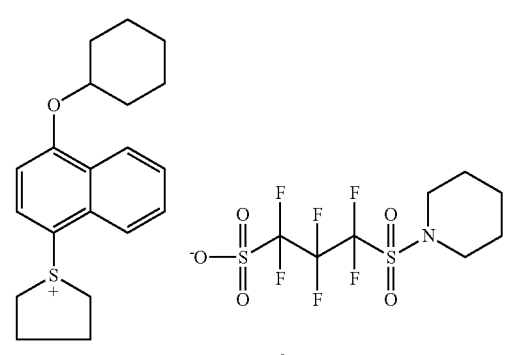
244 Å³
(z61)
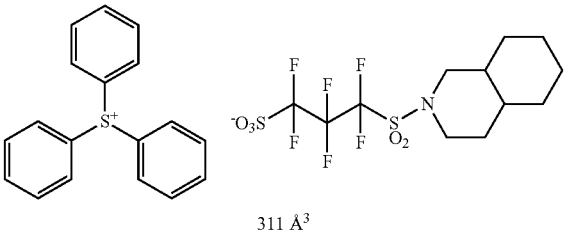
311 Å³
(z62)
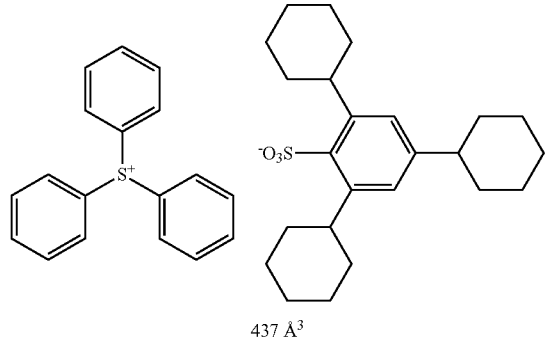
437 Å³

-continued (z63)

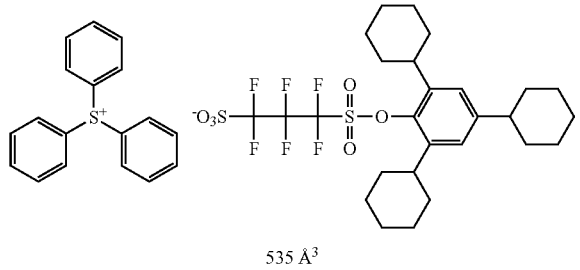

535 Å³

(z64)

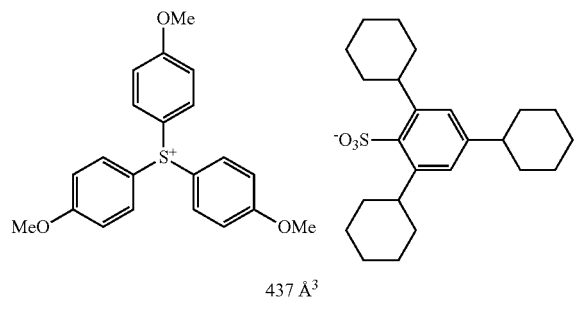

437 Å³

(z65)

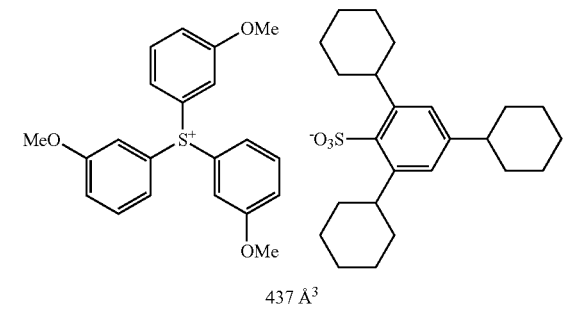

437 Å³

(z66)

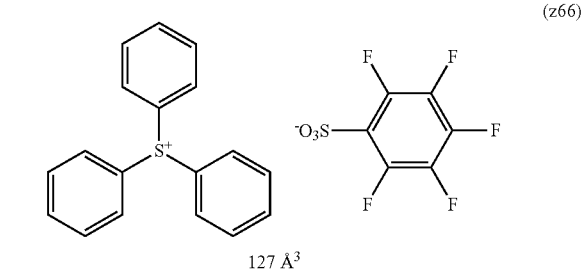

127 Å³

(z67)

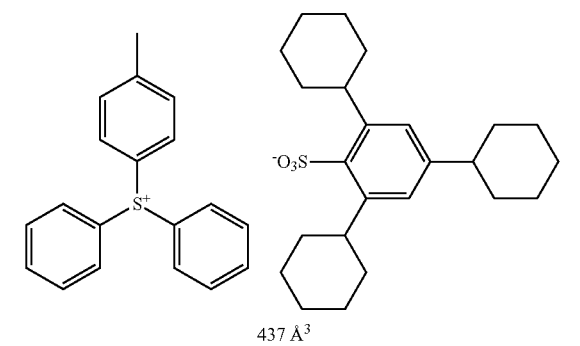

437 Å³

-continued (z68)

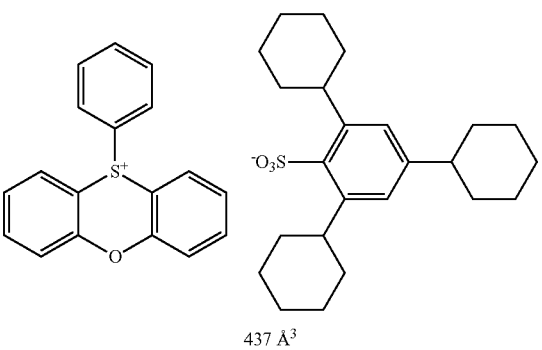

437 Å³

In addition, as the acid generator (preferably, an onium compound) used in the present invention, a polymer type acid generator obtained by introducing a group (photoacid generating group) that generates an acid by irradiation with active light or radiation into the main chain or a side chain of a polymer compound can also be used.

The content of the acid generator in the composition is preferably 0.1% by mass to 35% by mass, more preferably 1% by mass to 20% by mass, and still more preferably 2% by mass to 15% by mass, based on the total solid content of the composition.

The acid generator can be used alone, or two or more types thereof can be used in combination.

<Compound (C') having Acid Cross-Linking Group other than Cross-Linking Agent (C)>

The composition of the present invention may further contain a compound (C') (hereinafter, also referred to as a "compound (C')" or an "cross-linking agent (C')") having an acid cross-linking group other than the cross-linking agent (C). The compound (C') is preferably a compound including two or more of hydroxymethyl groups or alkoxymethyl groups in the molecule, which is a compound other than the cross-linking agent (C) represented by General Formula (1-0). In addition, the compound (C) preferably contains a methylol group from the viewpoint of LER improvement.

First, a case where the compound (C') (hereinafter, referred to as a compound (C'1)) is a low molecular compound will be described. Preferable examples of the compound (C'1) include a hydroxymethylated or alkoxymethylated phenol compound, an alkoxymethylated melamine-based compound, an alkoxymethyl glycoluril-based compound, and an alkoxymethylated urea-based compound. As a particularly preferable compound (C'1), a phenol derivative or an alkoxymethyl glycoluril derivative having a molecular weight of 1200 or less, which includes three to five benzene rings in the molecule, and further has two or more combined hydroxymethyl groups or alkoxymethyl groups is exemplified.

The alkoxymethyl group is preferably a methoxymethyl group or a ethoxymethyl group.

Among the examples of the compound (C'1), the phenol derivative having a hydroxymethyl group can be obtained by reacting a phenol compound which does not have a corresponding hydroxymethyl group with formaldehyde in the presence of a base catalyst. In addition, the phenol derivative having an alkoxymethyl group can be obtained by reacting a phenol derivative which has a corresponding hydroxymethyl group with an alcohol in the presence of an acid catalyst.

As other preferable compounds (C'1), a compound having an N-hydroxymethyl group or an N-alkoxymethyl group such as an alkoxymethylated melamine-based compound, an alkoxymethyl glycoluril-based compound, or an alkoxymethylated urea-based compound can be exemplified.

Examples of such a compound include hexamethoxymethyl melamine, hexaethoxymethyl melamine, tetramethoxymethyl glycoluril, 1,3-bismethoxymethyl-4,5-bis-methoxyethylene urea, and bismethoxymethyl urea, and the compound is disclosed in EP0,133,216A, DE3,634,671A, DE3,711,264A, and EP0,212,482A.

Particularly preferable examples among specific examples of the compound (C'1) are shown below.

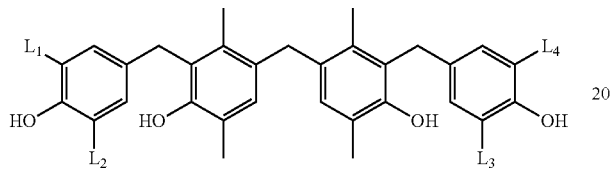

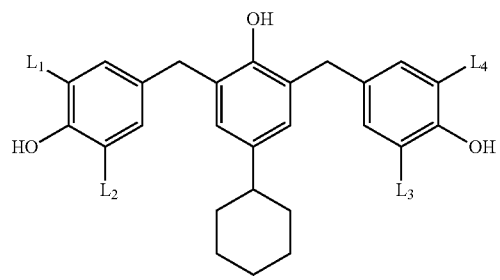

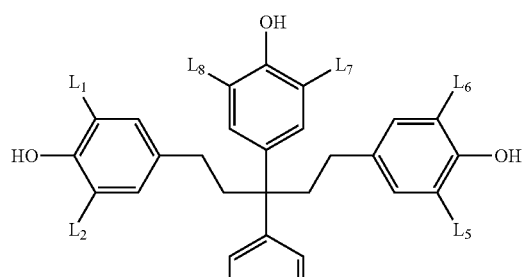

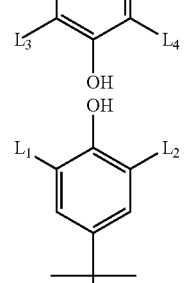

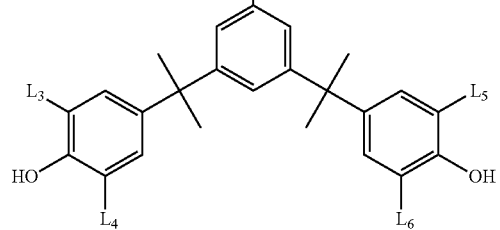

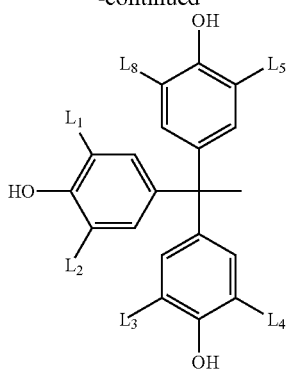

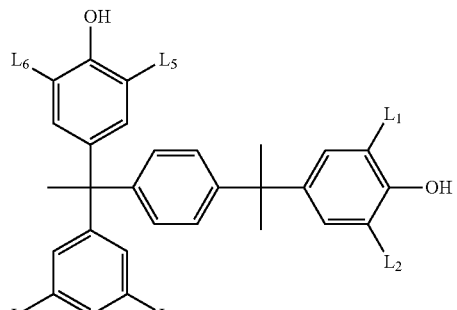

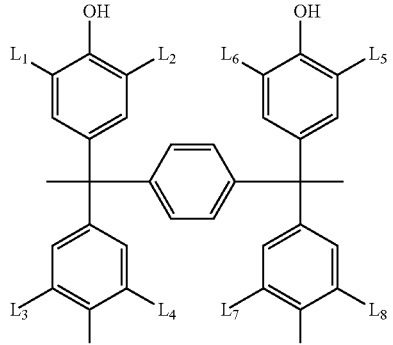

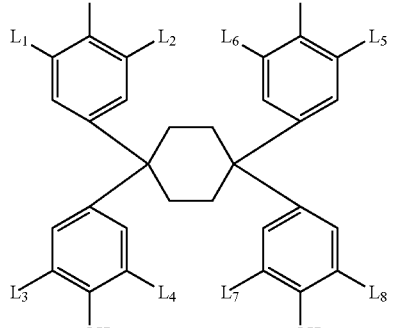

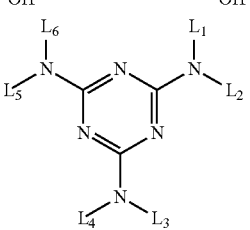

-continued

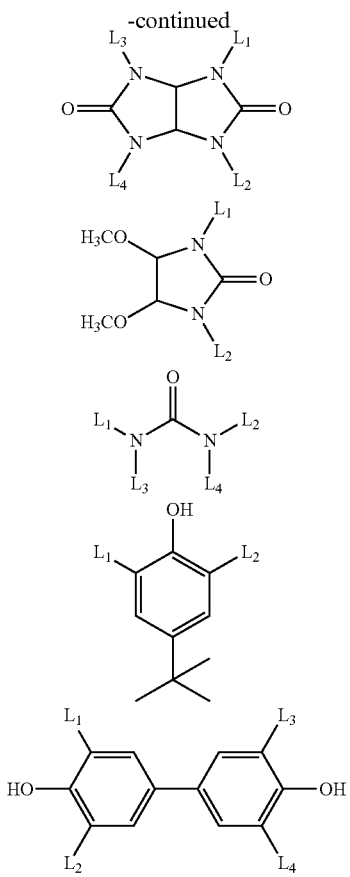

In the formula, each of $L_1$ to $L_8$ independently represents a hydrogen atom, a hydroxymethyl group, a methoxymethyl group, an ethoxymethyl group, or an alkyl group having 1 to 6 carbon atoms.

In the present invention, the content of the compound (C'1) is preferably 0% by mass to 20% by mass and more preferably 0% by mass to 10% by mass, in the total solid content of the active light sensitive or radiation sensitive resin composition. When the content of the compound (C'1) is within a range of 0% by mass to 20% by mass, reduction of the residual film ratio and the resolving power is prevented, and stability of the composition of the present invention during storage is favorably maintained.

In the present invention, the compound (C'1) may be used alone, or two or more types thereof may be used in combination. The compound (C'1) is preferably used in combination of two or more types thereof from the viewpoint of a good pattern shape.

For example, in the case of using in combination with another compound (C'1), for example, a compound having the N-alkoxymethyl group, in addition to the phenol derivative described above, the ratio between the phenol derivative and the another compound (C') is typically 90/10 to 20/80, preferably 85/15 to 40/60, and more preferably 80/20 to 50/50, in a molar ratio.

The compound (C'1) including an acid cross-linking group may be an aspect of a resin (hereinafter, also referred to as a compound (C'2)) including a repeating unit having an acid cross-linking group. In the case of such an aspect, the cross-linking group is included in a molecular unit of the repeating unit, and due to this, the cross-linking reactivity is high compared to a typical system of resin+cross-linking agent. Thus, it is possible to form a hard film, and it is possible to control the diffusibility of an acid and dry etching resistance. As a result, the diffusibility of an acid in the exposed portion to active light or radiation such as an electron beam or extreme ultraviolet rays is extremely suppressed, and as a result, the resolving power, a pattern shape, and LER of a fine pattern are improved. In addition, in a case where the reaction point of a resin and the reaction point of a cross-linking group are in close proximity, as a repeating unit represented by the following General Formula (1), a composition of which the sensitivity during pattern formation has been improved is obtained.

Examples of the compound (C'2) include a resin including a repeating unit represented by the following General Formula (1). The repeating unit represented by General Formula (1) has a structure including at least one methylol group which may have a substituent.

Here, the "methylol group" is a group represented by the following General Formula (M), and in one embodiment of the present invention, is preferably a hydroxymethyl group or an alkoxymethyl group.

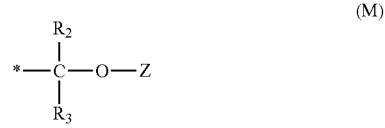

(M)

In the formula, $R_2$, $R_3$, and Z have the same definition as those in General Formula (1) described below, respectively.

First, General Formula (1) will be described.

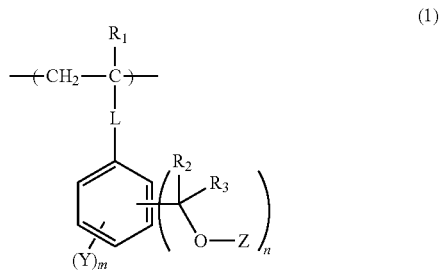

(1)

In General Formula (1), $R^1$ represents a hydrogen atom, a methyl group, or a halogen atom.

Each of $R_2$ and $R_3$ represents a hydrogen atom, an alkyl group, or a cycloalkyl group.

L represents a divalent connecting group or single bond.

Y represents a substituent excluding a methylol group.

Z represents a hydrogen atom or a substituent.

m represents an integer of 0 to 4.

n represents an integer of 1 to 5.

m+n is 5 or less.

In a case where m is 2 or greater, a plurality of Y's may be the same as or may be different from each other.

In a case where n is 2 or greater, a plurality of $R_2$'s, $R_3$'s, and Z's may be the same as or may be different from each other.

In addition, two or more of Y, $R_2$, $R_3$, and Z may be bonded to each other to form a ring structure.

Each of $R_1$, $R_2$, $R_3$, L, and Y may have a substituent.

In addition, when m is 2 or greater, a plurality of Y's may be bonded to each other to form a ring structure through a single bond or a connecting group.

In addition, the repeating unit represented by General Formula (1) is preferably represented by the following General Formula (2) or (3).

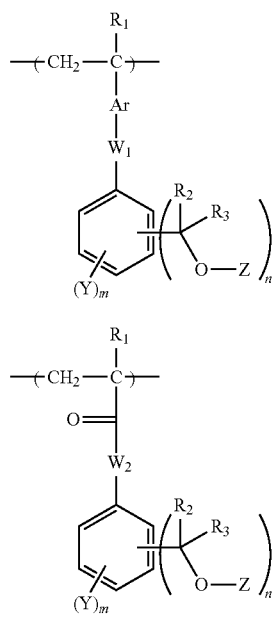

(2)

(3)

In General Formulas (2) and (3), $R_1$, $R_2$, $R_3$, Y, Z, m, and n have the same definition as those in General Formula (1), respectively.

Ar represents an aromatic ring.

Each of $W_1$ and $W_2$ represents a divalent connecting group or a single bond.

In addition, the repeating unit represented by General Formula (1) is more preferably represented by the following General Formula (2') or (3').

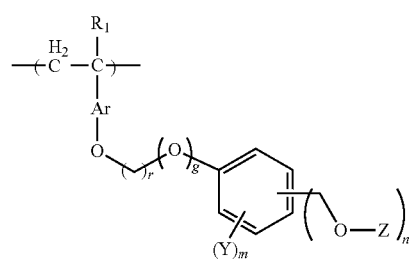

(2')

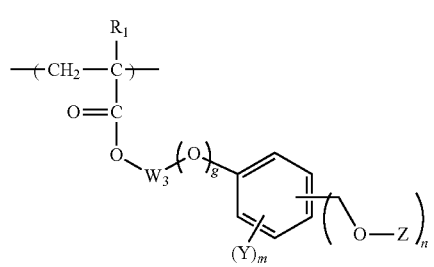

(3')

Each of $R_1$, Y, Z, m, and n in General Formulas (2') and (3') has the same meaning as each in General Formula (1). Ar in General Formula (2') has the same meaning as Ar in General Formula (2).

In General Formula (3'), $W_3$ represents a divalent connecting group.

In General Formulas (2') and (3'), f is an integer of 0 to 6.

In General Formulas (2') and (3'), g is 0 or 1.

In addition, General Formula (2') is particularly preferably represented by any one of the following General Formulas (1-a) to (1-c). The compound (C") particularly preferably includes a repeating unit represented by any one of the following General Formulas (1-a) to (1-c) or the repeating unit represented by General Formula (3').

(1-a)

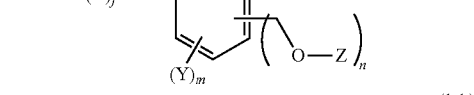

(1-b)

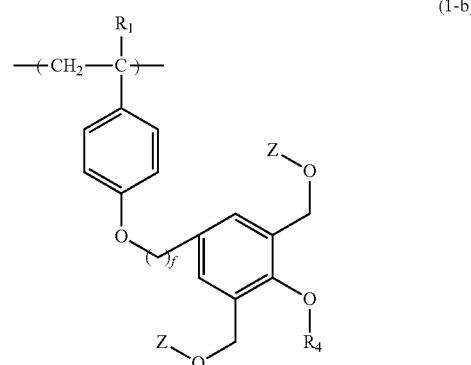

(1-c)

Each of $R_1$, Y, and Z in General Formulas (1-a) to (1-c) has the same meaning as each group in General Formula (1).

In General Formulas (1-b) and (1-c), Y" represents a hydrogen atom or a monovalent substituent. Here, Y" may be a methylol group.

$R_4$ represents a hydrogen atom or a monovalent substituent.

f represents an integer of 1 to 6.

m is 0 or 1, and n represents an integer of 1 to 3.

The content of the repeating unit having an acid crosslinking group in the compound (C'2) is preferably 3 mol % to 40 mol % and more preferably 5 mol % to 30 mol %, with respect to the entirety of repeating units of the compound (C'2).

The content of the compound (C'2) is preferably 0% by mass to 20% by mass and more preferably 0% by mass to 10% by mass, in the total solid content of the active light sensitive or radiation sensitive resin composition.

The compound (C'2) may include two or more types of repeating units having an acid cross-linking group, or two or more types of compounds (C'2) may be used in combination. In addition, the compound (C'1) and the compound (C'2) can also be used in combination.

Specific examples of the repeating unit having an acid cross-linking group included in the compound (C'2) include the following structures.

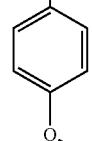
(Q-1)

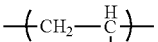
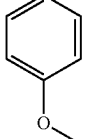
(Q-2)

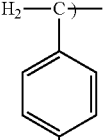
(Q-3)

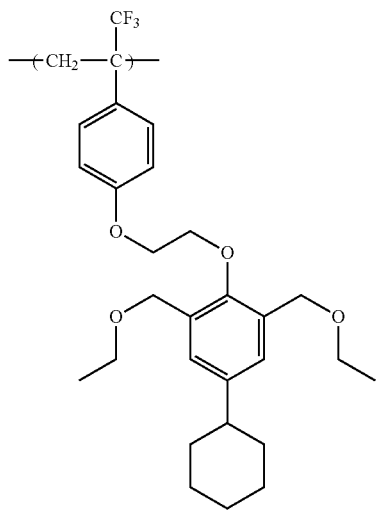
(Q-4)

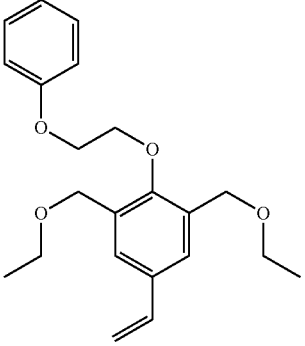
(Q-5)

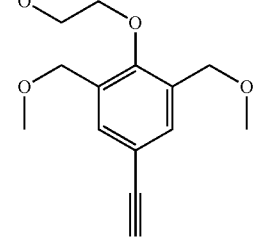
(Q-6)

-continued
(Q-7)
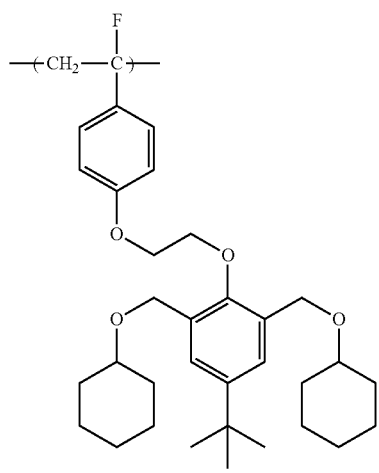
(Q-8)
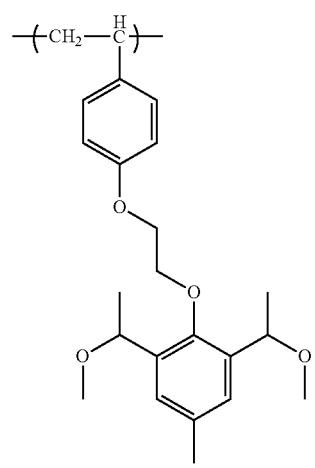
(Q-9)
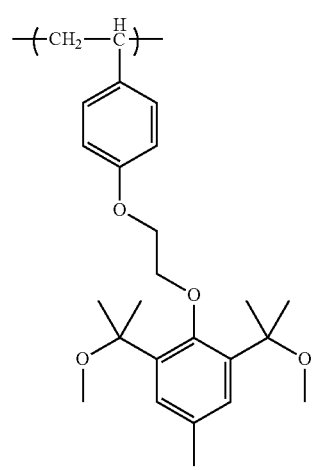
(Q-10)
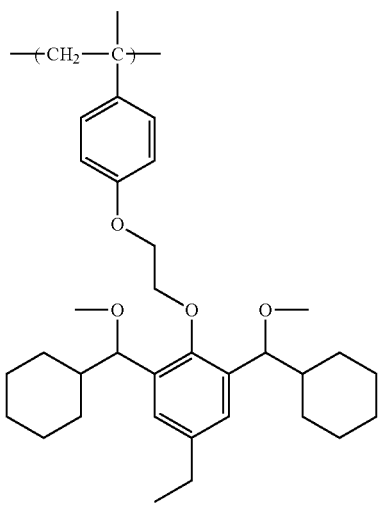
(Q-11)
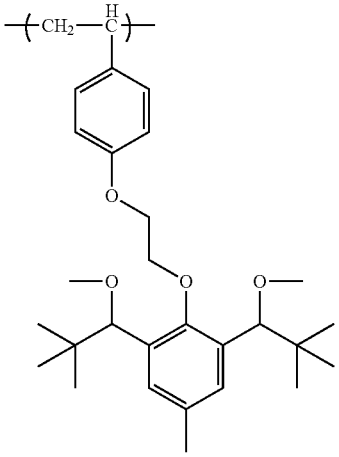
(Q-12)
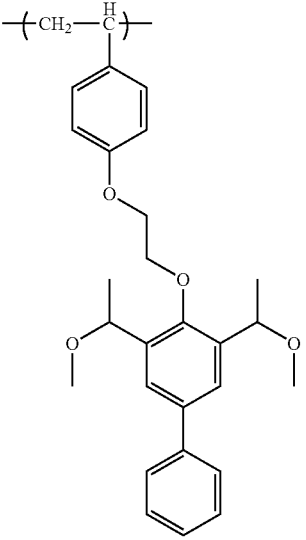

(Q-13)
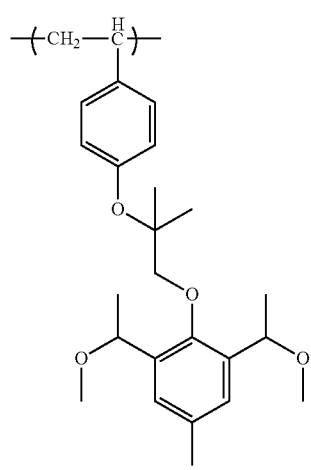
(Q-14)
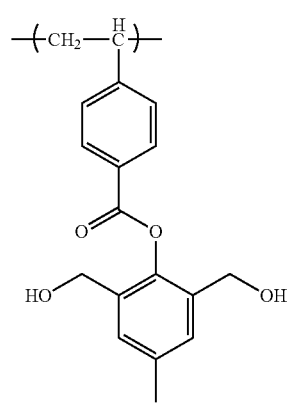
(Q-15)
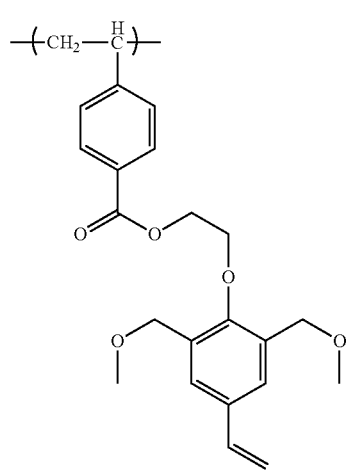
(Q-16)
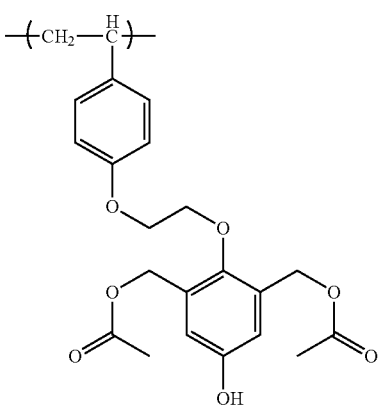
(Q-17)
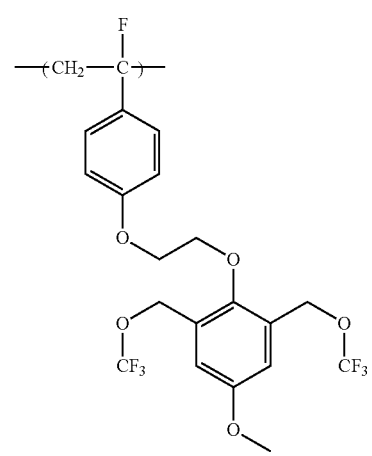
(Q-18)
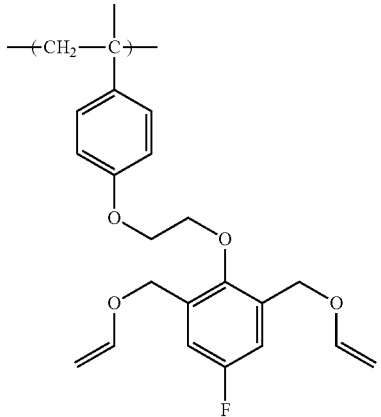

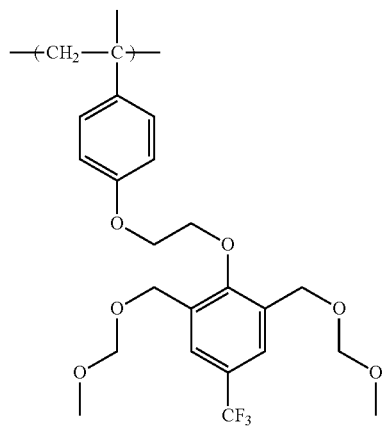
(Q-19)
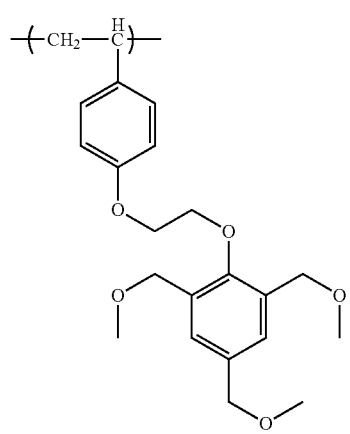
(Q-22)
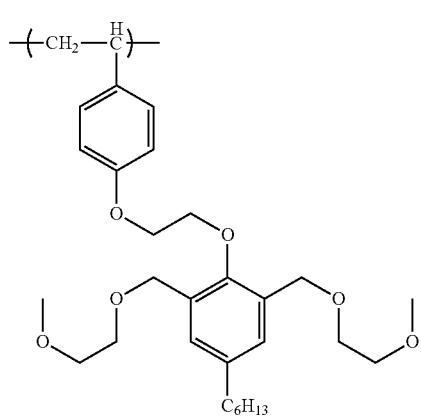
(Q-20)
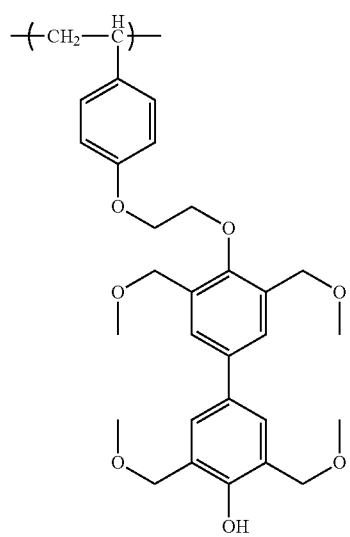
(Q-23)
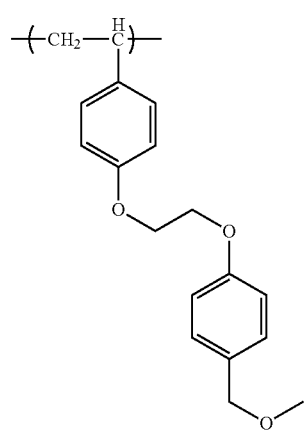
(Q-21)
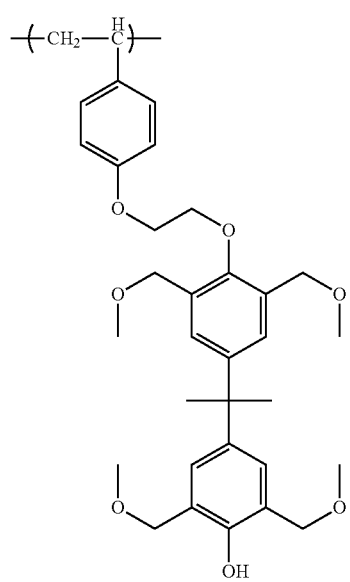
(Q-24)

(Q-25)
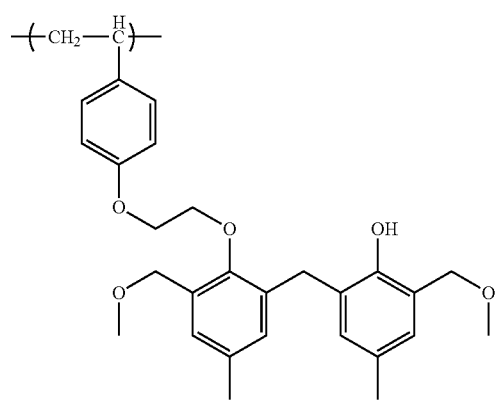
(Q-26)
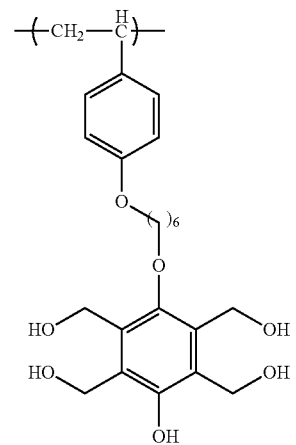
(Q-27)
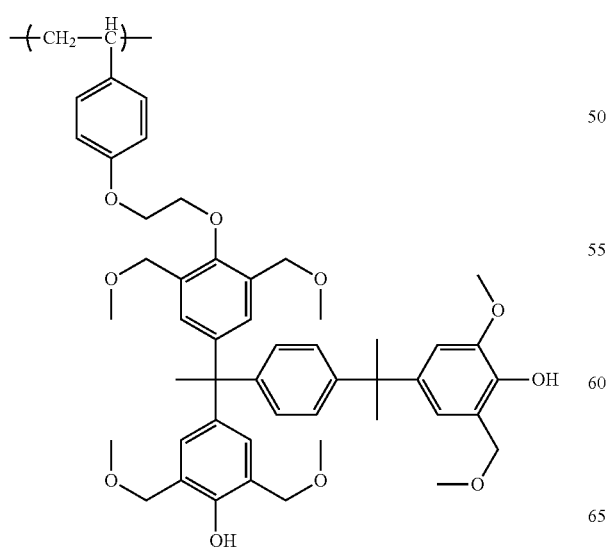
(Q-28)
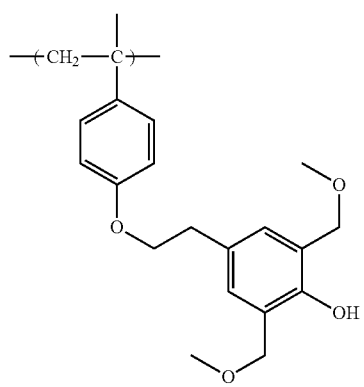
(Q-29)
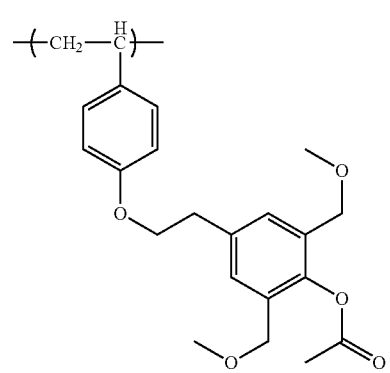
(Q-30)
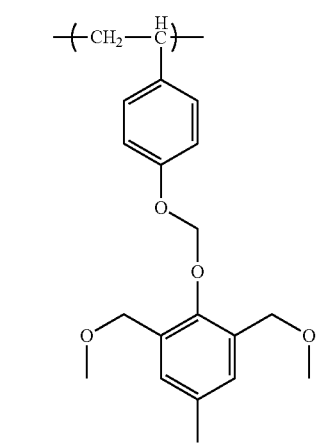
(Q-31)
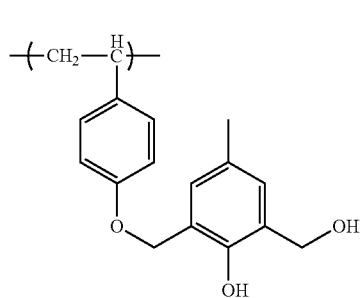

(Q-32)
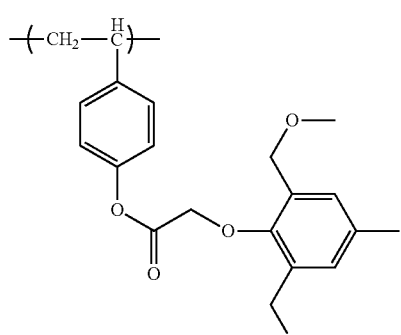
(Q-33)
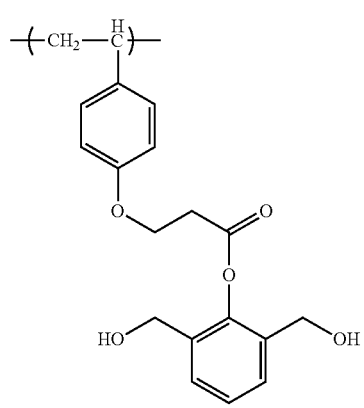
(Q-34)
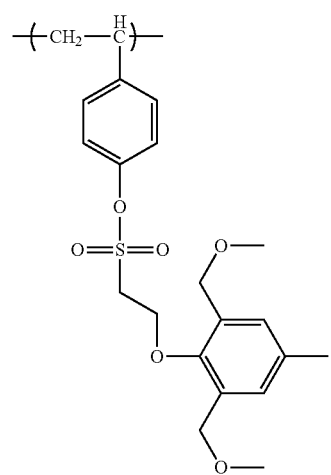
(Q-35)
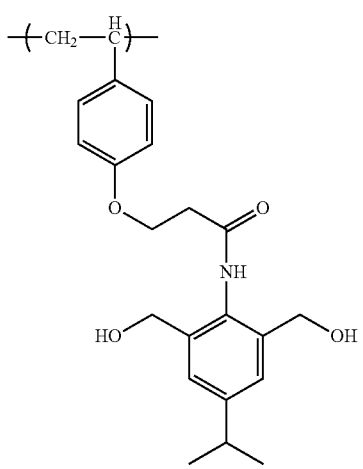
(Q-36)
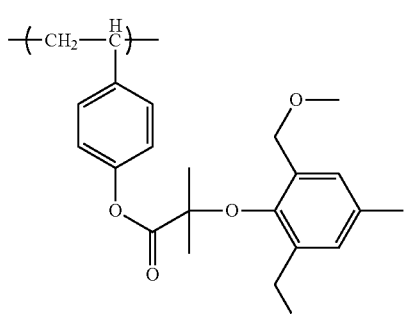
(Q-37)
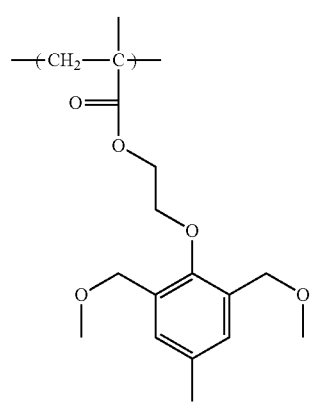
(Q-38)
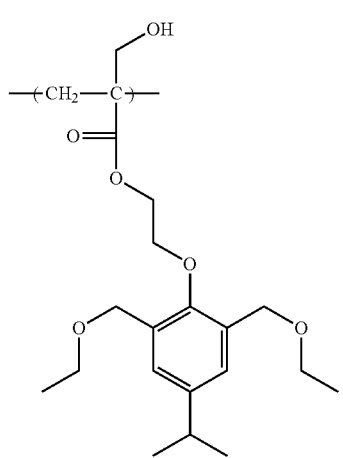

(Q-39) 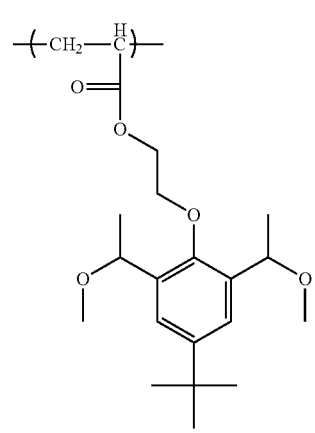
(Q-40) 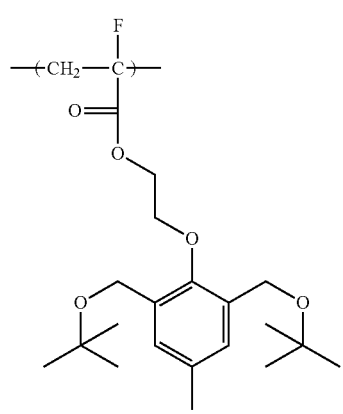
(Q-41) 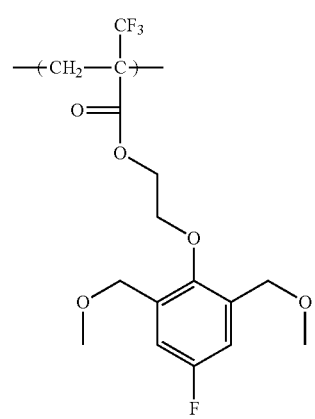
(Q-42) 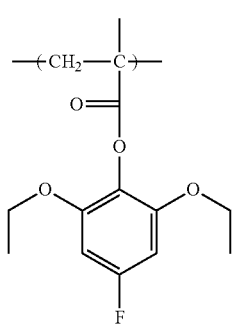
(Q-43) 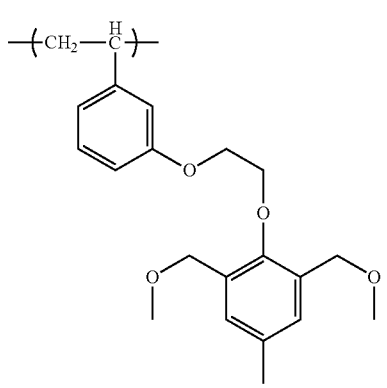
(Q-44) 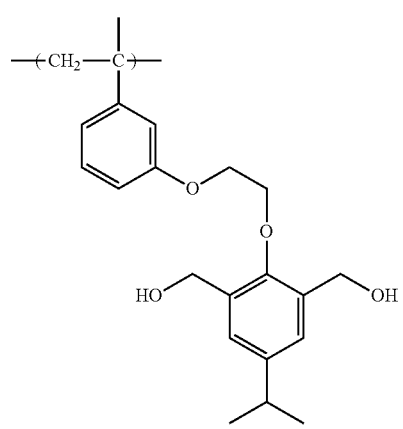
(Q-45) 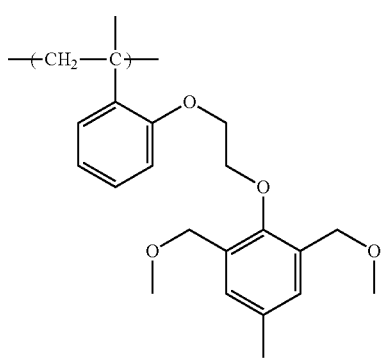
(Q-46) 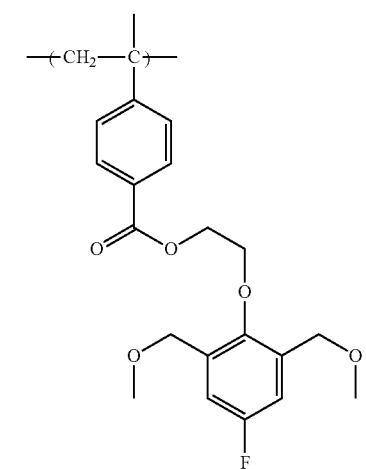

(Q-47)
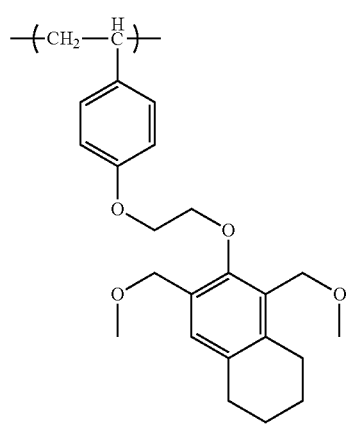
(Q-48)
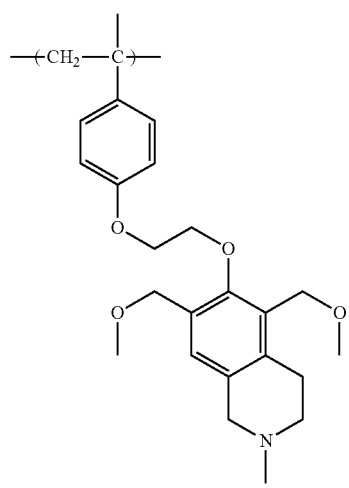
(Q-49)
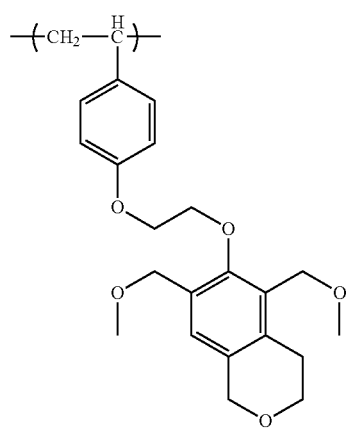
(Q-50)
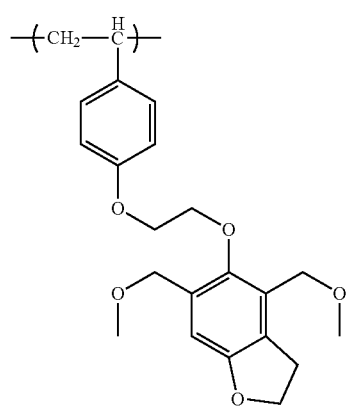
(Q-51)
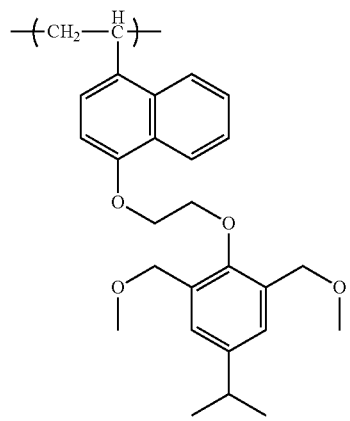
(Q-52)
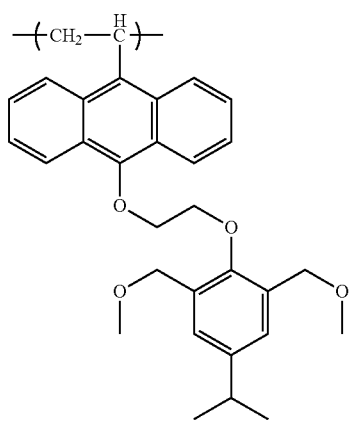

(Q-53)
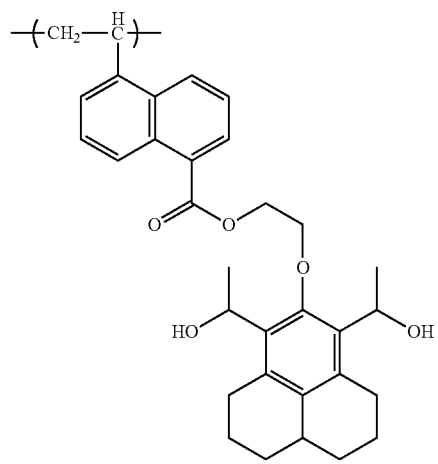
(Q-54)
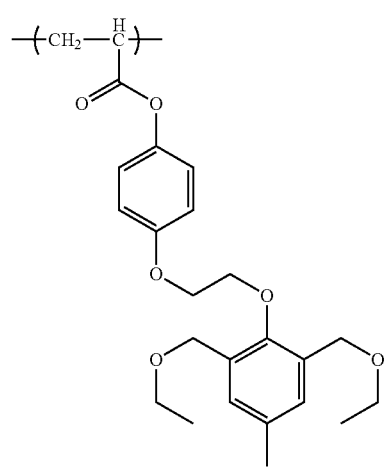
(Q-55)
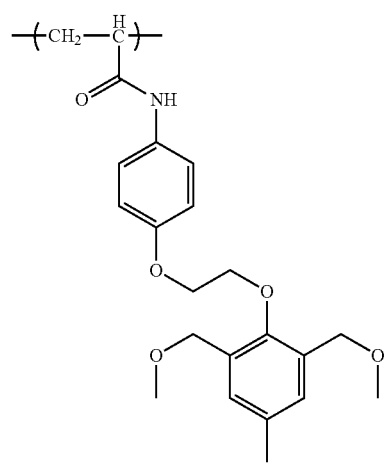
(Q-56)
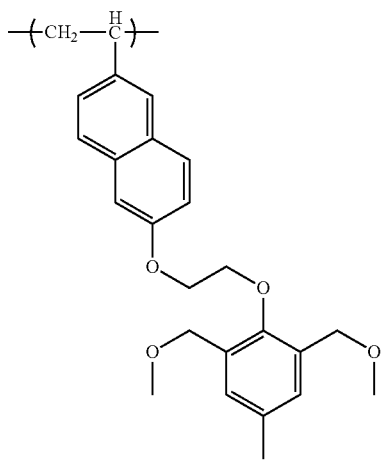
(Q-57)
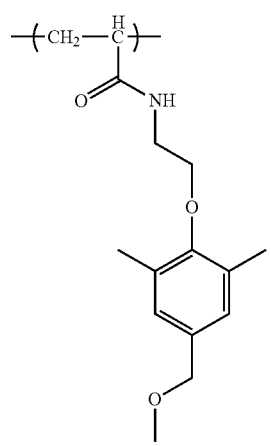
(Q-58)
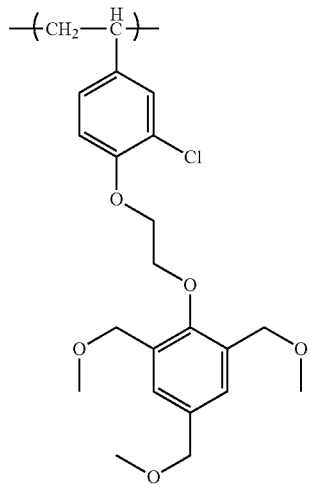

(Q-59)
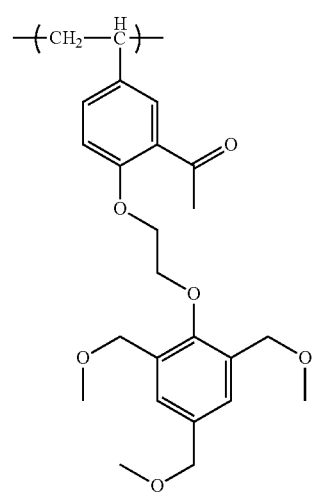
(Q-60)
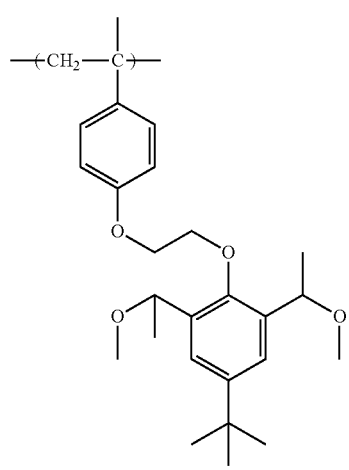
(Q-61)
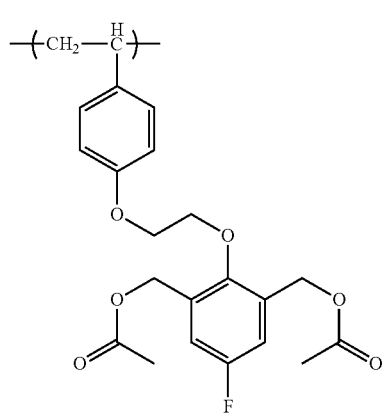
(Q-62)
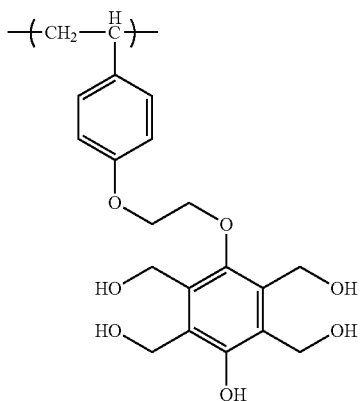
(Q-63)
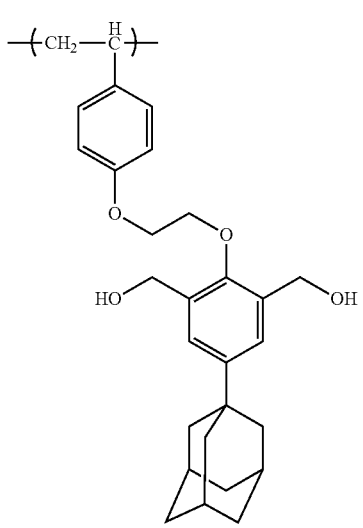
(Q-64)
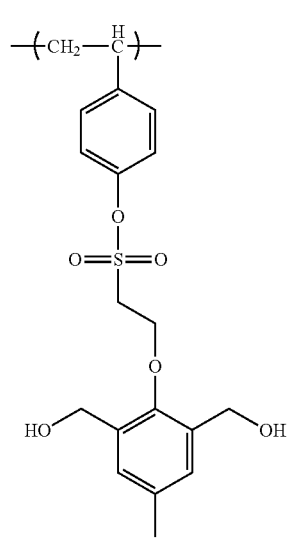

(Q-65)
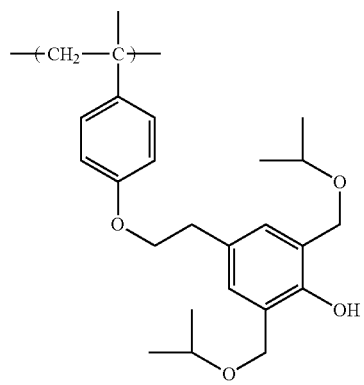
(Q-66)
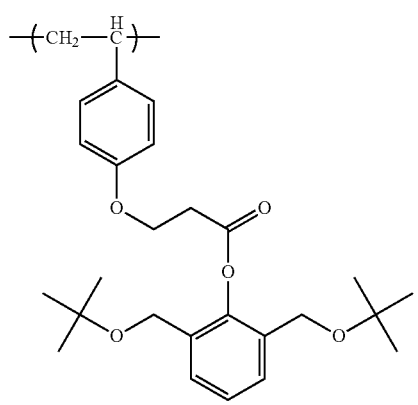
(Q-67)
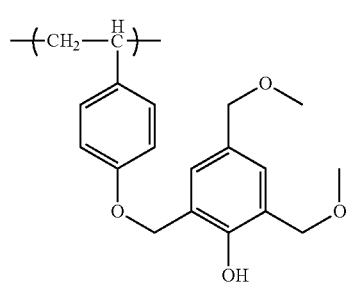
(Q-68)
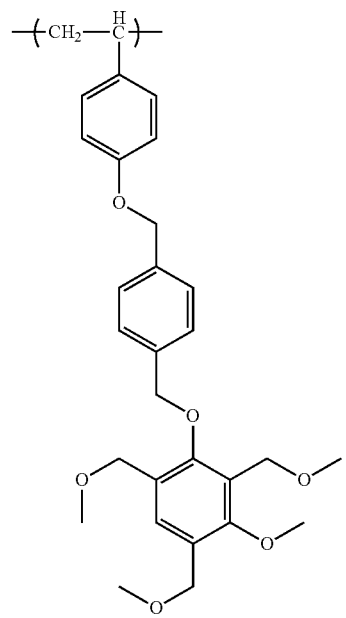
(Q-69)
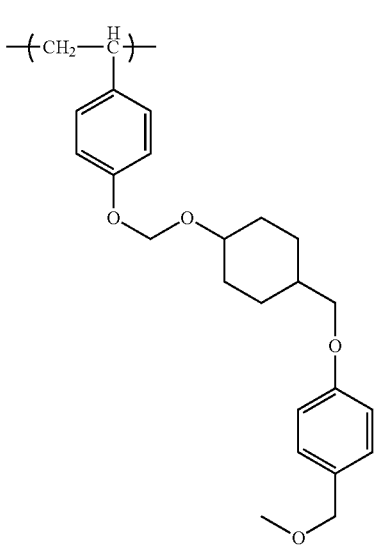
(Q-70)
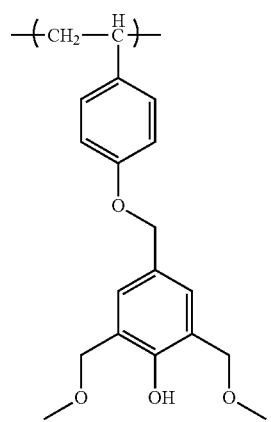

(Q-71)
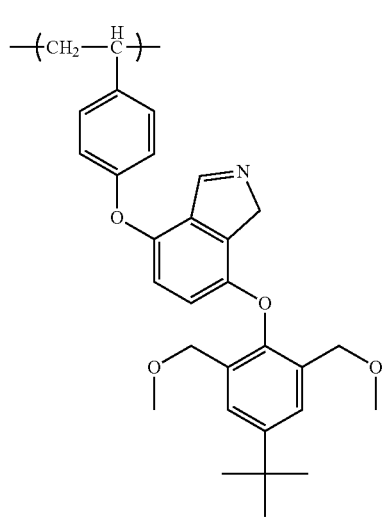
(Q-72)
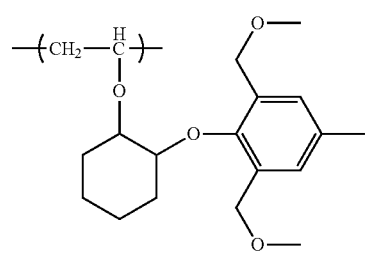
(Q-73)
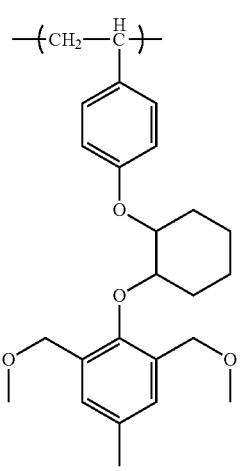
(Q-74)
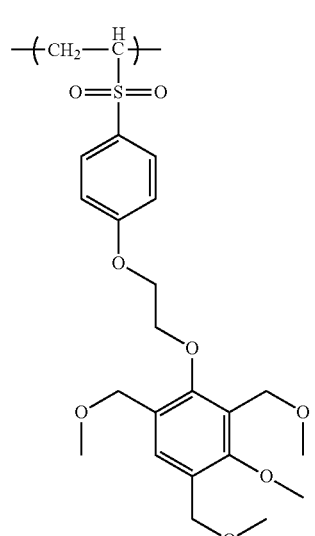
(Q-75)
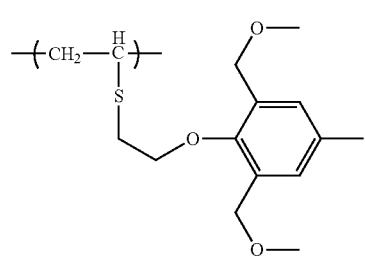
(Q-76)
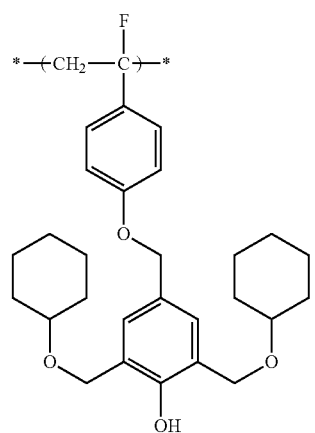
(Q-77)
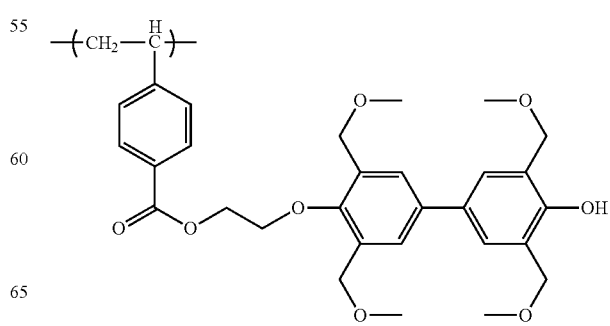

(Q-78) 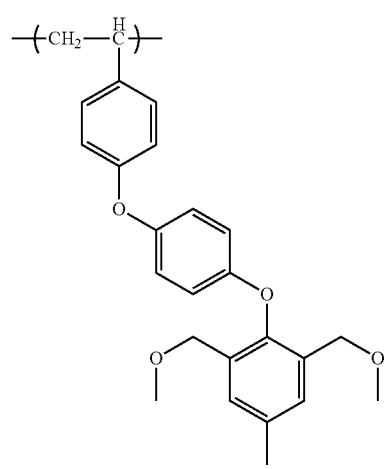
(Q-79) 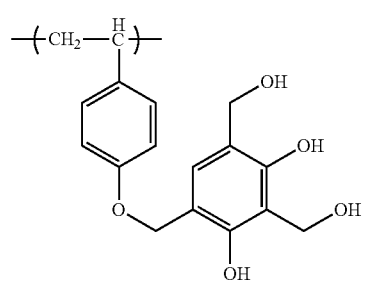
(Q-80) 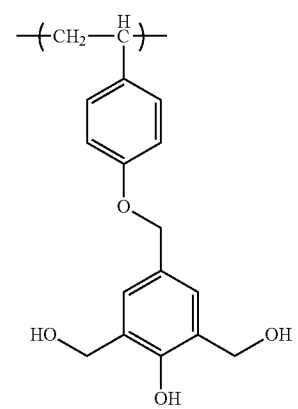
(Q-81) 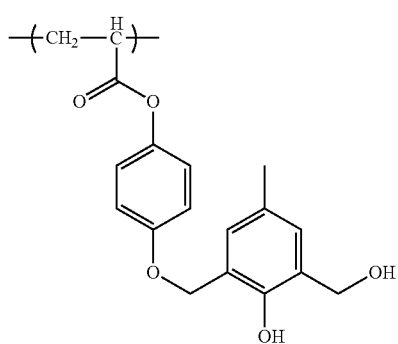
(Q-76) 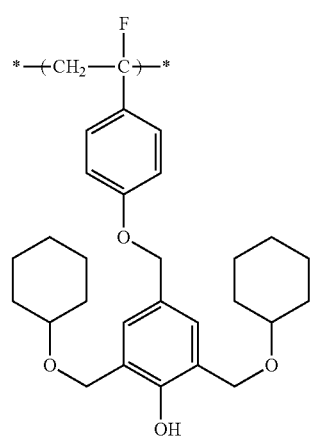
(Q-77) 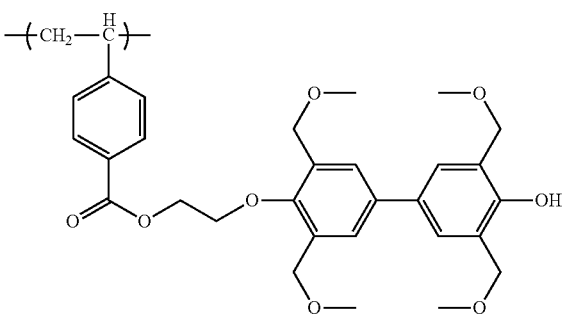
(Q-78) 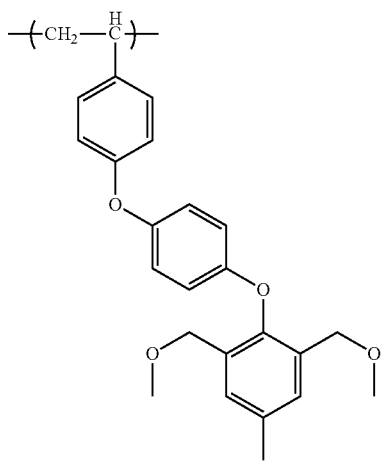
(Q-79) 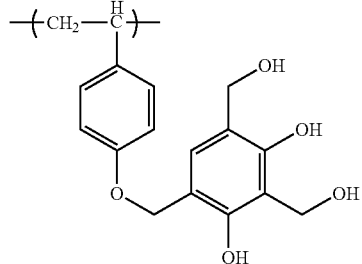

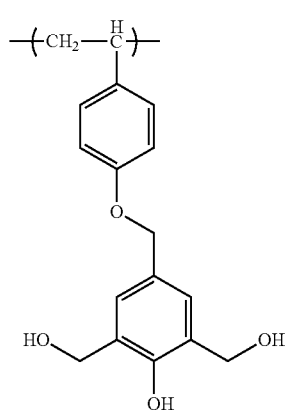
(Q-80)
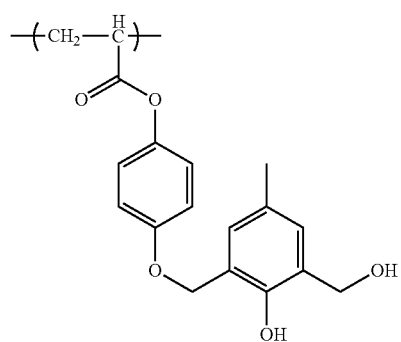
(Q-81)
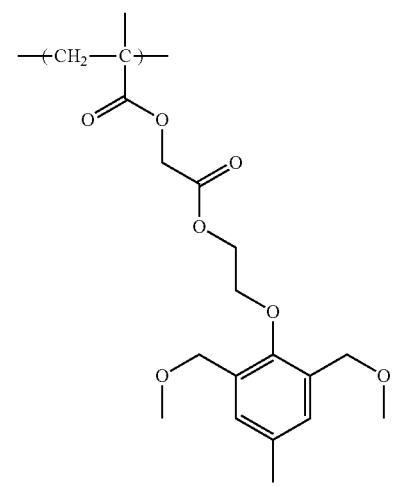
(Q-89)
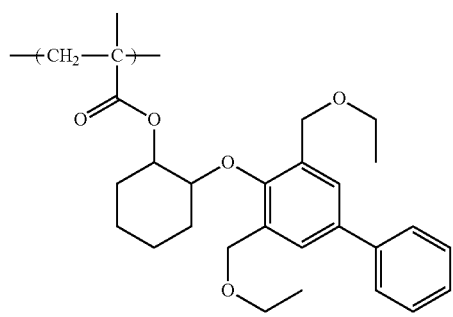
(Q-90)
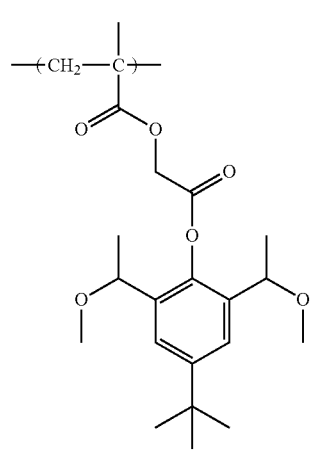
(Q-91)
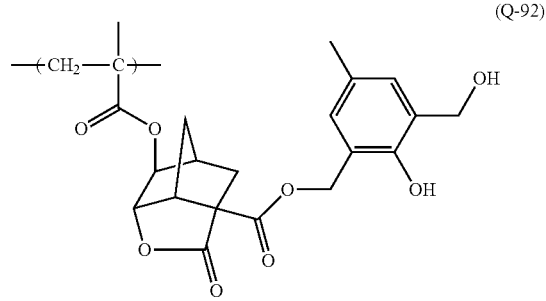
(Q-92)
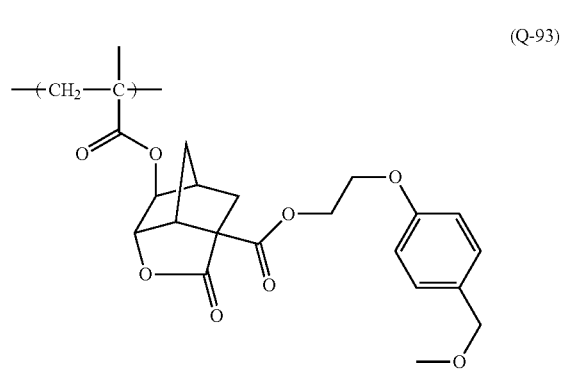
(Q-93)
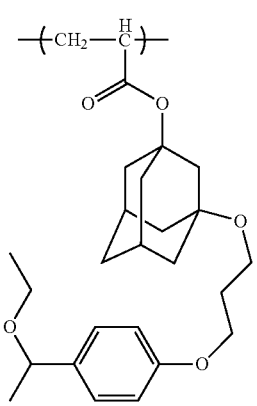
(Q-94)

(Q-95)
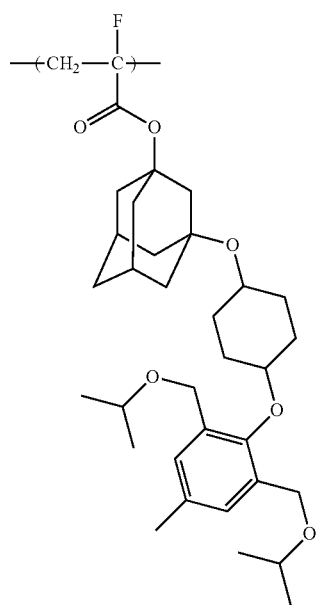
(Q-96)
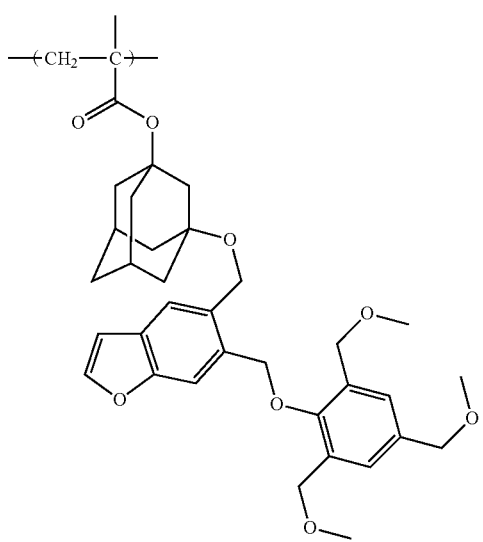
(Q-97)
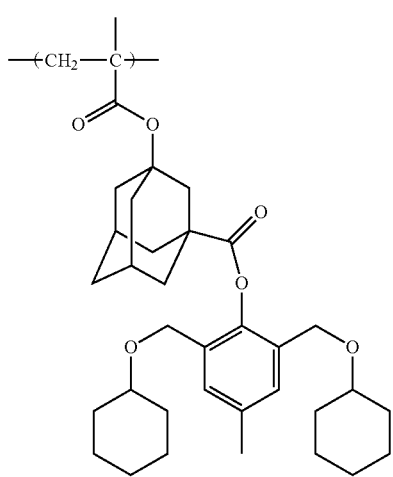
(Q-98)
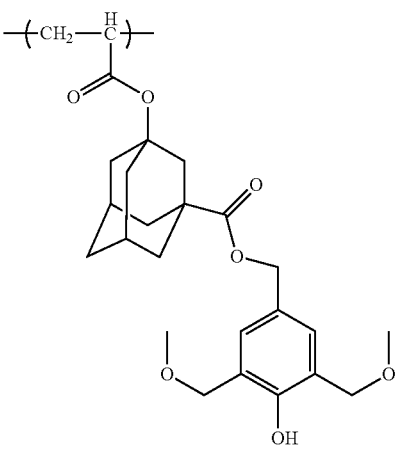
(Q-99)
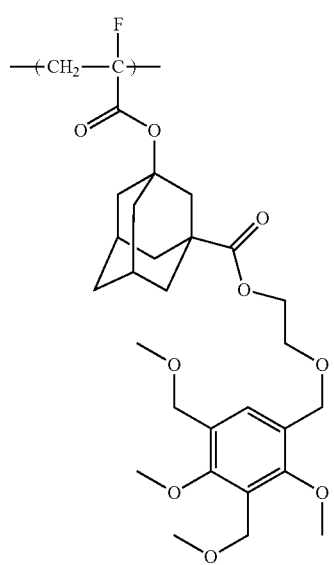
(Q-100)
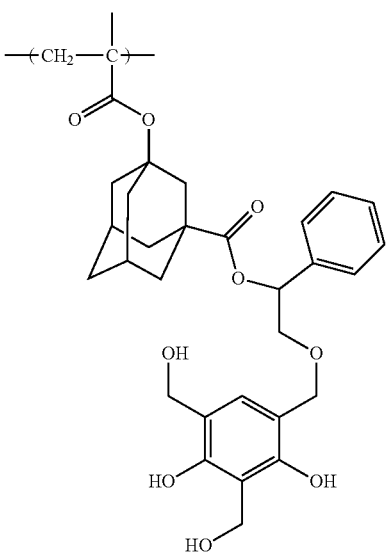

(Q-101)
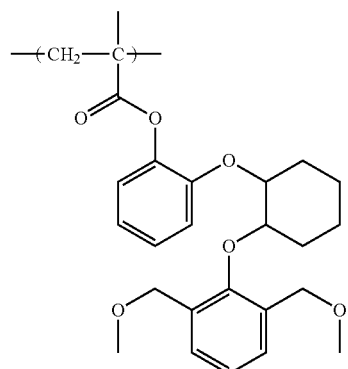
(Q-102)
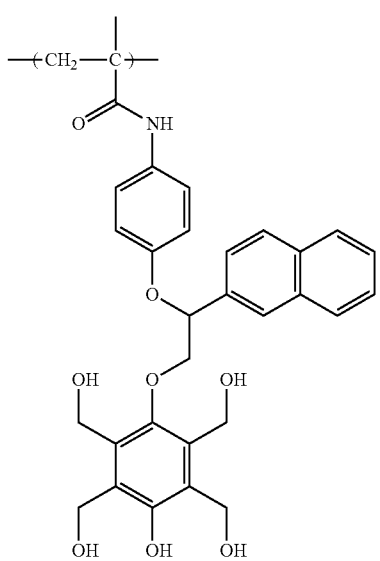
(Q-103)
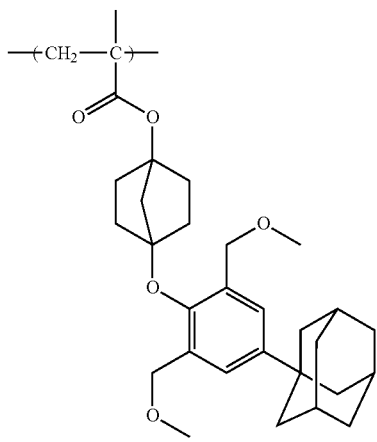
(Q-104)
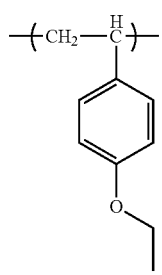
(Q-105)
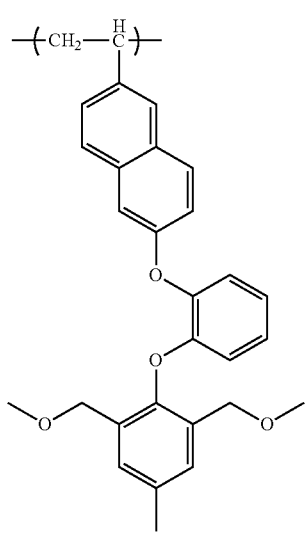
(A-106)
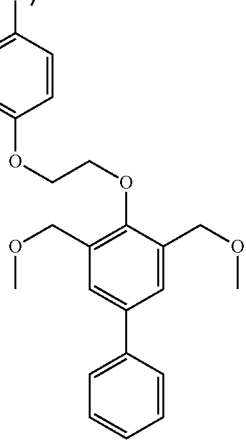

-continued (A-107)

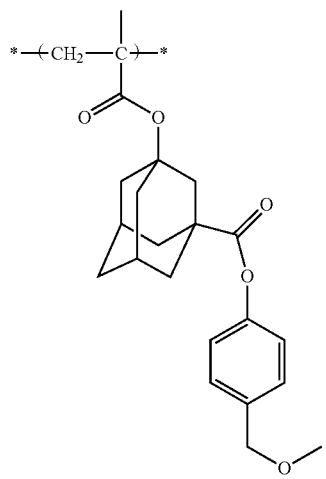

(A-108)

(A-109)

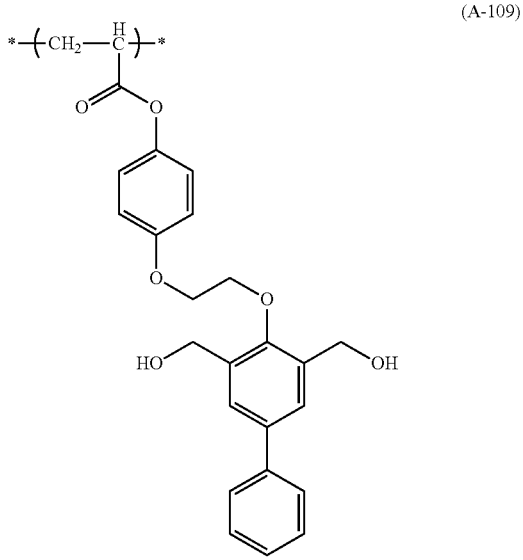

-continued (A-110)

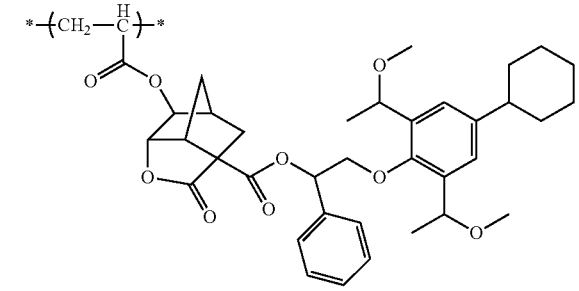

(A-111)

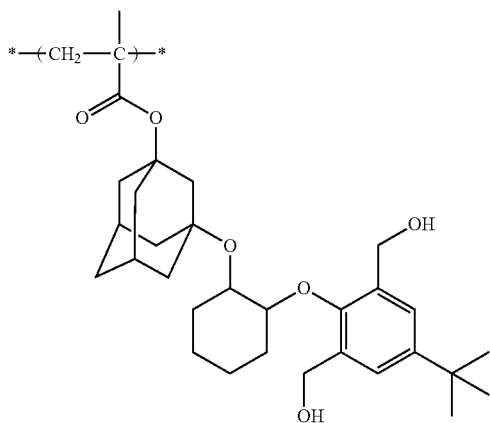

<Basic Compound>

The composition of the present invention preferably contains a basic compound as an acid scavenger, in addition to the above components. By using a basic compound, it is possible to reduce changes in performance over time from exposure to a post bake. The basic compound is preferably an organic basic compound, and more specifically aliphatic amines, aromatic amines, heterocyclic amines, a nitrogen-containing compound having a carboxyl group, a nitrogen-containing compound having a sulfonyl group, a nitrogen-containing compound having a hydroxy group, a nitrogen-containing compound having a hydroxyphenyl group, an alcoholic nitrogen-containing compound, amide derivatives, or imide derivatives. An amine oxide compound (described in JP2008-102383A) or an ammonium salt (a hydroxide or a carboxylate is preferable, and more specifically, tetraalkylammonium hydroxide represented by tetrabutylammonium hydroxide is preferable from the viewpoint of LER) is also suitably used.

A compound of which the basicity is increased due to the action of an acid can also be used as one type of basic compound.

Specific examples of the amines include tri-n-butyl amine, tri-n-pentyl amine, tri-n-octyl amine, tri-n-decyl amine, triisodecyl amine, dicyclohexyl methyl amine, tetradecyl amine, pentadecyl amine, hexadecyl amine, octadecyl amine, didecyl amine, methyl octadecyl amine, dimethyl undecyl amine, N,N-dimethyl dodecyl amine, methyl dioctadecyl amine, N,N-dibutyl aniline, N,N-dihexyl aniline, 2,6-diisopropyl aniline, 2,4,6-tri(t-butyl)aniline, triethanolamine, N,N-dihydroxyethyl aniline, tris(methoxyethoxyethyl)amine, the compounds exemplified after line 60 of column 3 of U.S. Pat. No. 6,040,112A, 2-[2-{2-(2,2-dimethoxy-phenoxyethoxy)ethyl}-bis-(2-methoxyethyl)]-amine, and the compounds (C1-1) to (C3-3) exemplified in paragraph "0066" of US2007/0224539A1. Examples of the compound having a nitrogen-containing heterocyclic structure include 2-phenylbenzimidazole, 2,4,5-triphenylimidazole, N-hydroxyethyl piperidine, bis(1,2,2,6,6-pentamethyl-4-piperidyl)sebacate, 4-dimethylaminopyridine, antipyrine, hydroxyantipyrine, 1,5-diazabicyclo[4.3.0]non-5-ene, 1,8-diazabicyclo[5.4.0]-undec-7-ene, and tetrabutylammonium hydroxide.

In addition, a photodegradable basic compound (compound which initially exhibits basicity due to the action of a basic nitrogen atom as a base, but generates a zwitterion compound having a basic nitrogen atom and an organic acid portion being decomposed by irradiation with active light or radiation, and by neutralization of this in the molecule, of which the basicity is reduced or lost, and for example, onium salts described in JP3577743B, JP2001-215689A, JP2001-166476A, or JP2008-102383A) and a photobase generator (for example, the compounds described in JP2010-243773A) may also be suitably used.

Among these basic compounds, an ammonium salt is preferable from the viewpoint of resolution improvement.

In addition, the composition of the present invention more preferably contains an onium salt compound (hereinafter, also referred to as a "compound (D)" or an "onium salt compound") including a nitrogen atom in the cationic portion as a basic compound, from the viewpoint of the effects of the present invention.

Examples of the onium salt compound include a diazonium salt compound, a phosphonium salt compounds, a sulfonium salt compound, and an iodonium salt compound. Among these, a sulfonium salt compound or an iodonium salt compound is preferable, and a sulfonium salt compound is more preferable.

The onium salt compound, typically, has a basic portion including a nitrogen atom in the cationic portion. The "basic portion" described here means a portion in which the pKa of the conjugate acid in the cationic portion of the compound (A) becomes −3 or greater. The pKa is preferably within a range of −3 to 15, and more preferably within a range of 0 to 15. Moreover, the pKa means a calculated value determined by ACD/ChemSketch (ACD/Labs 8.00 Release Product Version: 8.08).

The basic portion includes, for example, a structure selected from the group consisting of an amino group (a group in which one hydrogen atom is removed from ammonia, a primary amine, or a secondary amine; hereinafter, the same is applied) and a nitrogen-containing heterocyclic group. The amino group is preferably an aliphatic amino group. Here, the aliphatic amino group means a group in which one hydrogen atom is removed from an aliphatic amine.

In the structure, all atoms adjacent to the nitrogen atom included in the structure are preferably carbon atoms or hydrogen atoms from the viewpoint of the basicity improvement. In addition, from the viewpoint of the basicity improvement, it is preferable that an electron withdrawing functional group (a carbonyl group, a sulfonyl group, a cyano group, a halogen atom, or the like) is not directly connected to the nitrogen atom.

The onium salt compound may have two or more basic portion.

In a case where the cation portion of the compound (A) includes an amino group, the cation portion preferably has a substructure represented by the following General Formula (N-I).

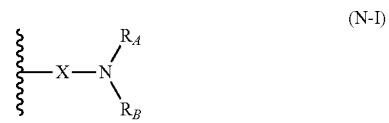

In the formula, each of $R_A$ and $R_B$ independently represents a hydrogen atom or an organic group.

X represents a single bond or a connecting group.

At least two of $R_A$, $R_B$, and X may be bonded to each other to form a ring.

Examples of the organic group represented by $R_A$ or $R_B$ include an alkyl group, a cycloalkyl group, an alkenyl group, an aryl group, a heterocyclic hydrocarbon group, an alkoxycarbonyl group, and a lactone group.

These groups may have a substituent, and examples of the substituent include an alkyl group, a cycloalkyl group, an alkoxy group, an alkoxycarbonyl group, a carboxyl group, a halogen atom, a hydroxyl group, and a cyano group.

The alkyl group represented by $R_A$ or $R_B$ may be linear or branched. The alkyl group preferably has 1 to 50 carbon atoms, more preferably 1 to 30 carbon atoms, and still more preferably 1 to 20 carbon atoms. Examples of such an alkyl group include a methyl group, an ethyl group, a propyl group, a butyl group, a hexyl group, an octyl group, a decyl group, a dodecyl group, an octadecyl group, an isopropyl group, an isobutyl group, a sec-butyl group, a t-butyl group, a 1-ethylpentyl group, and a 2-ethylhexyl group.

The cycloalkyl group represented by $R_A$ or $R_B$ may be monocyclic or polycyclic. As the cycloalkyl group, a monocyclic cycloalkyl group having 3 to 8 carbon atoms, such as a cyclopropyl group, a cyclopentyl group, or a cyclohexyl group is preferably exemplified.

The alkenyl group represented by $R_A$ or $R_B$ may be linear or branched. The alkenyl group preferably has 2 to 50 carbon atoms, more preferably 2 to 30 carbon atoms, and still more preferably 3 to 20 carbon atoms. Examples of the alkenyl group include a vinyl group, an allyl group, and a styryl group.

The aryl group represented by $R_A$ or $R_B$ preferably has 6 to 14 carbon atoms. Examples of such a group include a phenyl group and a naphthyl group.

The heterocyclic hydrocarbon group represented by $R_A$ or $R_B$ preferably has 5 to 20 carbon atoms, and more preferably has 6 to 15 carbon atoms. The heterocyclic hydrocarbon group may have or may not have aromaticity. The heterocyclic hydrocarbon group preferably has aromaticity.

The heterocycle included in the above group may be monocyclic or polycyclic. Examples of such a heterocycle include an imidazole ring, a pyridine ring, a pyrazine ring, a pyrimidine ring, a pyridazine ring, a 2H-pyrrole ring, a 3H-indole ring, 1H-indazole ring, a purine ring, an isoquinoline ring, a 4H-quinolizine ring, a quinoline ring, a phthalazine ring, a naphthyridine ring, a quinoxaline ring, a quinazoline ring, a cinnoline ring, a pteridine ring, a phenanthridine ring, an acridine ring, a phenanthroline ring, a phenazine ring, a perimidine ring, a triazine ring, a benzisoquinoline ring, a thiazole ring, a thiadiazine ring, an azepine ring, an azocine ring, an isothiazole ring, an isoxazole ring, and a benzothiazole ring.

Examples of the lactone group represented by $R_A$ or $R_B$ include a lactone group having a 5- to 7-membered ring, and the lactone group may be a lactone group in which another ring structure is condensed with a 5- to 7-membered ring lactone group while forming a bicyclo structure or a spiro structure. Specifically, a group having any one of structures shown below is preferable.

LC1-1
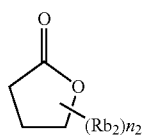

LC1-2
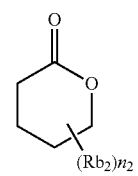

LC1-3
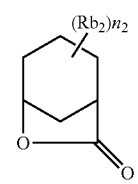

LC1-4
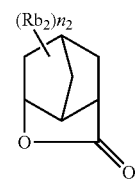

LC1-5
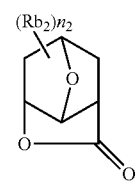

LC1-6
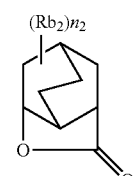

LC1-7
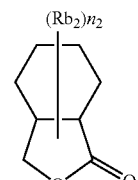

-continued

LC1-8
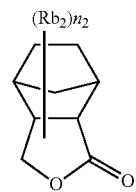

LC1-9
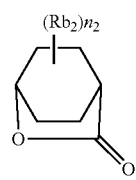

LC1-10
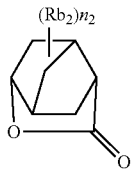

LC1-11
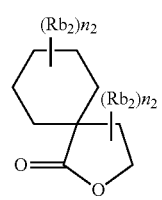

LC1-12
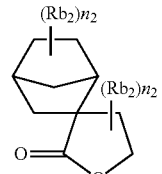

LC1-13
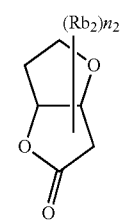

LC1-14
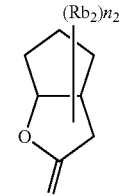

LC1-15
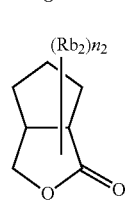

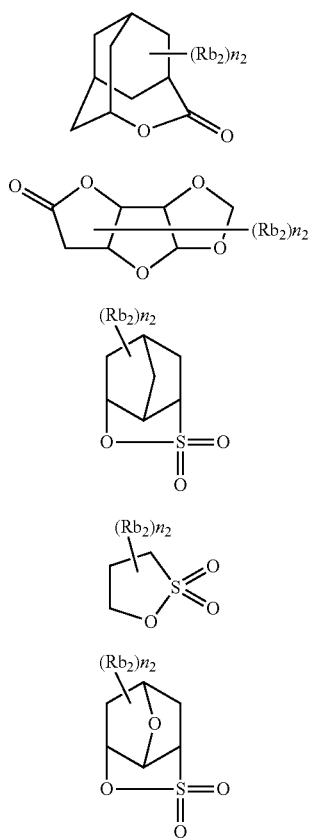

LC1-16

LC1-17

SL1-1

SL1-2

SL1-3

The lactone group may have or may not have a substituent ($Rb_2$). Examples of the substituent ($Rb_2$) include the same as the substituents represented by $R_A$ or $R_B$ described above. When $n_2$ is 2 or greater, plural substituents ($Rb_2$) present in a molecule may be the same as or different from each other. In addition, plural substituents ($Rb_2$) present in a molecule may be bonded to each other to form a ring.

Examples of the connecting group represented by X include a linear or branched alkylene group, a cycloalkylene group, an ether bond, an ester bond, an amide bond, a urethane bond, a urea bond, and a group obtained by combining two or more types thereof X more preferably represents a single bond, an alkylene group, a group obtained by combining an alkylene group and an ether bond, or a group obtained by combining an alkylene group and an ester bond. The connecting group represented by X preferably has 20 or less carbon atoms, and more preferably 15 or less carbon atoms. Each of the above-described linear or branched alkylene group and cycloalkylene group preferably has 8 or less carbon atoms, and may have a substituent. The substituent preferably has 8 or less carbon atoms, and examples thereof include an alkyl group (having 1 to 4 carbon atoms), a halogen atom, a hydroxyl group, an alkoxy group (having 1 to 4 carbon atoms), a carboxyl group, and an alkoxycarbonyl group (having 2 to 6 carbon atoms).

At least two of $R_A$, $R_B$, and X may be bonded to each other to form a ring. The number of carbon atoms forming the ring is preferably 4 to 20, and the ring may be monocyclic or polycyclic, and may include an oxygen atom, a sulfur atom, a nitrogen atom, an ester bond, an amide bond, or a carbonyl group in the ring.

In a case where the cation portion of the compound (D) includes a nitrogen-containing heterocyclic group, the nitrogen-containing heterocyclic group may have or may not have aromaticity. In addition, the nitrogen-containing heterocyclic group may be monocyclic or polycyclic. As the nitrogen-containing heterocyclic group, a group including a piperidine ring, a morpholine ring, a pyridine ring, an imidazole ring, a pyrazine ring, a pyrrole ring, or a pyrimidine ring is preferably exemplified.

The onium salt compound (D) is preferably a compound represented by the following General Formula (N-II).

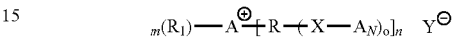

(N-II)

In the formula, A represents a sulfur atom or an iodine atom.

$R_1$ represents a hydrogen atom or an organic group. In a case where a plurality of $R_1$'s are present, $R_1$'s may be the same as or different from each other.

R represents an (o+1) valent organic group. In a case where a plurality of R's are present, R's may be the same as or different from each other.

X represents a single bond or a connecting group. In a case where a plurality of X's are present, X's may be the same as or different from each other.

$A_N$ represents a basic portion including a nitrogen atom. In a case where a plurality of $A_N$'s are present, $A_N$'s may be the same as or different from each other.

In a case where A is a sulfur atom, n is an integer of 1 to 3, and m is an integer that satisfies a relationship of m+n=3.

In a case where A is an iodine atom, n is 1 or 2, and m is an integer that satisfies a relationship of m+n=2.

o represents an integer of 1 to 10.

$Y^-$ represents an anion (in detail, those described below as the anion portion of the compound (D)).

At least two of $R_1$, X, R, and $A_N$ may be bonded to each other to form a ring.

Examples of the (o+1) valent organic group represented by R include a chain (linear or branched) or cyclic aliphatic hydrocarbon group, a heterocyclic hydrocarbon group, and an aromatic hydrocarbon group, and an aromatic hydrocarbon group is preferable. In a case where R is an aromatic hydrocarbon group, a bond is preferably formed at the p-position (1,4-position) of the aromatic hydrocarbon group.

The connecting group represented by X has the same meaning as the connecting group represented by X in General Formula (N-I), and the same specific examples can be exemplified.

The basic portion represented by $A_N$ has the same meaning as the "basic portion" included in the cation portion of the compound (D), and for example, the basic portion can include an amino group or a nitrogen-containing heterocyclic group. In a case where the basic portion includes an amino group, as the amino group, a —N($R_A$)($R_B$) in General Formula (N-I) is exemplified.

Examples of the organic group represented by $R_1$ include an alkyl group, an alkenyl group, an aliphatic cyclic group, an aromatic hydrocarbon group, and a heterocyclic hydrocarbon group. In a case where m is 2, two $R_1$'s may be bonded to each other to form a ring. These groups or rings may further have a substituent.

The alkyl group represented by $R_1$ may be linear or branched. The alkyl group preferably has 1 to 50 carbon atoms, more preferably 1 to 30 carbon atoms, and still more preferably 1 to 20 carbon atoms. Examples of such an alkyl group include a methyl group, an ethyl group, a propyl group, a butyl group, a hexyl group, an octyl group, a decyl group, a dodecyl group, an octadecyl group, an isopropyl group, an isobutyl group, a sec-butyl group, a t-butyl group, a 1-ethylpentyl group, and a 2-ethylhexyl group.

The alkenyl group represented by $R_1$ may be linear or branched. The alkenyl group preferably has 2 to 50 carbon atoms, more preferably 2 to 30 carbon atoms, and still more preferably 3 to 20 carbon atoms. Examples of such an alkenyl group include a vinyl group, an allyl group, and a styryl group.

Examples of the aliphatic cyclic group represented by $R_1$ include a cycloalkyl group. The cycloalkyl group may be monocyclic or polycyclic. As the aliphatic cyclic group, a monocyclic cycloalkyl group having 3 to 8 carbon atoms, such as a cyclopropyl group, a cyclopentyl group, or a cyclohexyl group is preferably exemplified.

The aromatic hydrocarbon group represented by $R_1$ preferably has 6 to 14 carbon atoms. Examples of such a group include an aryl group such as a phenyl group or a naphthyl group. The aromatic hydrocarbon group represented by $R_1$ is preferably a phenyl group.

The heterocyclic hydrocarbon group represented by $R_1$ may have or may not have aromaticity. The heterocyclic hydrocarbon group preferably has aromaticity.

The heterocycle included in the above group may be monocyclic or polycyclic. Examples of such a heterocycle include an imidazole ring, a pyridine ring, a pyrazine ring, a pyrimidine ring, a pyridazine ring, a 2H-pyrrole ring, a 3H-indole ring, 1H-indazole ring, a purine ring, an isoquinoline ring, a 4H-quinolizine ring, a quinoline ring, a phthalazine ring, a naphthyridine ring, a quinoxaline ring, a quinazoline ring, a cinnoline ring, a pteridine ring, a phenanthridine ring, an acridine ring, a phenanthroline ring, a phenazine ring, a perimidine ring, a triazine ring, a benzisoquinoline ring, a thiazole ring, a thiadiazine ring, an azepine ring, an azocine ring, an isothiazole ring, an isoxazole ring, and a benzothiazole ring.

$R_1$ is an aromatic hydrocarbon group or two $R_1$'s are preferably bonded to each other to form a ring.

The ring which may be formed by bonding of at least two of $R_1$, X, R, and $A_N$ to each other is preferably a 4- to 7-membered ring, more preferably a 5- or 6-membered ring, and particularly preferably a 5-membered ring. In addition, a heteroatom such as an oxygen atom, a sulfur atom, or a nitrogen atom may be included in the ring skeleton.

In a case where a group formed by bonding of the groups represented by $R_1$ or two $R_1$'s to each other further has a substituent, examples of the substituent include the following. That is, examples of the substituent include a halogen atom (—F, —Br, —Cl, or —I), a hydroxyl group, an alkoxy group, an aryloxy group, a mercapto group, an alkylthio group, an arylthio group, an amino group, an acyloxy group, a carbamoyloxy group, an alkylsulfoxy group, an arylsulfoxy group, an acylthio group, an acylamino group, a ureido group, an alkoxycarbonylamino group, an aryloxycarbonylamino group, an N-alkyl-N-alkoxycarbonylamino group, an N-alkyl-N-aryloxycarbonyl amino group, an N-aryl-N-alkoxycarbonylamino group, an N-aryl-N-aryloxycarbonyl amino group, a formyl group, an acyl group, a carboxyl group, a carbamoyl group, an alkylsulfinyl group, an arylsulfinyl group, an alkylsulfonyl group, an arylsulfonyl group, an sulfo group (—SO₃H) or a conjugated base group thereof (referred to as a sulfonato group), an alkoxysulfonyl group, an aryloxysulfonyl group, a sulfinamoyl group, a phosphono group (—PO₃H₂) or a conjugated base group thereof (referred to as a phosphonato group), a phosphonooxy group (—OPO₃H₂) or a conjugated base group thereof (referred to as phosphonatooxy group), a cyano group, a nitro group, an aryl group, an alkenyl group, an alkynyl group, a heterocyclic group, a silyl group, and an alkyl group.

Among these substituents, a hydroxyl group, an alkoxy group, a cyano group, an aryl group, an alkenyl group, an alkynyl group, or an alkyl group is preferable.

In General Formula (N-II), o is preferably an integer of 1 to 4, more preferably 1 or 2, and still more preferably 1.

The compound (D) represented by General Formula (N-II), in one aspect, at least one of n R's in the formula is preferably an aromatic hydrocarbon group. X in at least one of o —(X-$A_N$) groups bonded to at least one of the aromatic hydrocarbon groups is preferably a connecting group in which the bonding portion to the aromatic hydrocarbon group is a carbon atom.

That is, in the compound (D) in the aspect, The basic portion represented by $A_N$ is bonded to the aromatic hydrocarbon group through a carbon atom directly bonded to the aromatic hydrocarbon group represented by R.

The aromatic hydrocarbon group represented by R may include a heterocycle as an aromatic ring in the aromatic hydrocarbon group. In addition, the aromatic ring may be monocyclic or polycyclic.

The aromatic ring group preferably has 6 to 14 carbon atoms. Examples of such a group include an aryl group such as a phenyl group, a naphthyl group, or an anthryl group. In a case where the aromatic ring group includes a heterocycle, examples of the heterocycle include a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring, and a thiazole ring.

The aromatic hydrocarbon group represented by R is preferably a phenyl group or a naphthyl group, and particularly preferably a phenyl group.

The aromatic hydrocarbon group represented by R may further have a substituent, in addition to a group represented by —(X-$A_N$) described below. As the substituent, those exemplified as the substituent in $R_1$ described above can be used.

In addition, in the aspect, the connecting group as X in at least one of —(X-$A_N$) groups with which the aromatic ring R substituted is not particularly limited as long as the bonding portion to the aromatic hydrocarbon group represented by R is a carbon atom. Examples of the connecting group include an alkylene group, a cycloalkylene group, an arylene group, —COO—, —CO—, and a combination thereof. The connecting group may include a combination with at least one selected from the group consisting of each of these groups, —O—, —S—, —OCO—, —S(=O)—, —S(=O)₂—, —OS(=O)₂—, and —NR'—. Here, R' represents, for example, a hydrogen atom, an alkyl group, a cycloalkyl group, or an aryl group.

The alkylene group which can be included in the connecting group represented by X may be linear or branched. The alkylene group preferably has 1 to 20 carbon atoms and more preferably has 1 to 10 carbon atoms. Examples of such an alkylene group include a methylene group, an ethylene group, a propylene group, and a butylene group.

The cycloalkylene group which can be included in the connecting group represented by X may be monocyclic or polycyclic. The cycloalkylene group preferably has 3 to 20 carbon atoms, and more preferably has 3 to 10 carbon atoms. Examples of such a cycloalkylene group include a 1,4-cyclohexylene group.

The arylene group which can be included in the connecting group represented by X preferably has 6 to 20 carbon atoms, and more preferably has 6 to 10 carbon atoms. Examples of such an arylene group include a phenylene group and a naphthylene group.

At least one X is preferably represented by the following General Formula (N-III) or (N-IV).

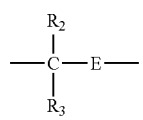
(N-III)

In the formula, each of $R_2$ and $R_3$ represents a hydrogen atom, an alkyl group, an alkenyl group, an aliphatic cyclic group, an aromatic hydrocarbon group, or a heterocyclic hydrocarbon group. $R_2$ and $R_3$ may be bonded to each other to form a ring. At least one of $R_2$ and $R_3$ may be bonded to E to form a ring.

E represents a connecting group or a single bond.

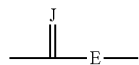
(N-IV)

In the formula, J represents an oxygen atom or a sulfur atom.

E represents a connecting group or a single bond.

Examples of each group represented by $R_2$ or $R_3$ and the substituents which these groups can further have include the same as those exemplified for $R_1$ above. The ring which can be formed by bonding of $R_2$ and $R_3$ to each other and the ring which can be formed by bonding of at least one of $R_2$ and $R_3$ to E is preferably a 4- to 7-membered ring, and more preferably a 5- or 6-membered ring. Each of $R_2$ and $R_3$ is independently preferably a hydrogen atom or an alkyl group.

Examples of the connecting group represented by E include an alkylene group, a cycloalkylene group, an arylene group, —COO—, —CO—, —O—, —S—, —OCO—, —S(=O)—, —S(=O)$_2$—, —OS(=O)$_2$—, —NR—, and a combination thereof. Here, R represents, for example, a hydrogen atom, an alkyl group, a cycloalkyl group, or an aryl group.

The connecting group represented by E is preferably at least one selected from the group consisting of an alkylene bond, an ester bond, an ether bond, a thioether bond, a urethane bond,

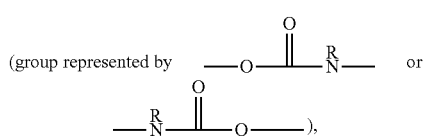
(group represented by           or           ), a urea bond

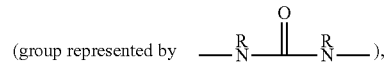
(group represented by           ), an amide bond, and a sulfonamide bond.

The connecting group represented by E is more preferably an alkylene bond, an ester bond, or an ether bond.

Moreover, the compound (D) may be a compound having a plurality of portions including a nitrogen atom. For example, in the compound (D), at least one of $R_1$'s in General Formula (N-II) may be a compound having the structure represented by General Formula (N-I).

The compound (D) represented by General Formula (N-II), in one aspect, is represented by the following General Formula (N-V).

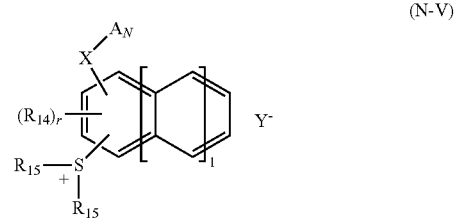
(N-V)

In the formula, each of X, $A_N$, and $Y^-$ has the same meaning as each group in General Formula (N-II), and the specific examples and the preferable examples thereof are also the same.

Each of $R_{14}$, $R_{15}$, r, and l has the same meaning as each group and each index in General Formula (ZI-4) which represents an aspect of a photoacid generator (B) described below, and the specific examples and the preferable examples thereof are also the same.

In addition, the compound (D) represented by General Formula (N-II), in one aspect, is represented by the following General Formula (N-VI).

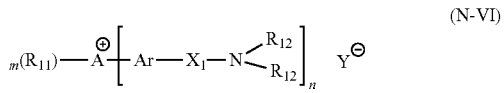
(N-VI)

In General Formula (N-VI), A represents a sulfur atom or an iodine atom.

Each of $R_{11}$'s independently represents an alkyl group, an alkenyl group, an aliphatic cyclic group, an aromatic hydrocarbon group, or a heterocyclic hydrocarbon group. In a case where m is 2, two $R_{11}$'s may be bonded to each other to form a ring.

Each of Ar's independently represents an aromatic hydrocarbon group.

Each of $X_1$'s independently represents a divalent connecting group.

Each of $R_{12}$'s independently represents a hydrogen atom or an organic group.

In a case where A is a sulfur atom, m is an integer of 1 to 3, and n is an integer that satisfies a relationship of m+n=3.

In a case where A is an iodine atom, m is an integer of 1 or 2, and n is an integer that satisfies a relationship of m+n=2.

$Y^-$ represents an anion (in detail, those described below as the anion portion of the compound (D)).

Specific examples and preferable examples of the alkyl group, the alkenyl group, the aliphatic cyclic group, the aromatic hydrocarbon group, or the heterocyclic hydrocarbon group represented by $R_{11}$ include the same as the specific examples and preferable examples of the alkyl group, the alkenyl group, the aliphatic cyclic group, the aromatic hydrocarbon group, or the heterocyclic hydrocarbon group represented by $R_1$ in General Formula (N-II).

Specific examples and preferable examples of the aromatic hydrocarbon group represented by Ar include the same as the specific examples and preferable examples of the aromatic hydrocarbon group represented by R in General Formula (N-II).

Specific examples and preferable examples of the divalent connecting group represented by $X_1$ include the same as the specific examples and preferable examples of the connecting group represented by X in General Formula (N-II).

Specific examples and preferable examples of the organic group represented by $R_{12}$ include the same as the specific examples and preferable examples of the organic group represented by $R_A$ or $R_B$ in General Formula (N-I).

An aspect in which X is an alkylene group (for example, a methylene group) and two $R_{12}$'s are bonded to each other to form a ring is particularly preferably from the viewpoint of temperature dependence of post exposure bake (PEB) and stability of a line width after exposure (PED).

The anion portion of the compound (D) is not particularly limited. The anion included in the compound (D) is preferably a non-nucleophilic anion. Here, the non-nucleophilic anion is an anion with a very low ability for causing a nucleophilic reaction, and is an anion which can suppress temporal decomposition caused by an intra-molecular nucleophilic reaction. Thus, the temporal stability of the composition according to the present invention is improved.

Examples of the non-nucleophilic anion include a sulfonate anion, a carboxylate anion, a sulfonylimide anion, a bis(alkylsulfonyl)imide anion, and a tris(alkylsulfonyl)methyl anion.

Examples of the sulfonate anion include an aliphatic sulfonate anion, an aromatic sulfonate anion, and a camphorsulfonate anion.

Examples of the carboxylate anion include an aliphatic carboxylate anion, an aromatic carboxylate anion, and an aralkylcarboxylate anion.

The aliphatic portion in the aliphatic sulfonate anion may be an alkyl group or a cycloalkyl group, and preferably an alkyl group having 1 to 30 carbon atoms or a cycloalkyl group having 3 to 30 carbon atoms, such as a methyl group, an ethyl group, a propyl group, an isopropyl group, a n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group, or a bornyl group.

The aromatic group in the aromatic sulfonate anion is preferably an aryl group having 6 to 14 carbon atoms, and examples thereof can include a phenyl group, a tolyl group, and a naphthyl group.

The alkyl group, the cycloalkyl group, and the aryl group in an aliphatic sulfonate anion and an aromatic sulfonate anion may have a substituent. Examples of the substituent of the alkyl group, the cycloalkyl group, and the aryl group in an aliphatic sulfonate anion and an aromatic sulfonate anion include a nitro group, a halogen atom (a fluorine atom, a chlorine atom, a bromine atom, or an iodine atom), a carboxy group, a hydroxyl group, an amino group, a cyano group, an alkoxy group (preferably having 1 to 15 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), an alkoxycarbonyloxy group (preferably having 2 to 7 carbon atoms), an alkylthio group (preferably having 1 to 15 carbon atoms), an alkylsulfonyl group (preferably having 1 to 15 carbon atoms), an alkyliminosulfonyl group (preferably having 2 to 15 carbon atoms), an aryloxysulfonyl group (preferably having 6 to 20 carbon atoms), an alkylaryloxysulfonyl group (preferably having 7 to 20 carbon atoms), a cycloalkylaryloxysulfonyl group (preferably having 10 to 20 carbon atoms), an alkyloxyalkyloxy group (preferably having 5 to 20 carbon atoms), and a cycloalkylalkyloxyalkyloxy group (preferably having 8 to 20 carbon atoms). Regarding the aryl group or a ring structure which each group has, as a substituent, an alkyl group (preferably having 1 to 15 carbon atoms) can be further exemplified.

Examples of the aliphatic portion in the aliphatic carboxylate anion include the same as the alkyl group and the cycloalkyl group in the aliphatic sulfonate anion.

Examples of the aromatic group in the aromatic carboxylate anion include the same as the aryl group in the aromatic sulfonate anion.

The aralkyl group in the aralkylcarboxylate anion is preferably an aralkyl group having 6 to 12 carbon atoms, and examples thereof can include a benzyl group, a phenethyl group, a naphthylmethyl group, a naphthylethyl group, and a naphthylbutyl group.

The alkyl group, the cycloalkyl group, the aryl group, and the aralkyl group in an aliphatic carboxylate anion, an aromatic carboxylate anion, an aralkylcarboxylate anion may have a substituent. Examples of the substituent of the alkyl group, the cycloalkyl group, the aryl group, and the aralkyl group in the aliphatic carboxylate anion, the aromatic carboxylate anion, and the aralkylcarboxylate anion include the same as the halogen atom, the alkyl group, the cycloalkyl group, the alkoxy group, and the alkylthio group in the aromatic sulfonate anion.

Examples of the sulfonylimide anion include a saccharin anion.

The alkyl group in an bis(alkylsulfonyl)imide anion and a tris(alkylsulfonyl)methyl anion is preferably an alkyl group having 1 to 5 carbon atoms, and examples thereof include a methyl group, an ethyl group, a propyl group, an isopropyl group, an n-butyl group, an isobutyl group, a sec-butyl group, a pentyl group, and a neopentyl group. Examples of the substituent of the alkyl group include a halogen atom, an alkyl group substituted with a halogen atom, an alkoxy group, an alkylthio group, an alkyloxysulfonyl group, an aryloxysulfonyl group, and a cycloalkylaryloxysulfonyl group, and an alkyl group substituted with a fluorine atom is preferable. In addition, an aspect in which two alkyl group in bis(alkylsulfonyl)imide anion may be bonded to each other to form a ring structure is also preferable. In this case, the ring structure formed is preferably a 5- to 7-membered ring.

Examples of other non-nucleophilic anions include fluorophosphate, fluoroborate, and fluoroantimonate.

As the non-nucleophilic anion, an aliphatic sulfonate anion in which the α position of sulfonic acid is substituted with a fluorine atom, an aromatic sulfonate anion substituted with a fluorine atom or a group having a fluorine atom, a bis(alkylsulfonyl)imide anion in which the alkyl group is substituted with a fluorine atom, or a tris(alkylsulfonyl) methide anion in which the alkyl group is substituted with a fluorine atom is preferable. The non-nucleophilic anion is more preferably a perfluoroaliphatic sulfonate anion having 4 to 8 carbon atoms or a benzenesulfonate anion having a fluorine atom, and still more preferably a nonafluorobutanesulfonate anion, a perfluorooctanesulfonate anion, a pentafluorobenzenesulfonate anion, or a 3,5-bis(trifluoromethyl) benzenesulfonate anion.

In addition, the non-nucleophilic anion is, for example, preferably a non-nucleophilic anion represented by the following General Formula (LD1).

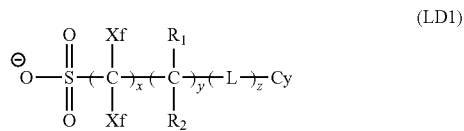
(LD1)

In the formula, each of Xf's independently represents a fluorine atom or an alkyl group substituted with at least one fluorine atom;

Each of $R_1$ and $R_2$ independently represents a hydrogen atom, a fluorine atom, or an alkyl group.

Each of L's independently represents a divalent connecting group.

Cy represents a cyclic organic group.

x represents an integer of 1 to 20.

y represents an integer of 0 to 10.

z represents an integer of 0 to 10.

Xf represents a fluorine atom or an alkyl group substituted with at least one fluorine atom. The alkyl group preferably has 1 to 10 carbon atoms, and more preferably has 1 to 4 carbon atoms. In addition, the alkyl group substituted with at least one fluorine atom is preferably a perfluoroalkyl group.

Xf is preferably a fluorine atom or a perfluoroalkyl group which has 1 to 4 carbon atoms. More specifically, Xf is preferably a fluorine atom, $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$, or $CH_2CH_2C_4F_9$.

Each of $R_1$ and $R_2$ independently represents a hydrogen atom, a fluorine atom, or an alkyl group. The alkyl group may have a substituent (preferably a fluorine atom) and preferably has 1 to 4 carbon atoms. The alkyl group is more preferably a perfluoroalkyl group having 1 to 4 carbon atoms. Specific examples of the alkyl group having the substituent represented by $R_1$ to $R_2$ include $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$, and $CH_2CH_2C_4F_9$, and among these, $CF_3$ is preferable.

L represents a divalent connecting group. Examples of the divalent connecting group include —COO—, —OCO—, —CONH—, —CO—, —O—, —S—, —SO—, —$SO_2$—, an alkylene group, a cycloalkylene group, and an alkenylene group. Among these, —CONH—, —CO—, or —$SO_2$— is preferable, and —CONH— or —$SO_2$— is more preferable.

Cy represents a cyclic organic group. Examples of the cyclic organic group include an alicyclic group, an aryl group, and a heterocyclic group.

The alicyclic group may be monocyclic or polycyclic. Examples of the monocyclic alicyclic group include a monocyclic cycloalkyl group such as a cyclopentyl group, a cyclohexyl group, or a cyclooctyl group. Examples of the polycyclic alicyclic group include a ploycyclic cycloalkyl group such as a norbornyl group, a tricyclodecanyl group, a tetracyclodecanyl group, a tetracyclododecanyl group, or an adamantyl group. Among these, an alicyclic group with a bulky structure having 7 or more carbon atoms such as a norbornyl group, a tricyclodecanyl group, a tetracyclodecanyl group, a tetracyclododecanyl group, or an adamantyl group is preferable from the viewpoint of suppression of in-film diffusibility in a PEB (post exposure bake) step and MEEF (mask error enhancement factor) improvement.

The aryl group may be monocyclic or polycyclic. Examples of the aryl group include a phenyl group, a naphthyl group, a phenanthryl group, and an anthryl group. Among these, a naphthyl group having comparatively low absorbance at 193 nm is preferable.

Although the heterocyclic group may be monocyclic or polycyclic, a polycyclic one can further suppress the diffusion of an acid. In addition, the heterocyclic group may have or may not have aromaticity. Examples of the heterocyclic group having aromaticity include a furan ring, a thiophene ring, a benzofuran ring, a benzothiophene ring, a dibenzofuran ring, a dibenzothiophene ring, and a pyridine ring. Examples of the heterocycle not having aromaticity include a tetrahydropyran ring, a lactone ring, and a decahydroisoquinoline ring. As the heterocycle in a heterocyclic group, a furan ring, a thiophene ring, a pyridine ring, or a decahydroisoquinoline ring is particularly preferable. In addition, examples of the lactone ring include the lactone rings exemplified for $R_A$ and $R_B$ in General Formula (N-1).

The cyclic organic group may have a substituent. Examples of the substituent include an alkyl group, a cycloalkyl group, an aryl group, a hydroxy group, an alkoxy group, an ester group, an amide group, a urethane group, a ureido group, a thioether group, a sulfonamide group, and a sulfonic ester group. The alkyl group may be linear, or may be branched. In addition, the alkyl group preferably has 1 to 12 carbon atoms. The cycloalkyl group may be monocyclic or polycyclic. In addition, the cycloalkyl group preferably has 3 to 12 carbon atoms. The aryl group preferably has 6 to 14 carbon atoms.

x is preferably 1 to 8, and among these, x is preferably 1 to 4, and particularly preferably 1. y is preferably 0 to 4, and more preferably 0. z is preferably 0 to 8, and among these, z is preferably 0 to 4.

In addition, the non-nucleophilic anion is, for example, preferably a non-nucleophilic anion represented by the following General Formula (LD2).

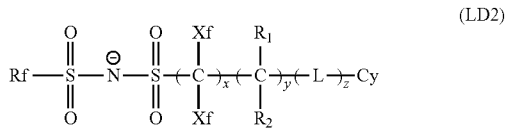
(LD2)

Each of Xf, $R_1$, $R_2$, L, Cy, x, y, and z in General Formula (LD2) has the same meaning as each group in General Formula (LD1). Rf represents a group including a fluorine atom.

Examples of the group including a fluorine atom represented by Rf include an alkyl group having at least one fluorine atom, a cycloalkyl group having at least one fluorine atom, and an aryl group having at least one fluorine atom.

These alkyl group, cycloalkyl group, and aryl group may be substituted with a fluorine atom, and may be substituted with another substituent including a fluorine atom. In a case where Rf is a cycloalkyl group having at least one fluorine atom or an aryl group having at least one fluorine atom, as another substituent including a fluorine atom, an alkyl group substituted with at least one fluorine atom is exemplified.

In addition, these alkyl group, cycloalkyl group, and aryl group may be further substituted with a substituent not including a fluorine atom. Examples of the substituent include substituents not including a fluorine atom among those described for Cy above.

Examples of the alkyl group having at least one fluorine atom represented by Rf include the same as those described above as the alkyl group substituted with at least one fluorine atom represented by Xf. Examples of the cycloalkyl group having at least one fluorine atom represented by Rf include a perfluorocyclopentyl group and a perfluorocyclohexyl group. Examples of the aryl group having at least one fluorine atom represented by Rf include a perfluorophenyl group.

As a preferable aspect of the anion portion of the compound (D), in addition to the structure represented by General Formula (LD1) or (LD2), structures exemplified as a preferable anion structure of the photoacid generator (B) described below can be exemplified.

In addition, in the compound (D), the fluorine content represented by (total mass of entirety of fluorine atoms included in a compound)/(total mass of entirety of atoms included in a compound) is preferably 0.30 or less, more preferably 0.25 or less, still more preferably 0.20 or less, particularly preferably 0.15 or less, and most preferably 0.10 or less.

Specific examples of the compound (D) are exemplified below; but the present invention is not limited thereto.

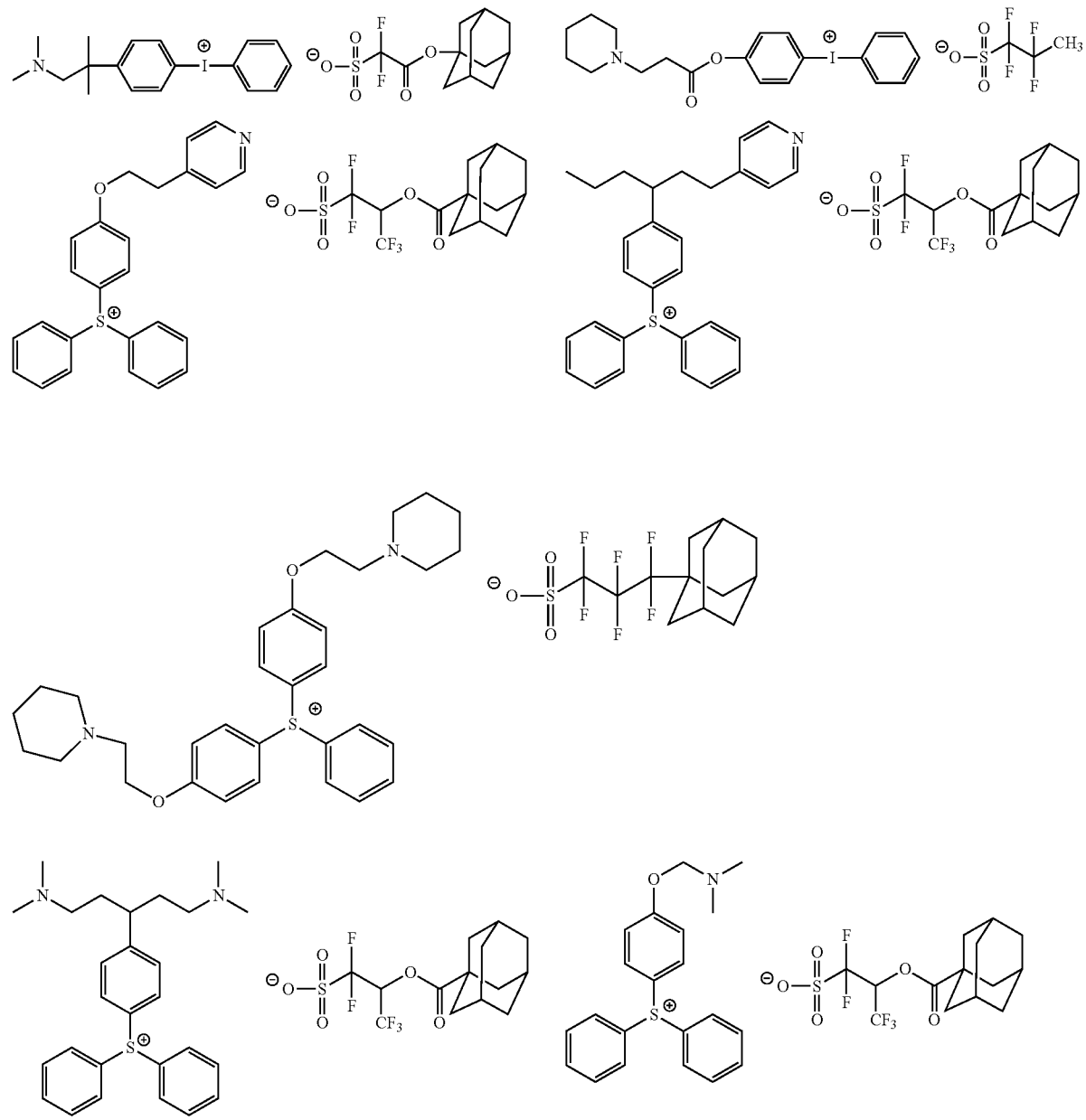

115
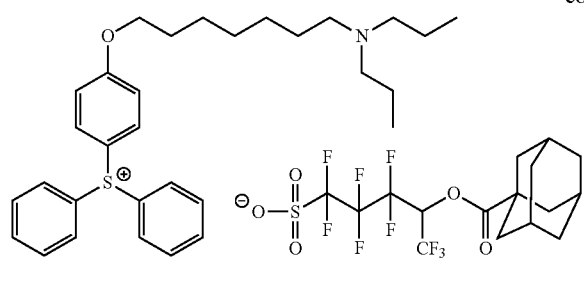
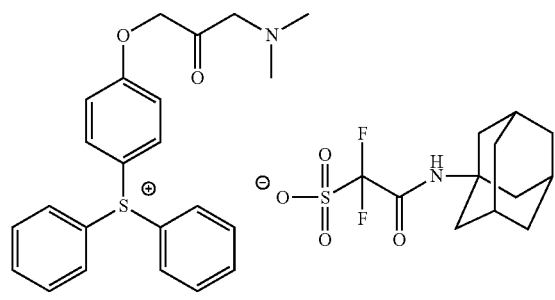
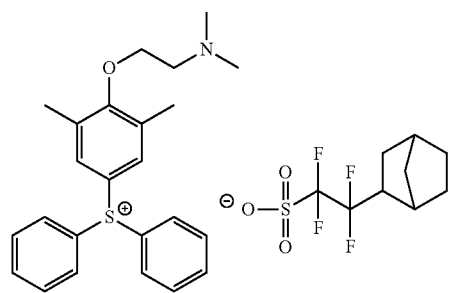
116
-continued
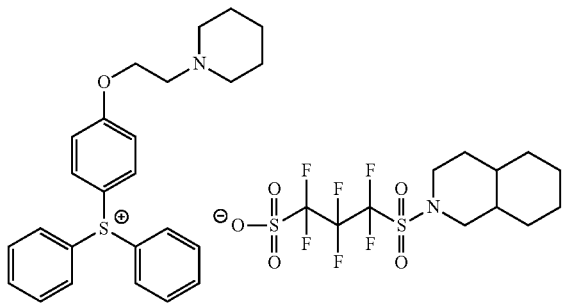
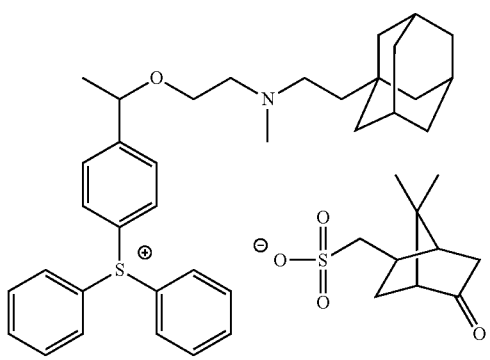
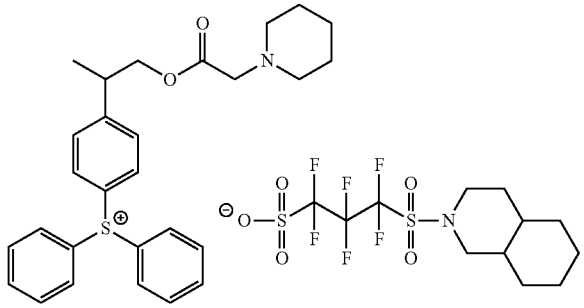
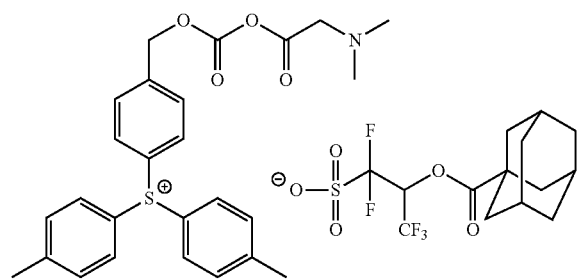
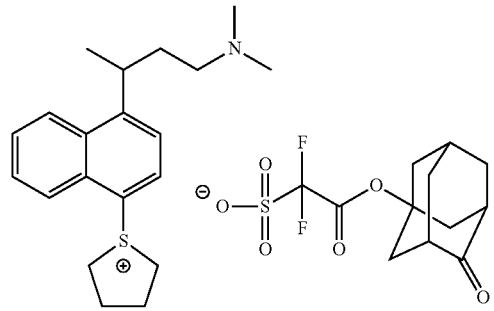
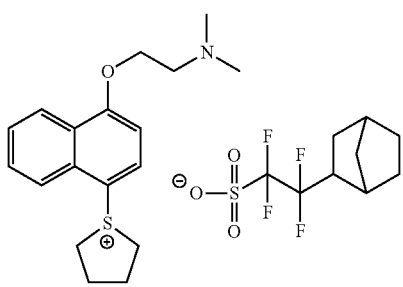
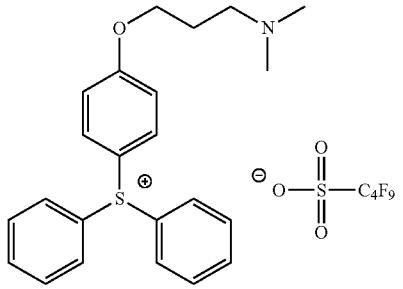

-continued
117
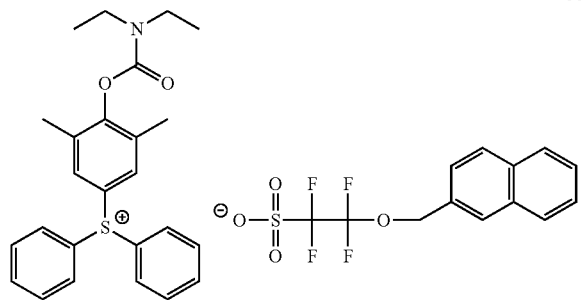
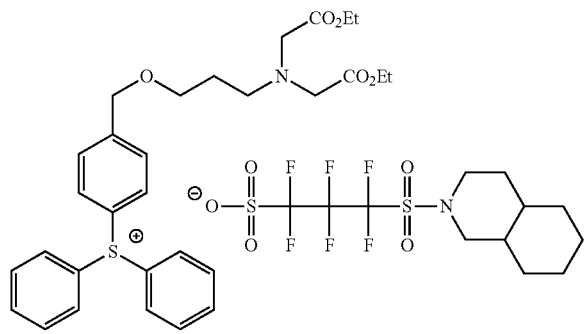
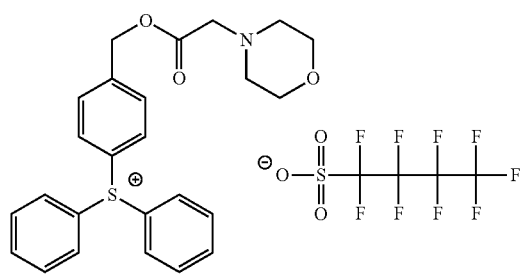
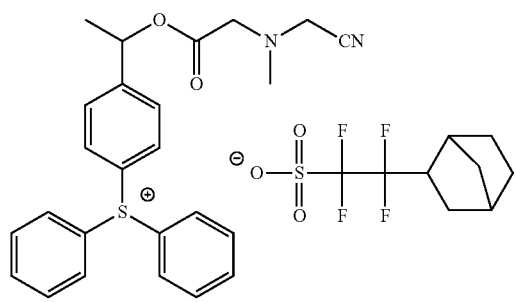
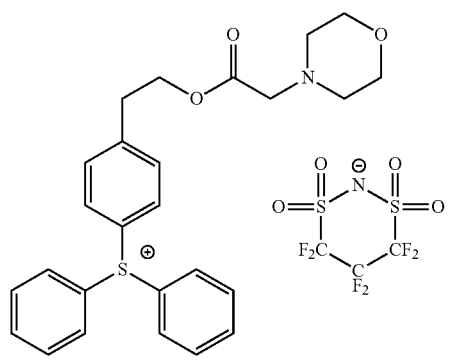
118
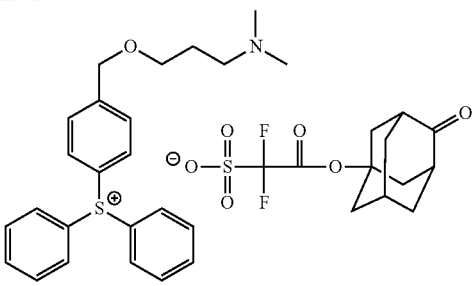
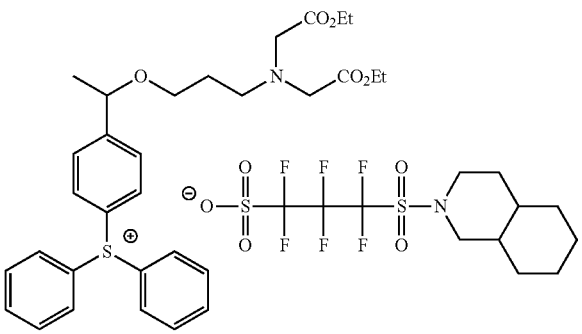
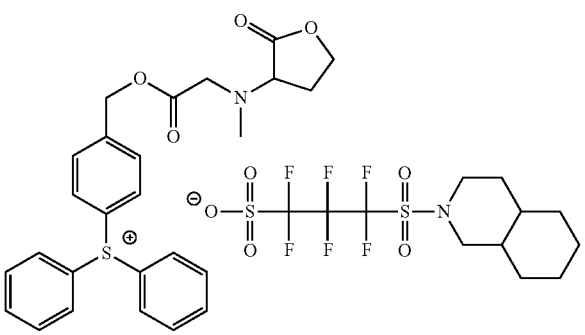
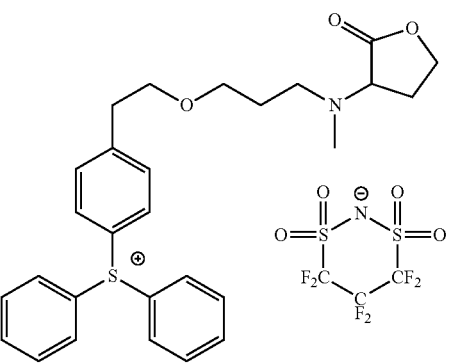
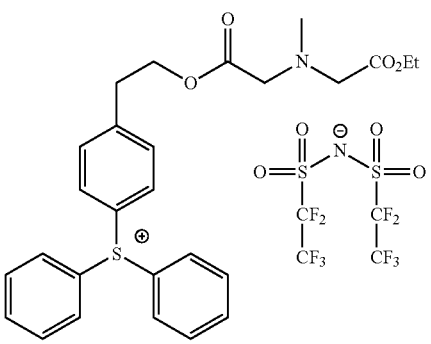

119
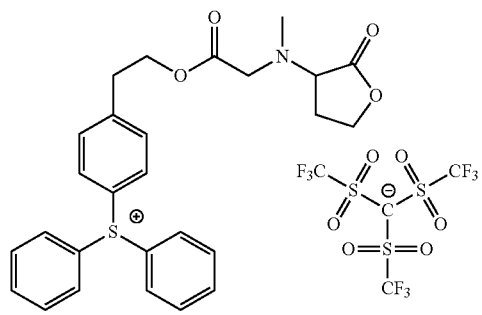
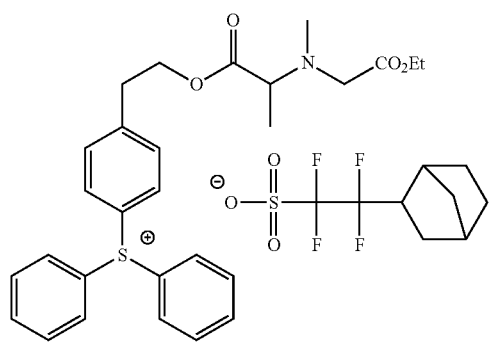
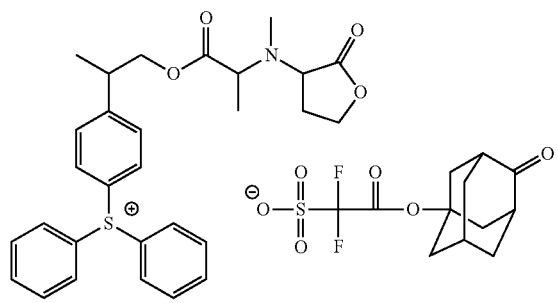
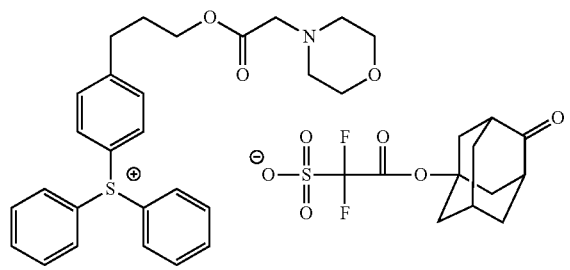
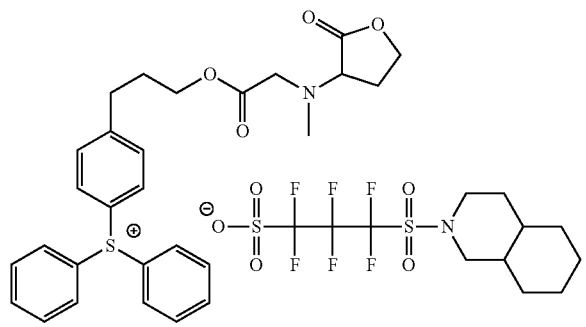
120
-continued
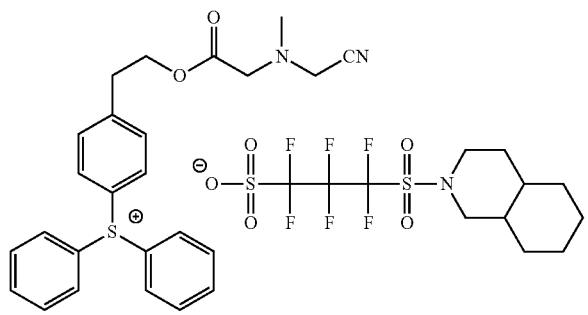
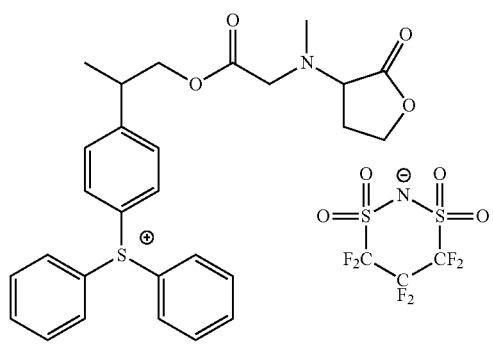
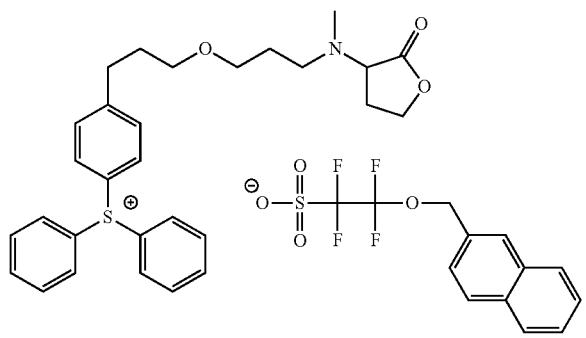
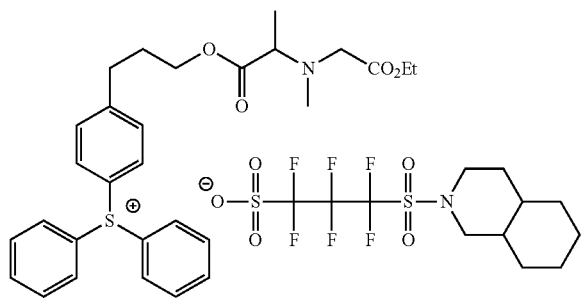
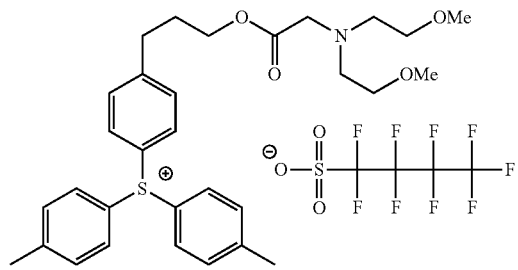

121
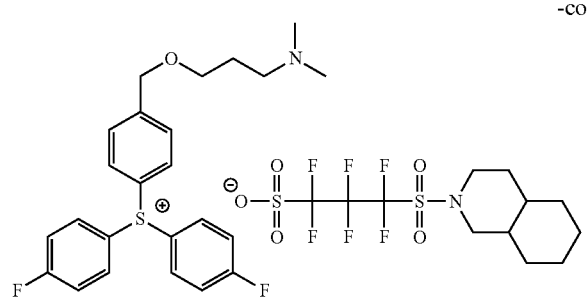
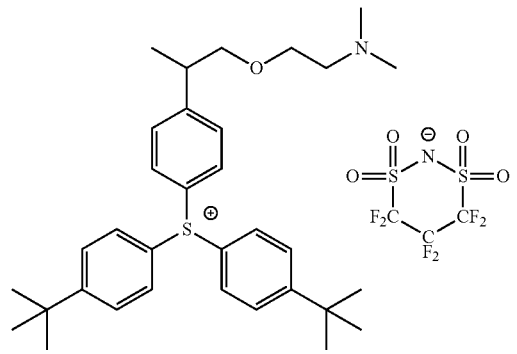
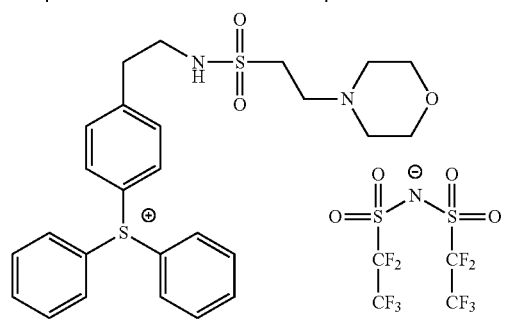
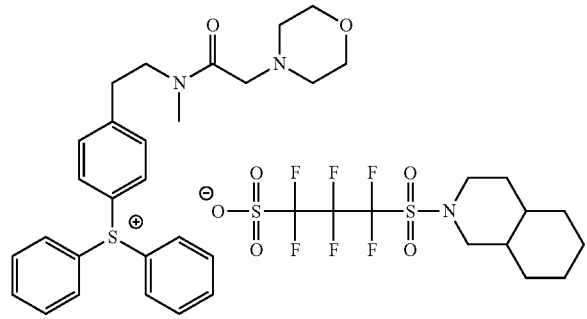
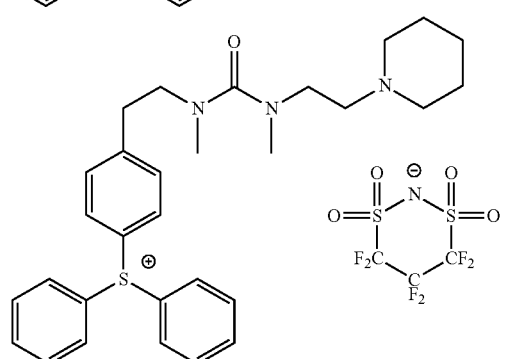
122
-continued
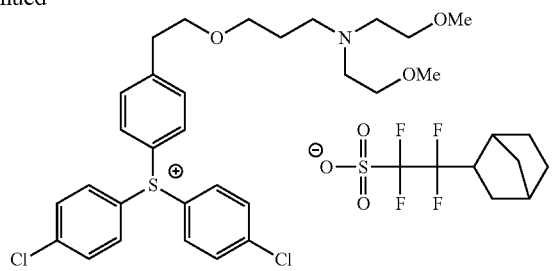
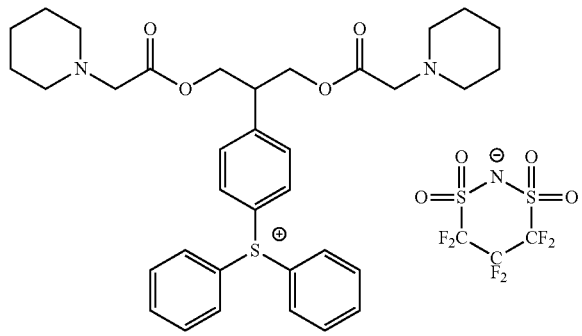
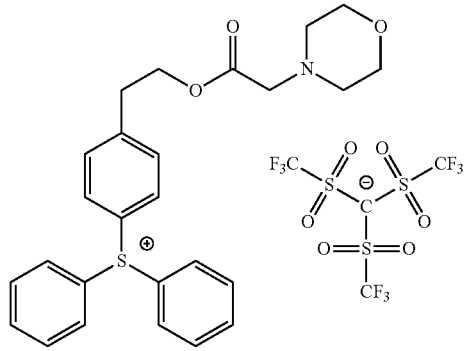
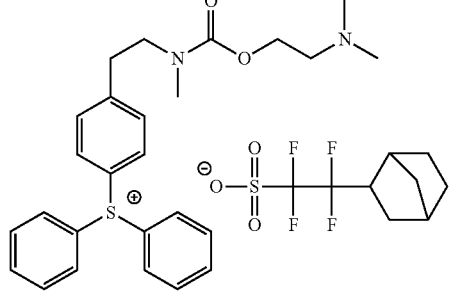
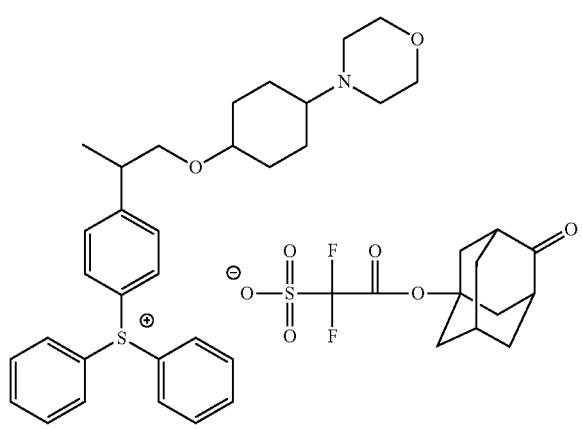

-continued
| 123 | 124 |
|---|---|
| 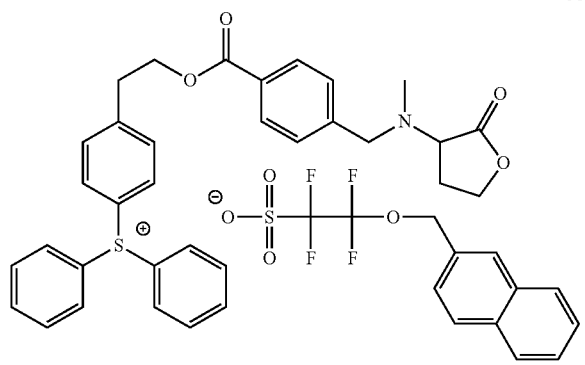 | 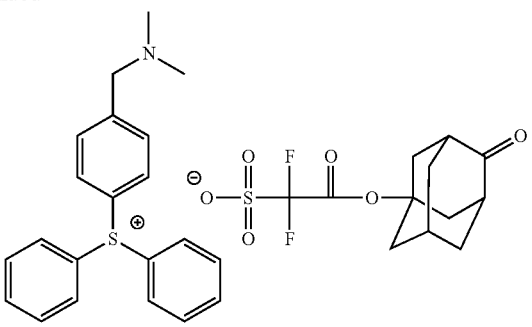 |
| 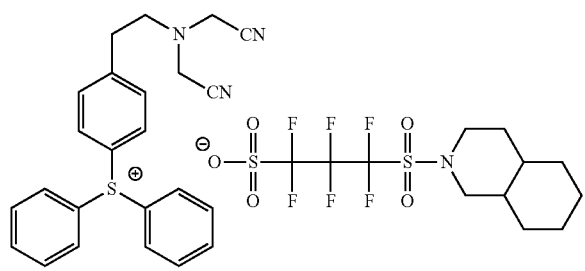 | 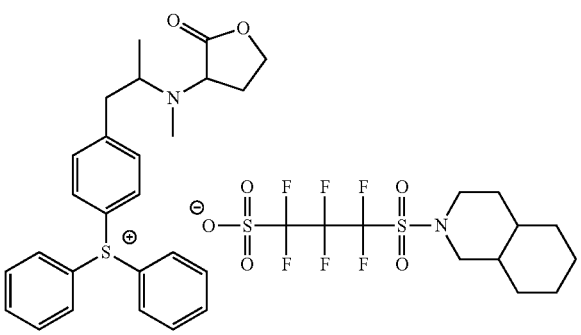 |
| 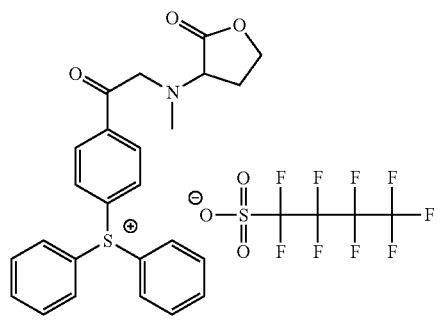 | 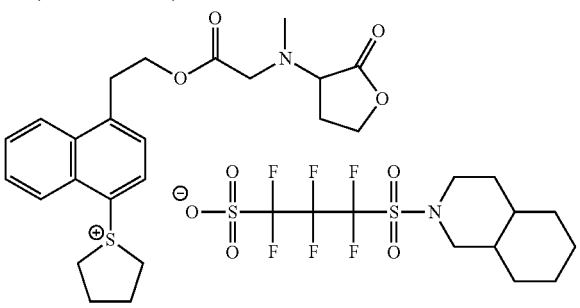 |
| 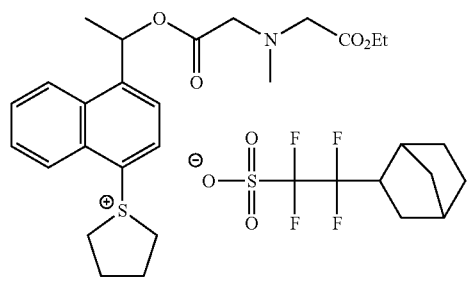 | 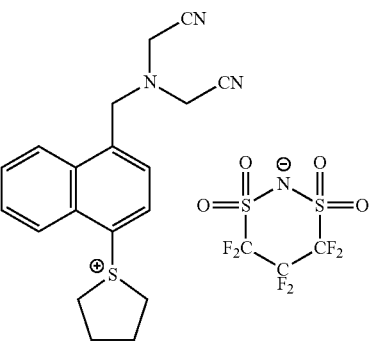 |
| 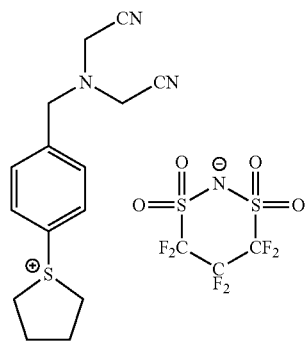 | 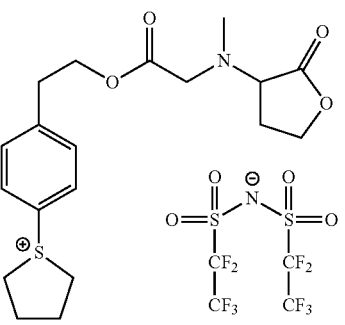 |

125
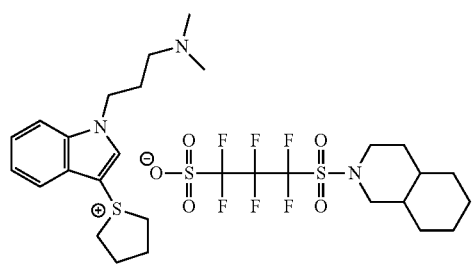
-continued
126
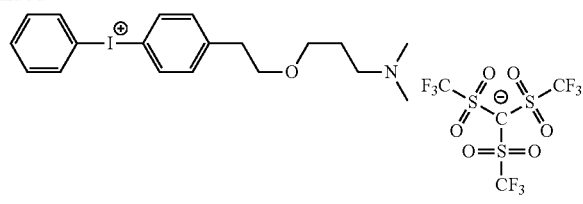
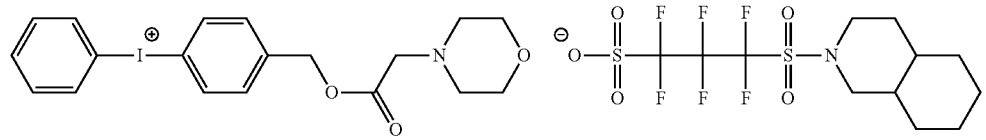
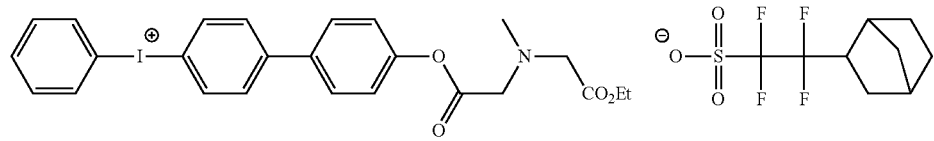
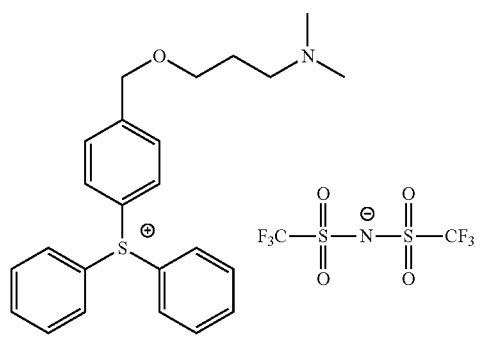
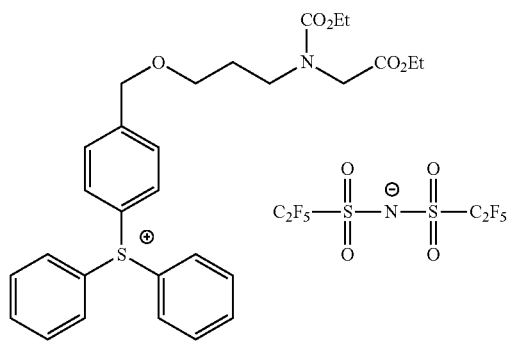
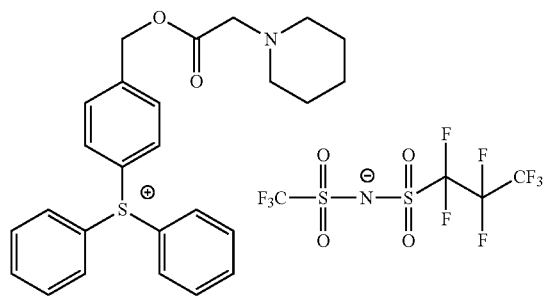
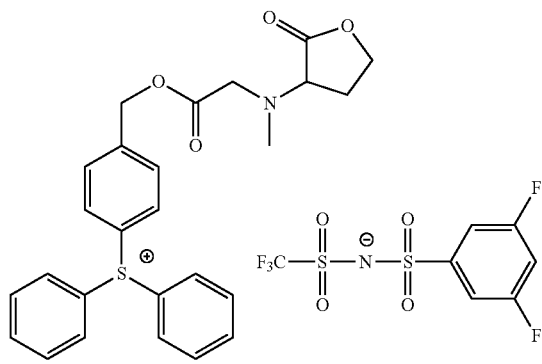
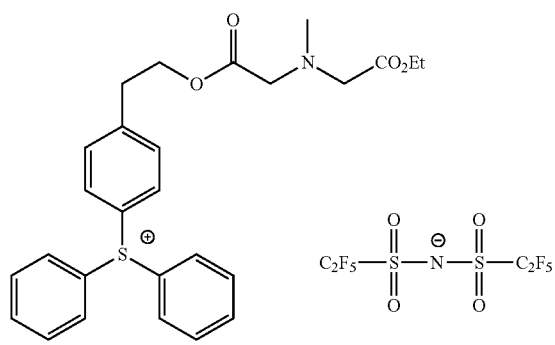
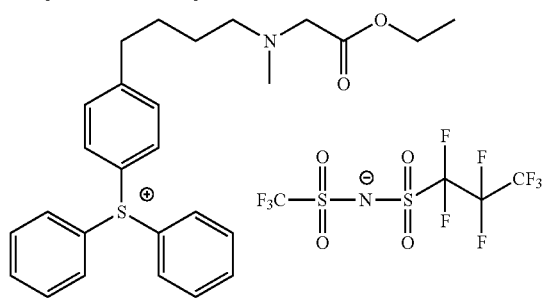

127
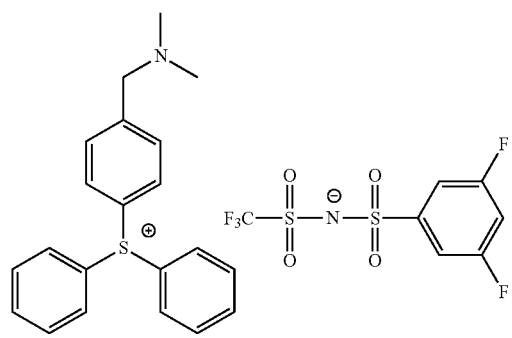
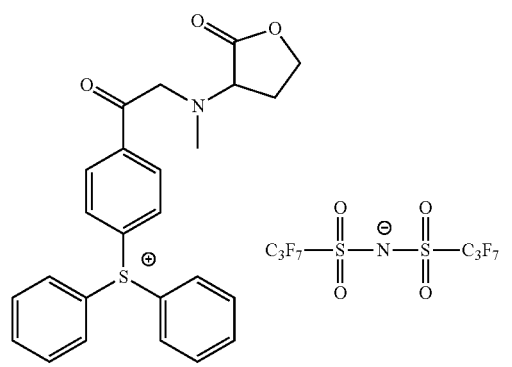
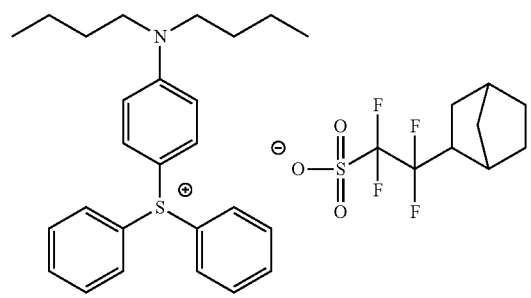
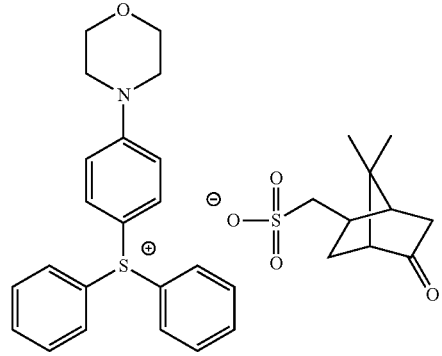
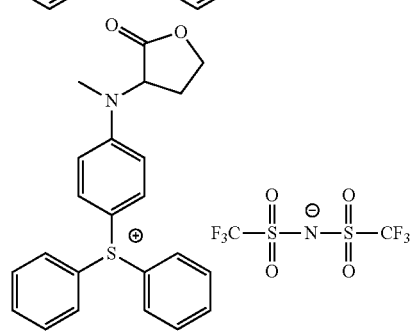
128
-continued
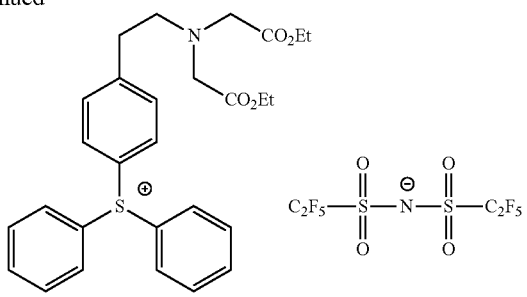
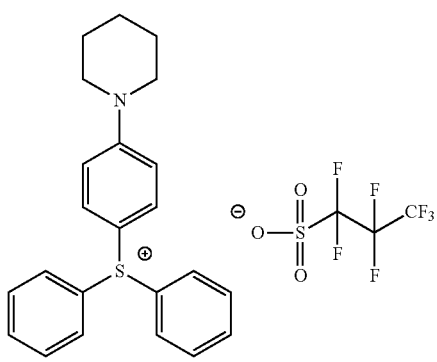
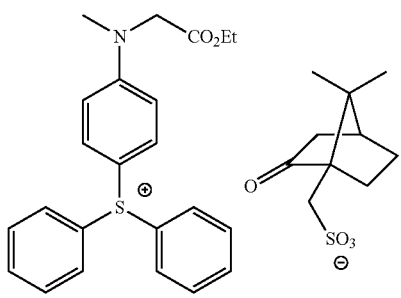
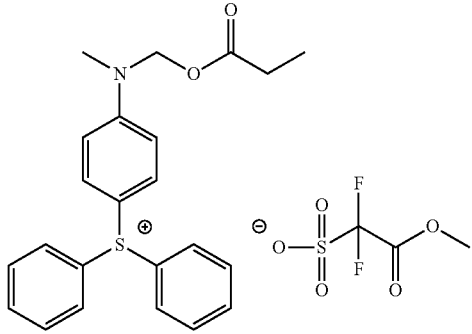
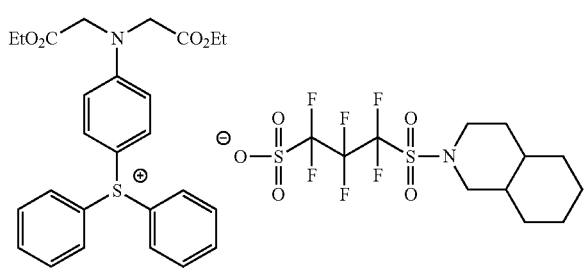

-continued
| 129 | 130 |
|---|---|
| 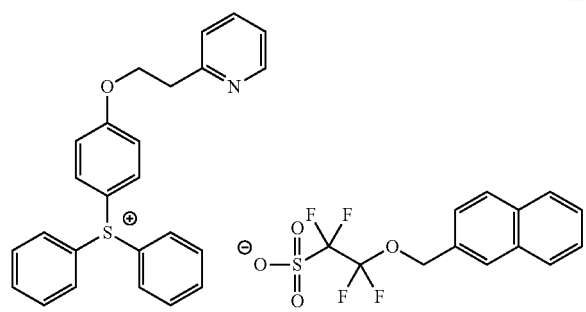 | 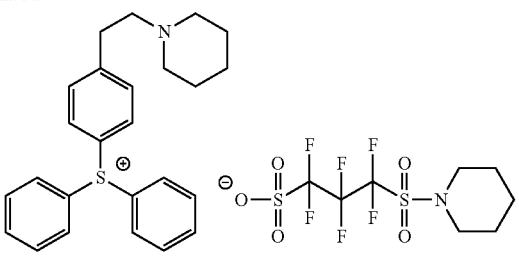 |
| 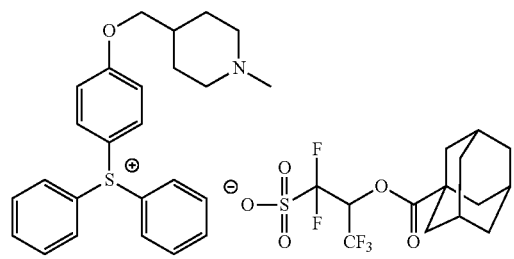 | 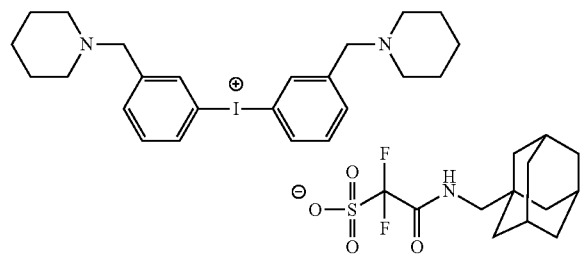 |
| 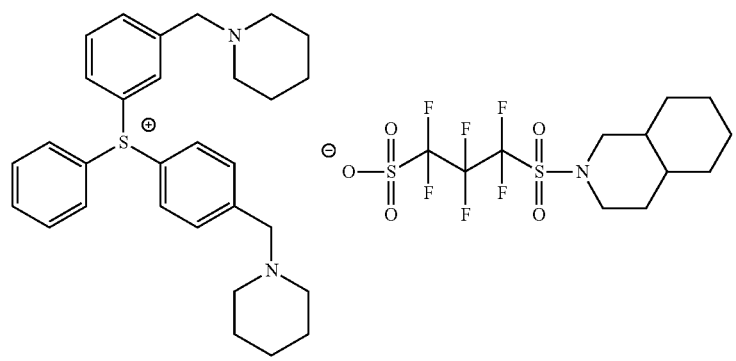 | |
| 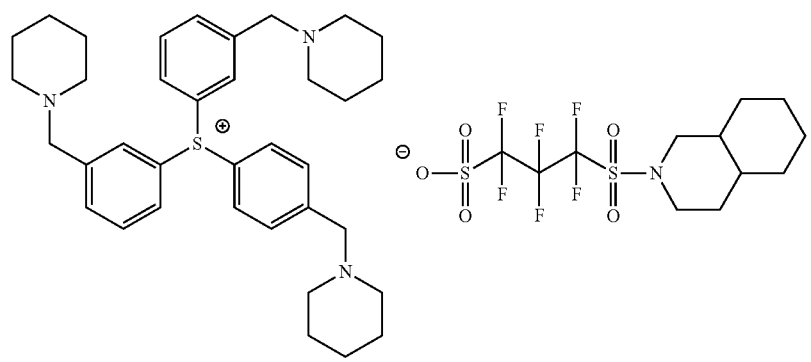 | |
| 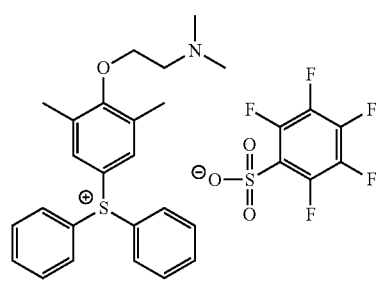 | 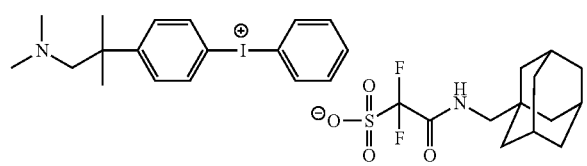 |

131
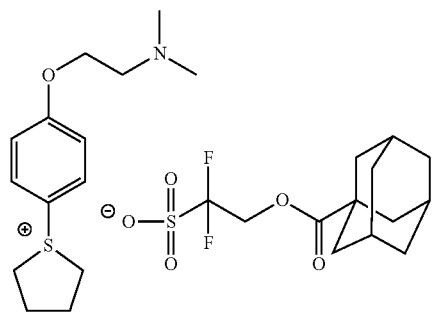
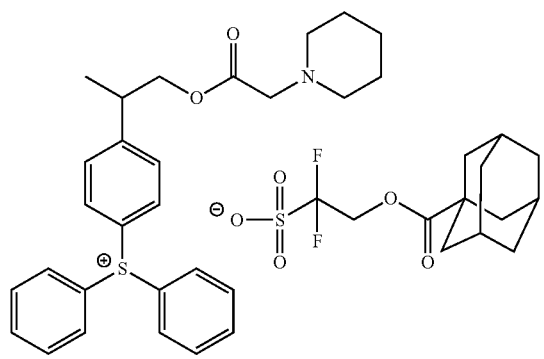
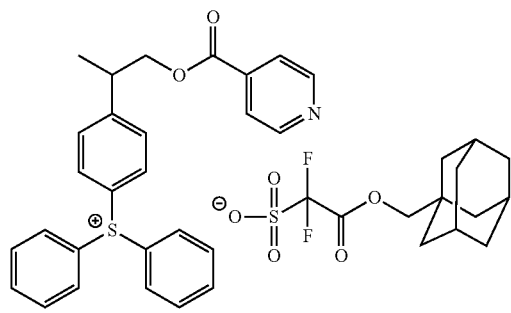
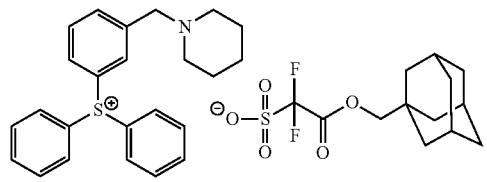
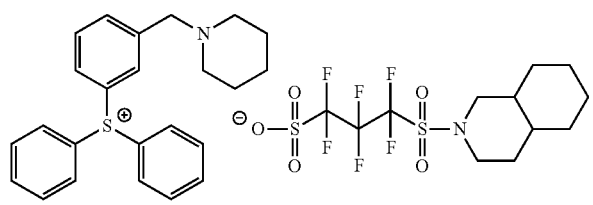
132
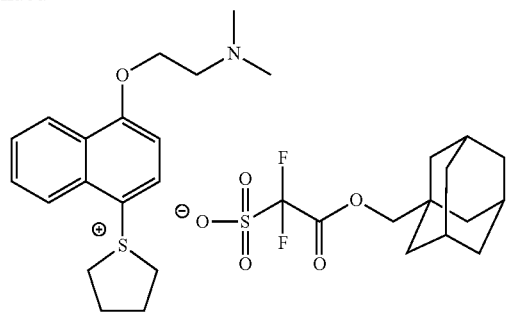
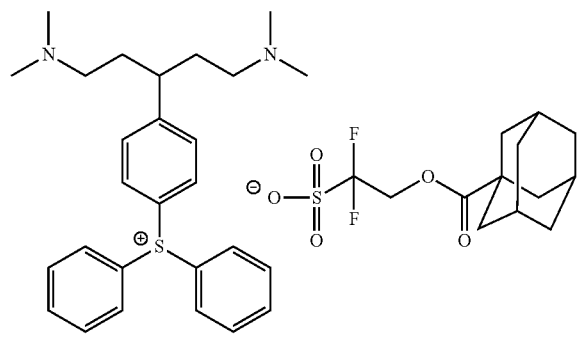
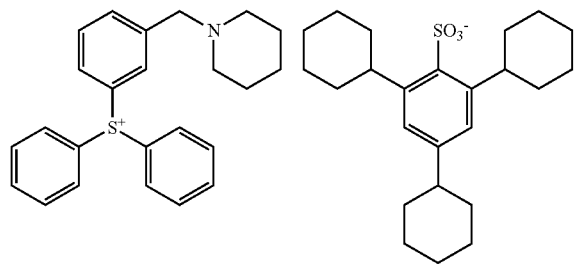
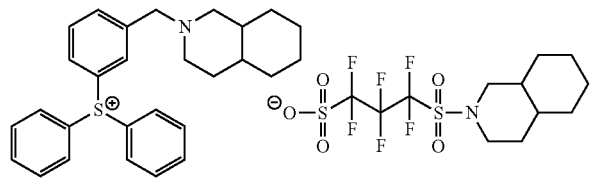
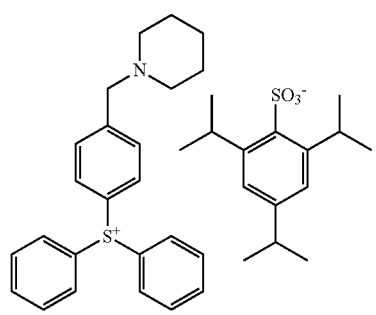

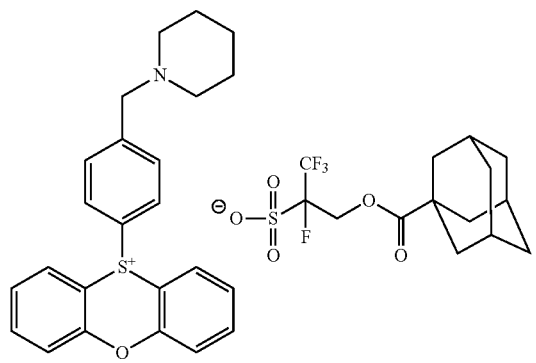
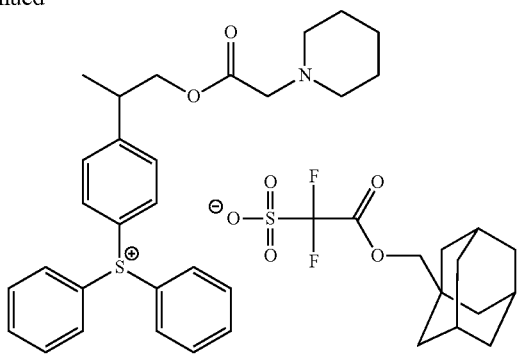

The compounds (D) may be used alone or two or more types may be used in combination.

The content of the compound (D) is typically within a range of 0.001% by mass to 10% by mass, preferably within a range of 0.1% by mass to 10% by mass, and more preferably 1% by mass to 10% by mass, based on the total solid content of the composition.

Moreover, it is preferable that the volume of the acid generated from the compound (D) is small, from the viewpoint of resolution improvement.

<Surfactant>

The composition of the present invention may further contain a surfactant to improve coating properties. The surfactant is not particularly limited, and examples thereof include nonionic surfactants such as polyoxyethylene alkyl ethers, polyoxyethylene alkyl allyl ethers, polyoxyethylene polyoxypropylene block copolymers, sorbitan fatty acid esters, and polyoxyethylene sorbitan fatty acid ester, fluorine-based surfactants such as Megafac (registered trademark) F171 and Megafac F176 (manufactured by DIC Corporation), Fluorad FC430 (manufactured by Sumitomo 3M Ltd.), and Surfynol E1004 (manufactured by Asahi Glass Co., Ltd.), and PF656 and PF6320 manufactured by OMNOVA Solutions Inc., an organosiloxane polymer, and a polysiloxane polymer.

In a case where the composition of the present invention contains a surfactant, the content of the surfactant is preferably 0.0001% by mass to 2% by mass and more preferably 0.0005% by mass to 1% by mass, with respect to the total amount (excluding the solvent) of the composition.

<Organic Carboxylic Acid>

The composition of the present invention preferably contains a organic carboxylic acid, in addition to the above components. Examples of such an organic carboxylic acid compound include aliphatic carboxylic acids, alicyclic carboxylic acids, unsaturated aliphatic carboxylic acids, oxycarboxylic acids, alkoxycarboxylic acids, ketocarboxylic acids, benzoic acid derivatives, phthalic acid, terephthalic acid, isophthalic acid, 2-naphthoic acid, 1-hydroxy-2-naphthoic acid, and 2-hydroxy-3-naphthoic acid, and when performing electron beam exposure in vacuum, there is a possibility that a compound is volatilized from the resist film surface, and due to this, the inside of the drawing chamber is contaminated, as a preferable compound, aromatic organic carboxylic acids, among these, benzoic acid, 1-hydroxy-2-naphthoic acid, and 2-hydroxy-3-naphthoic acid are suitable.

The blending ratio of the organic carboxylic acid is preferably 0.5% by mass to 15% by mass and more preferably 2% by mass to 10% by mass, with respect to the total solid content of the composition.

The composition of the present invention may further include a dye, a plasticizer, or an acid proliferative agent (described in WO95/29968A, WO98/24000A, JP1996-305262A (JP-H08-305262A), JP1997-34106A (JP-H09-34106A), JP1996-248561A (JP-H08-248561A), JP1996-503082A (JP-H08-503082A), U.S. Pat. No. 5,445,917A, JP1996-503081A (JP-H08-503081A), U.S. Pat. Nos. 5,534,393A, 5,395,736A, 5,741,630A, 5,334,489A, 5,582,956A, 5,578,424A, 5,453,345A, 5,445,917A, EP665,960B, EP757,628B, EP665,961B, U.S. Pat. No. 5,667,943A, JP1998-1508A (JP-H10-1508A), JP1998-282642A (JP-H10-282642A), JP1997-512498A (JP-H09-512498A), JP2000-62337A, JP2005-17730A, or JP2008-209889A), as necessary. As these compound, respective compounds described in JP 2008-268935A can be exemplified.

<Onium Salt of Carboxylic Acid>

The composition of the present invention may contain an onium salt of carboxylic acid. Examples of the onium carboxylate salt include a sulfonium salt of carboxylic acid, an iodonium salt of carboxylic acid, and an ammonium salt of carboxylic acid. In particular, the onium salt of carboxylic acid is preferably a sulfonium salt of carboxylic acid or an iodonium salt of carboxylic acid. Furthermore, in the present invention, the carboxylate residue of the onium salt of carboxylic acid preferably does not contain an aromatic group and a carbon-carbon double bond. Particularly preferable anion portion is a linear, branched, or monocyclic or polycyclic alkylcarboxylate anion having 1 to 30 carbon atoms. The anion is more preferably an anion of carboxylic acid in which the alkyl group is partially or entirely substituted with fluorine atoms. An oxygen atom may be included in the alkyl chain. Thus, the transparency with respect to light having a wavelength of 220 nm or less is ensured, the sensitivity and the resolving power are improved, and the density dependency and the exposure margin are improved.

The blending ratio of the onium salt of carboxylic acid is preferably 1% by mass to 15% by mass and more preferably 2% by mass to 10% by mass, with respect to the total solid content of the composition.

<Acid Proliferative Agent>

The active light sensitive or radiation sensitive resin composition of the present invention may further include one or two or more types of compound (hereinafter, referred to as an acid proliferative agent) that generates an acid by being decomposed due to the action of an acid. The acid generated by the acid proliferative agent is preferably sulfonic acid, methide acid, or imidic acid. The content of the acid proliferative agent is preferably 0.1% by mass to 50% by mass, more preferably 0.5% by mass to 30% by mass, and still more preferably 1.0% by mass to 20% by mass, based on the total solid content of the composition.

Although the ratio of the amount of acid proliferative agent and the amount of acid generator (solid content amount of an acid proliferative agent based on the total solid content in the composition/solid content amount of an acid generator based on the total solid content in the composition) is not particularly limited, the ratio is preferably 0.01 to 50, more preferably 0.1 to 20, and particularly preferably 0.2 to 1.0.

Examples of the acid proliferative agent which can be used in the present invention will be shown below, but the present invention is not limited thereto.

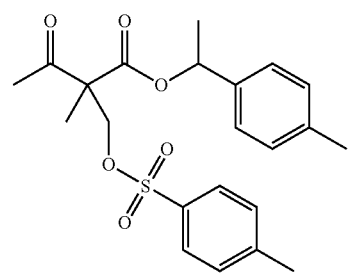
(PA-1)

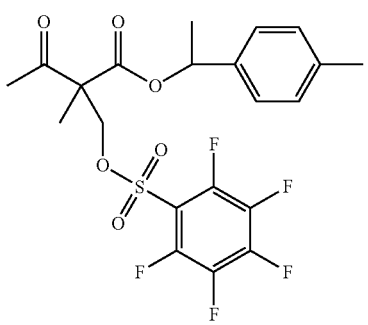
(PA-2)

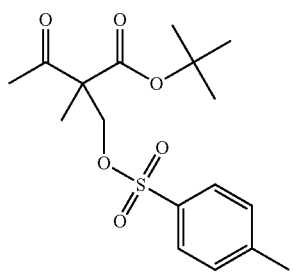
(PA-3)

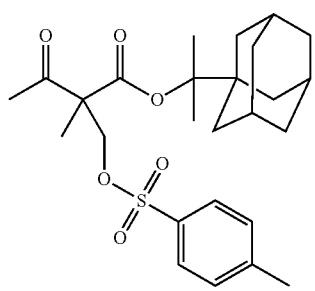
(PA-4)

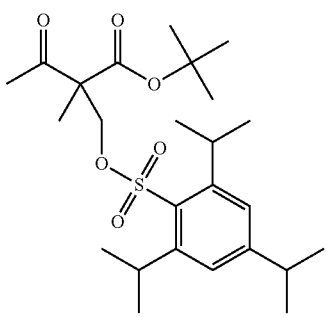
(PA-5)

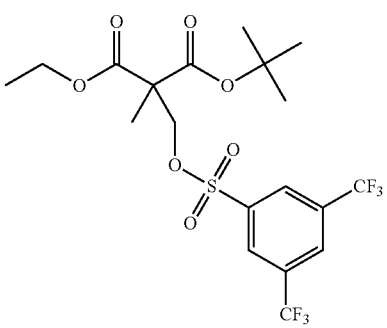
(PA-6)

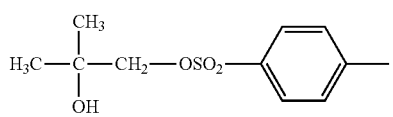
(PA-7)

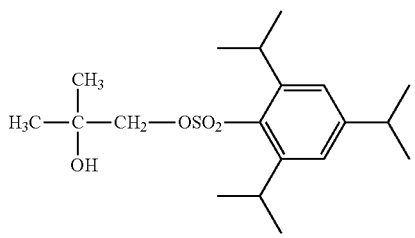
(PA-8)

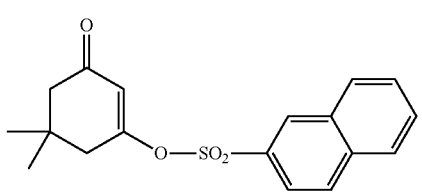
(PA-9)

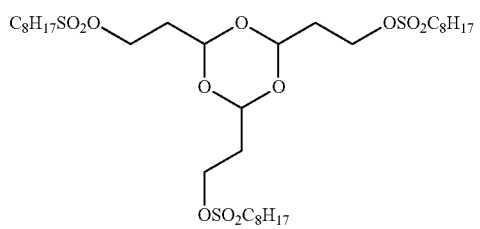
(PA-10)

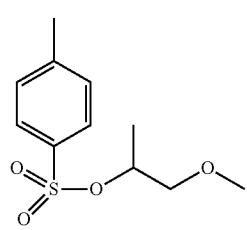
(PA-11)

-continued (PA-12) 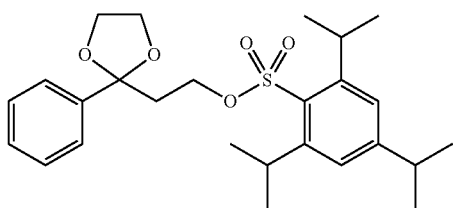

(PA-13) 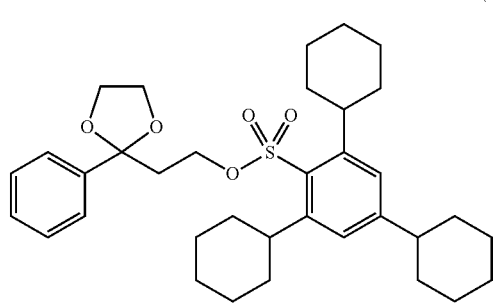

(PA-14) 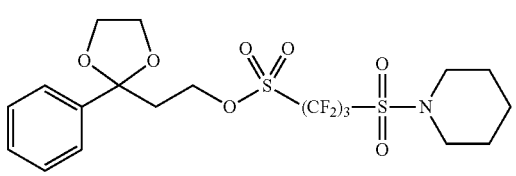

(PA-15) 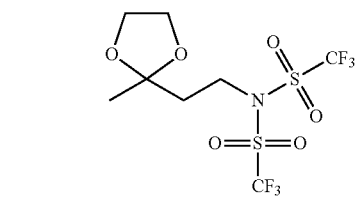

(PA-16) 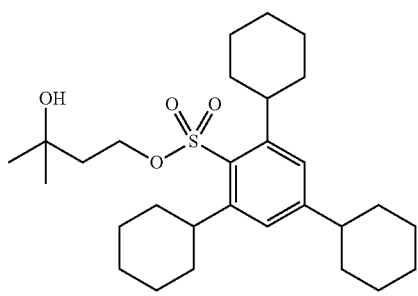

(PA-17) 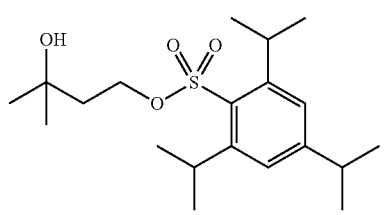

-continued (PA-18) 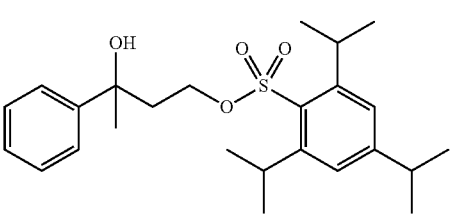

<Solvent>

The composition of the present invention may contain a solvent, and as the solvent, ethylene glycol monoethyl ether acetate, cyclohexanone, 2-heptanone, propylene glycol monomethyl ether (PGME, also referred to as 1-methoxy-2-propanol), propylene glycol monomethyl ether acetate (PGMEA, also referred to as 1-methoxy-2-acetoxypropane), propylene glycol monomethyl ether propionate, propylene glycol monoethyl ether acetate, methyl 3-methoxypropionate, ethyl 3-ethoxypropionate, methyl β-methoxyisobutyrate, ethyl butyrate, propyl butyrate, methylisobutyl ketone, ethyl acetate, isoamyl acetate, ethyl lactate, toluene, xylene, cyclohexyl acetate, diacetone alcohol, N-methylpyrrolidone, N,N-dimethylformamide, γ-butyrolactone, N,N-dimethylacetamide, propylene carbonate, ethylene carbonate, or the like is preferable. These solvents are used alone or in combination thereof.

The solid content of the composition of the present invention is preferably dissolved in the above-described solvent so as to become 1% by mass to 40% by mass as a solid content concentration. The solid content concentration is more preferable 1% by mass to 30% by mass, and still more preferably 3% by mass to 20% by mass.

<Active Light Sensitive or Radiation Sensitive Film and Mask Blank>

The present invention also relates to the active light sensitive or radiation sensitive film including the composition of the present invention, and such a film may be, for example, by applying the composition of the present invention to a support such as a substrate. The thickness of the film is preferably 0.02 μm to 0.1 μm. The composition is applied to a substrate by a suitable application method such as spin coat, roll coat, flow coat, dip coat, spray coat, or doctor coat, as the method of applying to a substrate, and spin coating is preferable, and the rotation speed is preferably 1000 rpm to 3000 rpm. The coating film is prebaked at 60° C. to 150° C. for 1 minute to 20 minutes, preferably 80° C. to 120° C. for 1 minute to 10 minutes, to form a thin film.

As the material configuring a substrate to be processed and the outermost surface layer, for example, in the case of a semiconductor wafer, a silicon wafer can be used, and examples of material which becomes the outermost layer include Si, $SiO_2$, SiN, SiON, TiN, WSi, BPSG, SOG, and an organic antireflection film.

In addition, the present invention also relates to a mask blank provided with the active light sensitive or radiation sensitive film obtained in the above manner. To obtain such a mask blank provided with the active light sensitive or radiation sensitive film, in the case of forming a pattern on a photomask blank for photomask production, as a transparent substrate to be used, transparent substrates such as quartz and calcium fluoride are exemplified. In general, necessary functional films such as a shielding film, an antireflection film, and a phase shift film, and additionally, an etching stopper film, and an etching mask film are laminated on the substrate. As the material of the functional film, a film containing silicon or a transition metal such as chromium, molybdenum, zirconium, tantalum, tungsten, titanium, or niobium is laminated. In addition, examples of the material used for the outermost layer include a material having silicon or a material containing oxygen and/or nitrogen in silicon as the main constituent material, a silicon compound material having a material containing a transition metal therein as the main constituent material, and a transition metal compound material having a material including a transition metal, in particular, one or more types of transition metal selected from chromium, molybdenum, zirconium, tantalum, tungsten, titanium, and niobium, or further including one or more elements selected from oxygen, nitrogen, and carbon therein, as the main constituent material.

The light shielding film may be a single layer, but is preferably a multi-layer structure where a plurality of material are coated and overlapped. In a case of a multi-layer structure, the thickness of the film for each single layer is not particularly limited, but is preferably 5 nm to 100 nm and is more preferably 10 nm to 80 nm. The thickness of the entire light shielding film is not particularly limited, but is preferably 5 nm to 200 nm, and more preferably 10 nm to 150 nm.

In the case of forming a pattern on a photomask blank having, in general, a material containing oxygen or nitrogen in chromium, among the these materials, in the outermost surface layer by using the composition, a so-called undercut shape which is a constriction shape formed in the vicinity of the substrate is likely to occur, but in the case of using the present invention, it is possible to improve the undercut problem compared to that in the related art.

Next, the active light sensitive or radiation sensitive film is irradiated with active light or radiation (preferably, an electron beam) (hereinafter, also referred to as "exposure") and is developed preferably after baking is performed (typically at 80° C. to 150° C. and more preferably at 90° C. to 130° C.). Thus, an excellent pattern can be obtained. Then, using the pattern as a mask, an appropriate etching process, ion implantation, and the like are performed and a fine semiconductor circuit, an imprint mold structure, and the like is formed.

The process of the case of manufacturing a mold for imprint by using the composition of the present invention is described in, for example, JP4109085B, JP2008-162101A, "Fundamentals of Nanoimprint and Technical Development/Application Deployment-Substrate Technique of Nanoimprint and Latest Application Deployment", edited by Yoshihiko Hirai (Frontier Publishing).

<Pattern Forming Method>

The composition of the present invention can be suitably used in a formation process of a negative-type pattern described below. That is, the composition of the present invention can be preferably used in a process including forming an active light sensitive or radiation sensitive film by applying the composition of the present invention to a substrate, irradiating (that is, exposure) the active light sensitive or radiation sensitive film with active light or radiation, and obtaining a negative-type pattern by developing the exposed film using a developer. As such a process, for example, the process described in JP2008-292975A or JP2010-217884A can be used.

The present invention also relates to a pattern forming method including exposing the active light sensitive or radiation sensitive film or a mask blank provided with this film and developing the exposed active light sensitive or radiation sensitive film or a mask blank provided with the exposed film. In the present invention, the exposure is preferably performed using an electron beam or extreme ultraviolet rays.

In exposure (pattern forming step) of the active light sensitive or radiation sensitive film in manufacture of precision integrated circuit elements, first, irradiation with an electron beam or extreme ultraviolet rays (EUV) is preferably performed on the active light sensitive or radiation sensitive film of the present invention in a pattern shape. In the case of an electron beam, exposure is performed such that the exposure amount becomes about 0.1 μC/cm$^2$ to 20 μC/cm$^2$, and preferably about 3 μC/cm$^2$ to 10 μC/cm$^2$, and in the case of extreme ultraviolet rays, exposure is performed such that the exposure amount becomes about 0.1 mJ/cm$^2$ to 20 mJ/cm$^2$, and preferably about 3 mJ/cm$^2$ to 15 mJ/cm$^2$. Next, post exposure bake is performed at 60° C. to 150° C. for 1 minute to 20 minutes, and preferably 80° C. to 120° C. for 1 minute to 10 minutes, on a hot plates, and then, developing, rinsing, and drying are performed, whereby a pattern is formed. Subsequently, development is performed by using a developer for 0.1 minutes to 3 minutes, and preferably 0.5 minutes to 2 minutes, by an ordinary method such as a dipping method, a puddle method, or a spray method.

As the developer, either one of an organic-based developer and alkali developer can be used. As the organic-based developer, a polar solvent such as an ester solvent (butyl acetate, ethyl acetate, or the like), a ketone solvent (2-heptanone, cyclohexanone, or the like), an alcohol-based solvent, an amide-based solvent, or an ether-based solvent, or a hydrocarbon-based solvent can be used. The water content of the entirety of the organic-based developer is preferably less than 10% by mass, and the developer more preferably does not contains water substantially. The surfactant or the basic compound described above may be suitably added to the organic-based developer.

As the alkali developer, typically, quaternary ammonium salts represented by tetramethylammonium hydroxide are used, and, in addition to these, an alkali aqueous solution of inorganic alkali, a primary amine, a secondary amine, a tertiary amine, an alcohol amine, or a cyclic amine can also be used. As the alkali developer, for example, alkali aqueous solutions such as inorganic alkalies including sodium hydroxide, potassium hydroxide, sodium carbonate, sodium silicate, sodium metasilicate, and ammonia water, primary amines including ethylamine and n-propylamine, secondary amines including diethylamine and di-n-butylamine, tertiary amines including triethylamine and methyldiethylamine, alcohol amines including dimethyl ethanolamine and triethanolamine, tetraalkylammonium hydroxide including tetramethylammonium hydroxide, tetraethyl ammonium hydroxide, tetrapropylammonium hydroxide, tetrabutylammonium hydroxide, tetrapentylammonium hydroxide, tetrahexylammonium hydroxide, tetraoctylammonium hydroxide, ethyltrimethylammonium hydroxide, butyltrimethylammonium hydroxide, methyltriamylammonium hydroxide, and dibutyldipentylammonium hydroxide, quaternary ammonium salts including trimethylphenylammonium hydroxide, trimethylbenzylammonium hydroxide, and triethylbenzylammonium hydroxide, and cyclic amines including pyrrole and piperidine can be used. A suitable amount of alcohol or a surfactant can also be added to the alkali aqueous solution and used. The alkali concentration of the alkali developer is typically 0.1% by mass to 20% by mass. The pH of the alkali developer is typically 10.0 to 15.0. The alkali concentration and the pH of the alkali developer can be suitably adjusted and used. A surfactant or an organic solvent may be added to the alkali developer and used.

Since the composition of the present invention is a negative-type active light sensitive or radiation sensitive resin composition used for forming a negative-type pattern, the layer of the unexposed portion is dissolved, and the exposed portion is less likely to be dissolved in a developer by cross-linking of the compound. Using this, a desired patter can be formed on a substrate.

In addition, the present invention also relates to a method for manufacturing an electronic device including the pattern forming method of the present invention described above and an electronic device manufactured by the manufacturing method.

The electronic device of the present invention is suitably mounted on electrical and electronic equipment (home electrical appliances, OA and media-related equipment, optical equipment, communication equipment, or the like).

EXAMPLES

Hereinafter, the present invention will be described in further detail using examples, but the content of the invention is not limited thereto.

Synthesis of Cross-Linking Agent (C)

Synthesis Example: Synthesis of Compound C-1

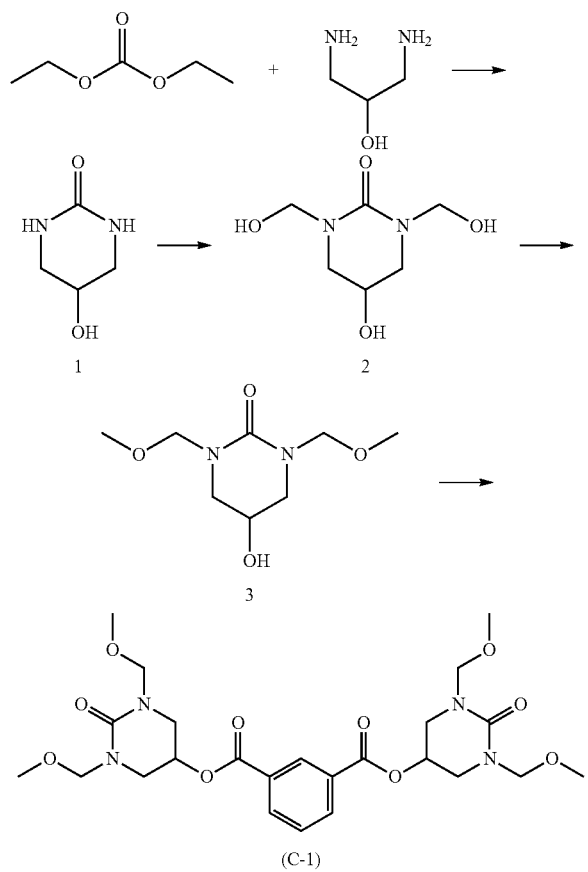

Synthesis of Compound 1

A compound 1 was synthesized by the method described in paragraphs "0119" and "0120" of JP2012-31233A.

Synthesis of Compound 3

The compound 1 (50 g) and paraformaldehyde (39 g) were mixed in DMAc (250 g) in a 2 L eggplant flask, and the pH of the reaction liquid was adjusted to 10 by adding a 1 N sodium hydroxide aqueous solution thereto. This mixture was stirred at room temperature for 3 hours, and production of a compound 2 was confirmed by NMR.

Methanol (500 g) was added to the reaction liquid including the obtained compound 2, and the pH of the reaction liquid was adjusted to 2 by adding concentrated sulfuric acid while ice-cooling. This reaction liquid was further stirred at room temperature for 1 hour, and production of a compound 3 was confirmed by NMR.

After 200 g of a saturated sodium bicarbonate water was added to this reaction liquid, the methanol was removed by distillation under reduced pressure, then, extraction from the aqueous layer was performed using ethyl acetate (200 g x 5), and the obtained organic layers were combined and concentrated, whereby 240 g of a DMAc solution containing 27% of the compound 3 was obtained as a crude product. The obtained compound 3 was used in the following reaction without purification.

Synthesis of Compound C-1

The compound 3 (55 g, as a 27% solution), DMAc (60 g), and pyridine (17.5 g) were mixed in an 500 mL eggplant flask, and the resultant product was cooled with ice. Isophthalic acid chloride (7.5 g) was added thereto, and the resultant product was stirred for 30 minutes while being cooled with ice, and further stirred at room temperature for 1 hour. 50 g of water and 400 g of ethyl acetate were added to the obtained reaction solution to be liquid-liquid separated, and the organic layer was concentrated.

The obtained crude product was purified by column chromatography, whereby a compound C-1 (12 g) was obtained as a red crystal. The NMR chart (DMSO-d6) of the compound C-1 is shown in FIG. 1.

Synthesis of Compound C-2

Figure 2:
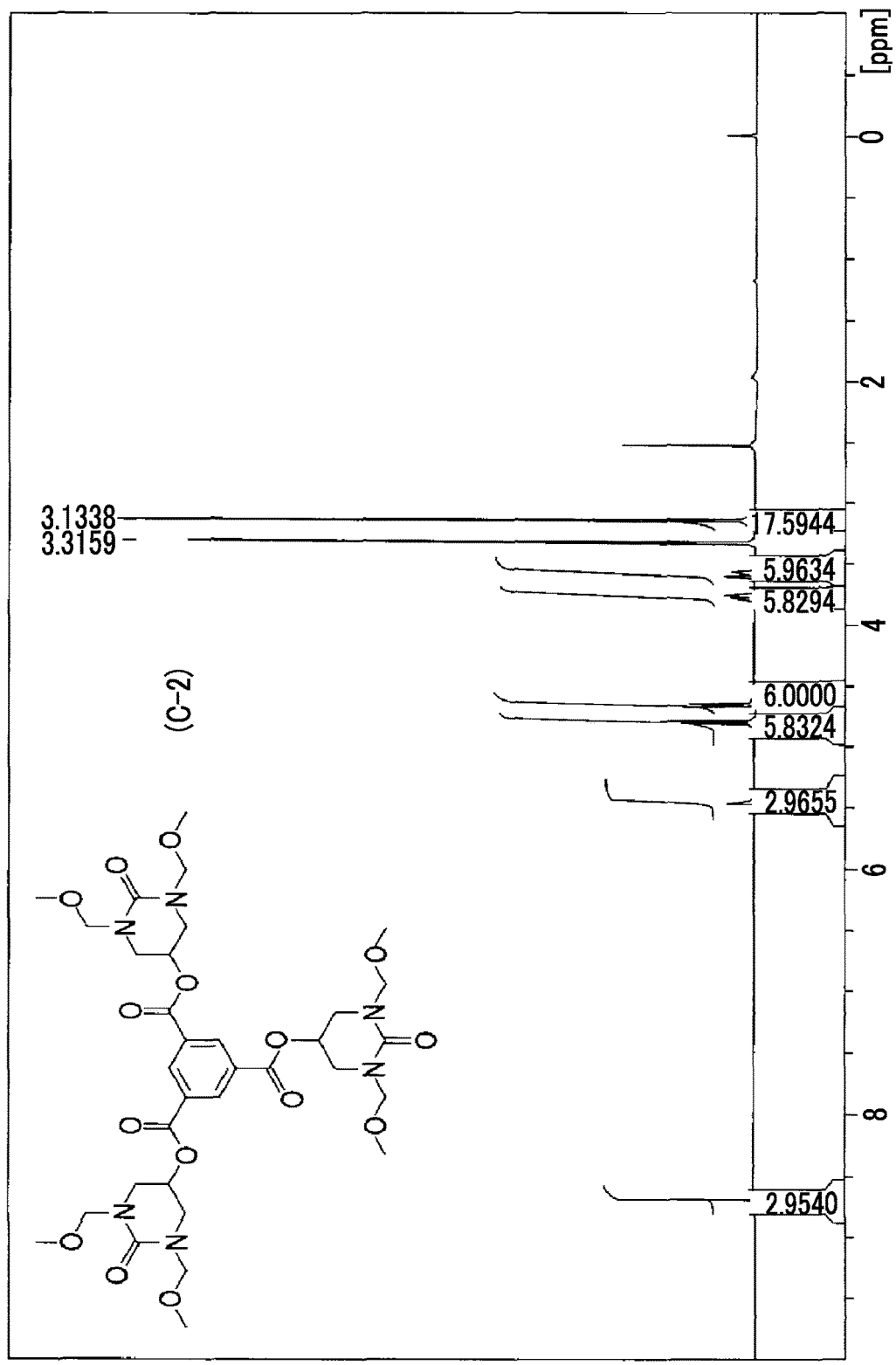
FIG. 2 is a view showing an NMR chart (DMSO-d6) of a compound (C-2) synthesized in the example.

A compound C-2 shown below was synthesized in the same manner as in the compound C-1. The NMR chart (DMSO-d6) of the compound C-2 is shown in FIG. 2.

Synthesis of Compound C-3

Figure 3:
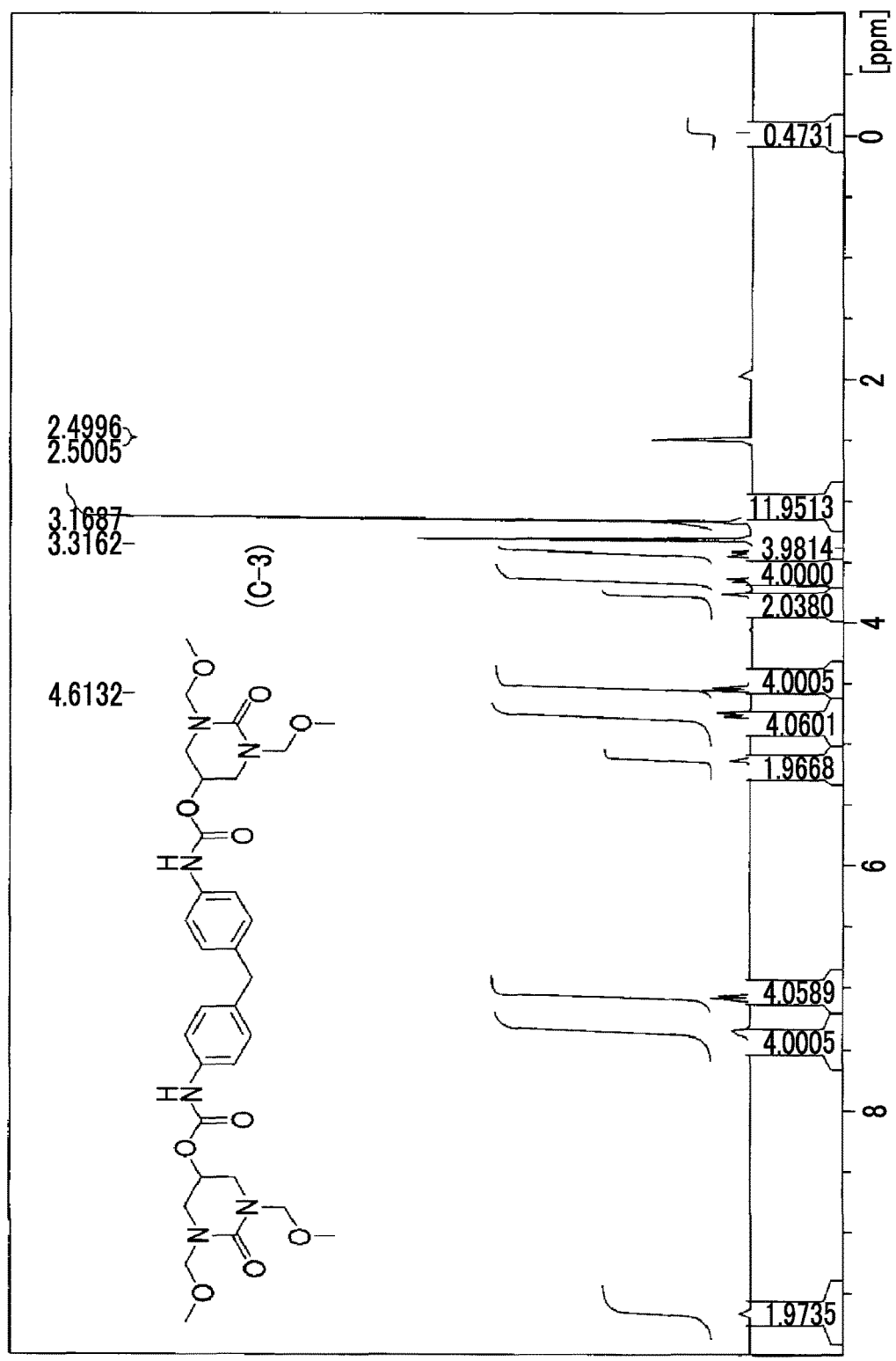
FIG. 3 is a view showing an NMR chart (DMSO-d6) of a compound (C-3) synthesized in the example.

A compound C-3 shown below was synthesized in the same manner as in the compound C-1. The NMR chart (DMSO-d6) of the compound C-3 is shown in FIG. 3.

Synthesis of Compound C-4

Figure 4:
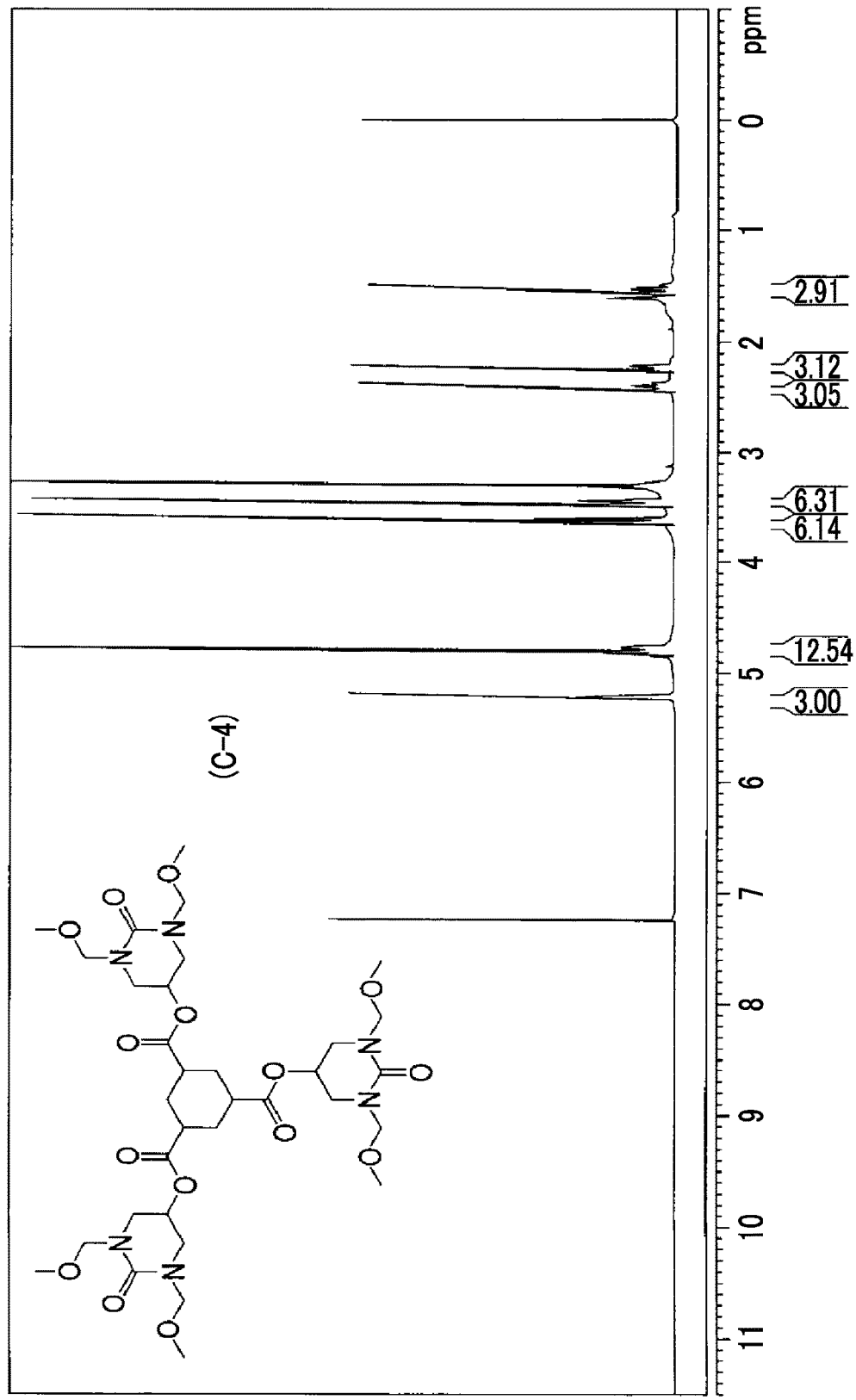
FIG. 4 is a view showing an NMR chart (CDCl3) of a compound (C-4) synthesized in the example.

A compound C-4 shown below was synthesized in the same manner as in the compound C-1. The NMR chart (CDCl3) of the compound C-4 is shown in FIG. 4.

Synthesis of Compounds C-5 to C-7

Compounds C-5 to C-7 shown below were synthesized in the same manner as in the compound C-1.

Moreover, compounds C-8 and C-9 were as a control.

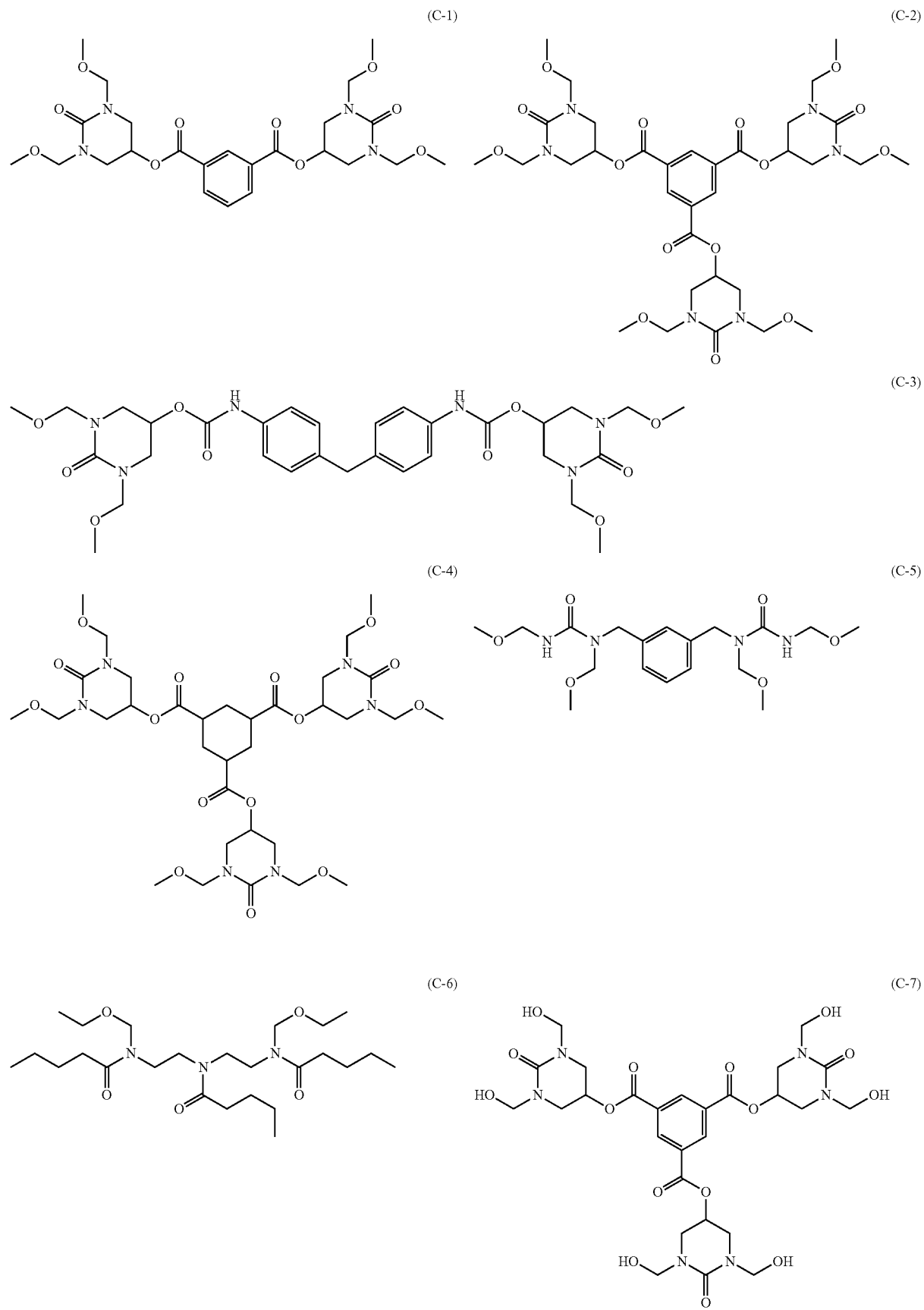

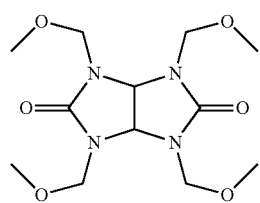

(C-8)

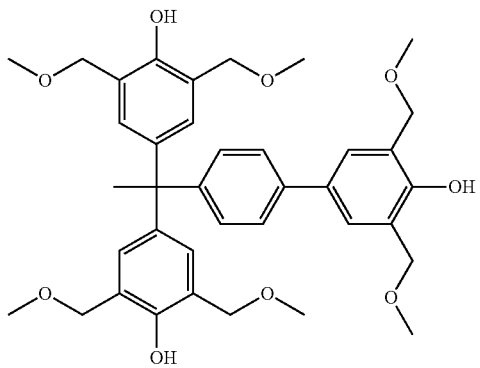

(C-9)

<Alkali Soluble Resin>

As an alkali soluble resin, resins (P-1) to (P-7) shown below were used. The resins are shown below with the compositional ratio (molar ratio), the weight average molecular weight Mw, and the dispersity Mw/Mn. Here, the weight average molecular weight Mw (in terms of polystyrene), the number average molecular weight Mn (in terms of polystyrene), and the dispersity Mw/Mn were calculated by GPC measurement. In addition, the compositional ratio (molar ratio) was calculated by 1H-NMR measurement. GPC measurement was performed by using HLC-8120 (manufactured by Tosoh Corporation), TSK gel Multipore HXL-M (manufactured by Tosoh Corporation, 7.8 mm HD×30.0 cm) as a column, and THF (tetrahydrofuran) or NMP (N-methyl-2-pyrrolidone) as an eluent.

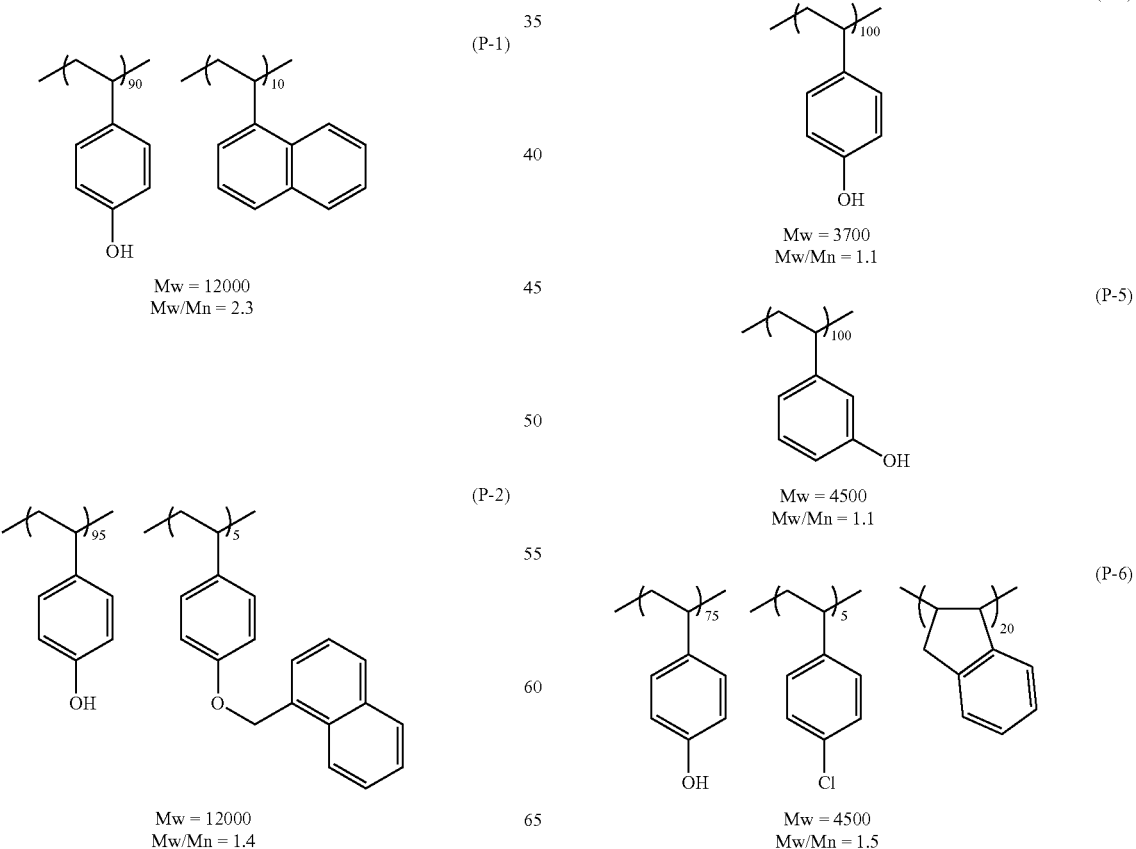

-continued
(P-7)
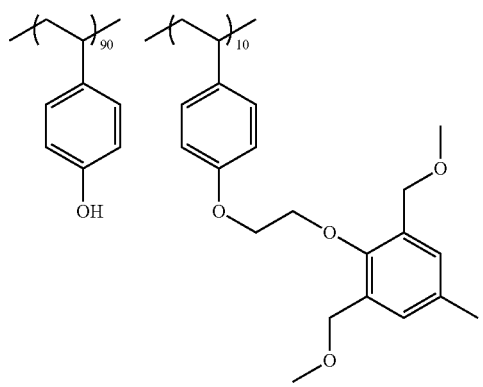
Mw = 4100
Mw/Mn = 1.1
<Acid Generator>
As an acid generator, compounds PAG-1 to PAG-5 shown below were used.
(PAG-1)
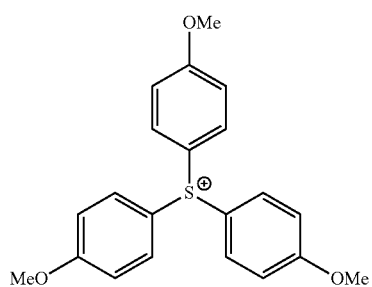
(PAG-2)
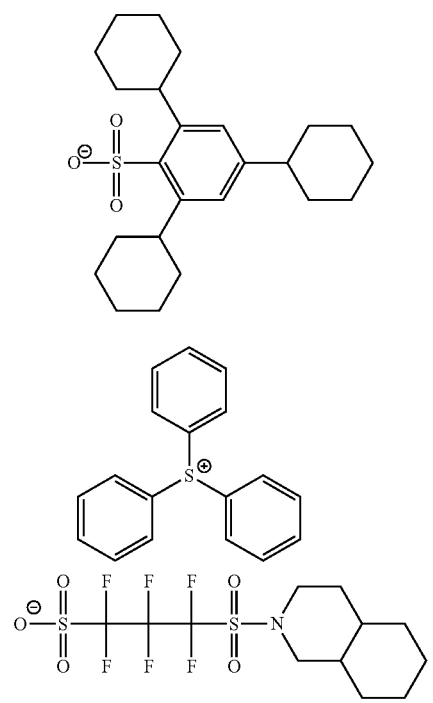
-continued
(PAG-3)
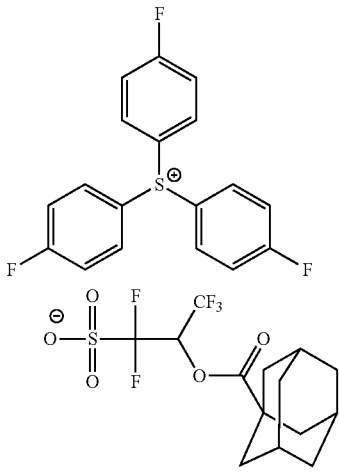
(PAG-4)
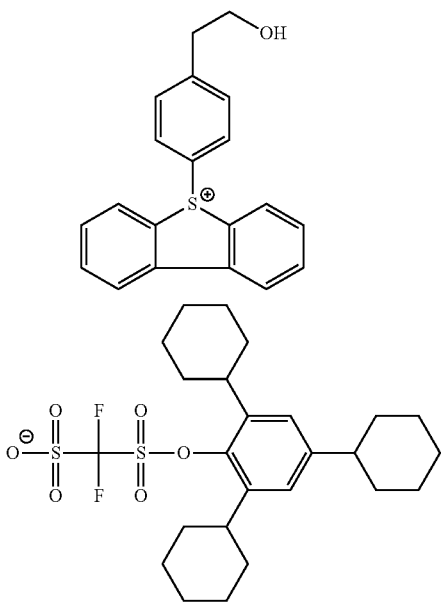
(PAG-5)
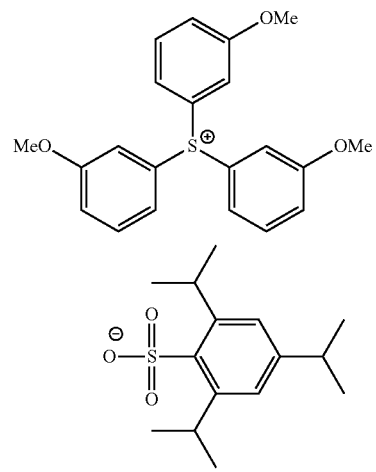
<Basic Compound>
As a basic compound, compounds D-1 to D-5 shown below were used.

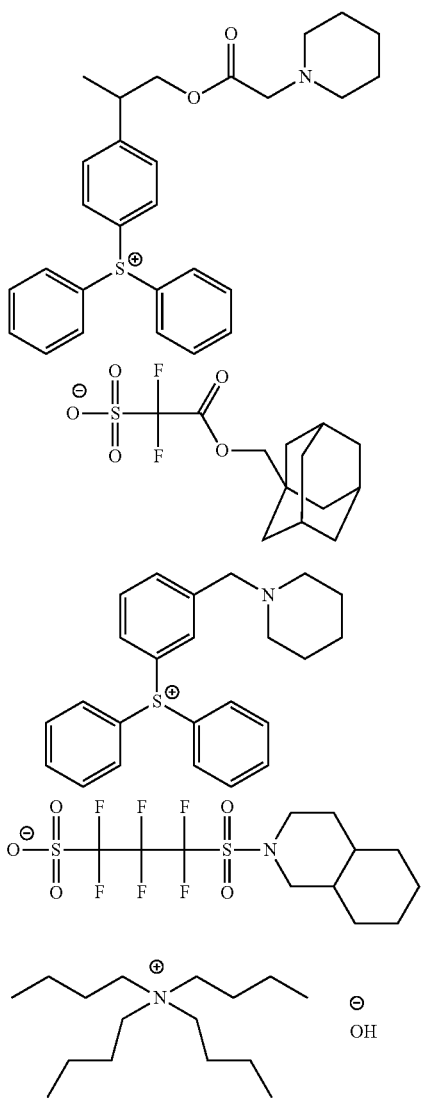

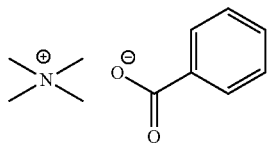

<Additive>
E1: 2-hydroxy-3-naphthoic acid
E2: 2-naphthoic acid
E3: benzoic acid
<Surfactant>
W-1: PF6320 (manufactured by OMNOVA Solutions Inc.)
W-2: Megafac F176 (manufactured by DIC Corporation; fluorine-based surfactant)
W-3: polysiloxane polymer KP-341 (manufactured by Shin-Etsu Chemical Co., Ltd.; silicon-based surfactant)
<Solvent>
S1: propylene glycol monomethyl ether (1-methoxy-2-propanol)
S2: propylene glycol monomethyl ether acetate (1-methoxy-2-acetoxypropane)
S3: 2-heptanone
S4: ethyl lactate
S5: cyclohexanone
S6: γ-butyrolactone
S7: propylene carbonate
<EB Exposure; Negative-Type; and Alkali Development>
[Preparation of Support]
As a support, a 6-inch wafer (which had been subjected to a shielding film treatment used for a typical photomask blank) on which chrome oxide had been deposited was prepared.
[Preparation of Resist Coating Solution]
Each solution having a total solid concentration of 4.0% by mass was prepared by dissolving the components shown in the following table in a solvent, and this was filtered by using a polytetrafluoroethylene filter with a pore size of 0.04 µm, whereby a resist solution was prepared.

TABLE 1

| Resist composition | | | | | | | |
|---|---|---|---|---|---|---|---|
| Resist composition | Resin | Acid (g) generator | Basic (g) compound | (g) | Cross-linking agent | (g) | Additive |
| R-1 | P-1 | 10 PAG-1 | 2.7 D-1 | 0.5 | C-1 | 4.2 | E-1 |
| R-2 | P-2 | 10 PAG-2 | 2.4 D-2 | 0.5 | C-2 | 4.1 | |
| R-3 | P-3 | 10 PAG-3 | 2.3 D-3 | 0.3 | C-3 | 4.3 | E-2 |
| R-4 | P-4 | 10 PAG-4 | 2.8 D-4 | 0.4 | C-4 | 4.2 | |
| R-5 | P-5 | 10 PAG-5 | 3 D-5 | 0.4 | C-5 | 4.8 | |
| R-6 | P-6 | 5/5 PAG-5 | 2.9 D-2 | 0.5 | C-3 | 4.3 | |
| R-7 | P-7 | 10 PAG-5 | 2.5 D-3 | 0.2 | C-7 | 4.2 | E-3 |
| R-8 | P-3/P-4 | 8/2 PAG-3 | 1.9 D-1 | 0.5 | C-2 | 4.2 | |
| R-9 | P-1 | 10 PAG-4 | 2.1 D-4 | 0.2 | C-1/C-9 | 2.1/2.1 | |
| R-10 | P-2 | 10 PAG-1 | 2.3 D-5 | 0.5 | C-3 | 4.1 | E-2 |
| R-11 | P-3 | 10 PAG-4 | 2.4 D-3 | 0.4 | C-4 | 4.3 | |
| R-12 | P-2/P-7 | 5/5 PAG-2 | 2.6 D-4 | 0.5 | C-6 | 4.2 | E-3 |
| R-13 | P-6 | 10 PAG-3 | 2.7 D-5 | 0.5 | C-1/C-4 | 3/1.2 | |

TABLE 1-continued

Resist composition

| | Acid-decomposable resin | | | | | | | |
|---|---|---|---|---|---|---|---|---|
| R-14 | P-1 | 10 | PAG-1 | 2.7 | D-1 | 0.5 | C-8 | 4.2 E-1 |

| Resist composition | (g) | Surfactant | (g) | Solvent | (mass ratio) | Solid content concentration (% by weight) |
|---|---|---|---|---|---|---|
| R-1 | 0.2 | W-2 | 0.05 | SL-3/SL-6 | 70/30 | 4.0 |
| R-2 | | W-3 | 0.05 | SL-1/SL-5 | 60/40 | 4.0 |
| R-3 | 0.3 | W-2 | 0.05 | SL-1/SL-5 | 80/20 | 4.0 |
| R-4 | | W-3 | 0.05 | SL-3/SL-4 | 80/20 | 4.0 |
| R-5 | | W-2 | 0.05 | SL-1/SL-5/SL-7 | 70/20/10 | 4.0 |
| R-6 | | W-3 | 0.05 | SL-1/SL-5 | 80/20 | 4.0 |
| R-7 | 0.3 | W-1 | 0.05 | SL-1/SL-5 | 70/30 | 4.0 |
| R-8 | | W-1 | 0.05 | SL-1/SL-6 | 80/20 | 4.0 |
| R-9 | | W-1 | 0.05 | SL-1/SL-5 | 60/40 | 4.0 |
| R-10 | 0.3 | W-1 | 0.05 | SL-3/SL-6 | 90/10 | 4.0 |
| R-11 | | W-1 | 0.05 | SL-2/SL-7 | 90/10 | 4.0 |
| R-12 | 0.3 | W-3 | 0.05 | SL-1/SL-5 | 60/40 | 4.0 |
| R-13 | | W-3 | 0.05 | SL-1/SL-7 | 90/10 | 4.0 |
| R-14 | 0.2 | W-2 | 0.05 | SL-3/SL-6 | 70/30 | 4.0 |

[Manufacture of Resist Film]

This resist coating solution was applied to the 6-inch wafer on which chrome oxide had been deposited using a spin coater Mark 8 manufactured by Tokyo Electron Limited, and dried on a hot plate at 110° C. for 90 seconds, whereby a resist film having a thickness of 50 nm was obtained. That is, a resist-coated mask blank was obtained.

[Manufacture of Negative-Type Resist Pattern]

Pattern irradiation was performed on the resist film using an electron beam lithography device (ELS-7500 manufactured by ELIONIX INC. acceleration voltage of 50 keV). After irradiation, the resultant product was heated on a hot plate at 110° C. for 90 seconds, immersed in a 2.38% by mass tetramethylammonium hydroxide (TMAH) aqueous solution for 60 seconds, rinsed with water for 30 seconds, and dried.

[Evaluation of Resist Pattern]

Evaluations of the sensitivity, the resolving power, the pattern shape, and the line edge roughness (LER) were performed on the obtained pattern by the following methods.

[Sensitivity]

The sectional shape of the obtained pattern was observed by using a scanning electron microscope (S-4300 manufactured by Hitachi, Ltd.). The exposure amount when the resist pattern of the line and space in a ratio of 1:1 having a line width of 50 nm was resolved was taken as sensitivity. A smaller value indicates higher sensitivity.

[L/S Resolving Power]

The marginal resolving power (a minimum line width at which a line and a space (line:space=1:1) are separately resolved) at the exposure amount at which the above sensitivity was exhibited was taken as L/S resolving power (nm).

[Pattern Shape]

A sectional shape of the line and space pattern in a ratio of 1:1 having a line width of 50 nm at the exposure amount at which the above sensitivity was exhibited was observed using a scanning electron microscope (S-4300 manufactured by Hitachi, Ltd.). In the sectional shape of the line pattern, a case where the ratio represented by [line width at the top portion (surface portion) of a line pattern/line width at the center portion (height position at half the height of a line pattern) of a line pattern] was less than 0.85 was evaluated as "taper", a case where the ratio was less than 0.95 and 0.85 or greater was evaluated as "slightly taper", and a case where the ratio was 0.95 or greater and 1.05 or less was evaluated as "rectangle".

[Isolated Space Pattern Resolving Power]

The marginal resolving power (a minimum space width at which a line and a space are separately resolved) of an isolated space (line:space=100:1) in the above sensitivity was determined. This value was taken as "isolated space pattern resolving power (nm)". A smaller value indicates a better performance.

[Line Edge Roughness (LER)]

At the exposure amount at which the above sensitivity was exhibited, a line and space pattern in a ratio of 1:1 having a line width of 50 nm was formed. For arbitrary 30 points included in the longitudinal direction of 50 pin, a distance from a base line where the edge was supposed to be present was measured using a scanning electron microscope (S-9220 manufactured by Hitachi, Ltd.). The standard deviation of the distance was determined, and 3σ was calculated. A smaller value indicates a better performance.

TABLE 2

EB/alkali development/negative

| Examples | Resist composition | Sensitivity (μC/cm$^2$) | LS resolving power [nm] | Pattern shape | Isolated space pattern resolving power [nm] | LER [nm] |
|---|---|---|---|---|---|---|
| Example 1 | R-1 | 20.4 | 20 | Rectangular | 25 | 4.0 |
| Example 2 | R-2 | 21.1 | 20 | Rectangular | 25 | 4.1 |

TABLE 2-continued

EB/alkali development/negative

| Examples | Resist composition | Sensitivity ($\mu C/cm^2$) | LS resolving power [nm] | Pattern shape | Isolated space pattern resolving power [nm] | LER [nm] |
|---|---|---|---|---|---|---|
| Example 3 | R-3 | 20.3 | 20 | Rectangular | 25 | 4.5 |
| Example 4 | R-4 | 20.2 | 20 | Rectangular | 25 | 4.6 |
| Example 5 | R-5 | 20.6 | 20 | Slightly taper | 27.5 | 4.9 |
| Example 6 | R-6 | 20.1 | 20 | Rectangular | 25 | 4.0 |
| Example 7 | R-7 | 20.4 | 20 | Rectangular | 25 | 4.5 |
| Example 8 | R-8 | 20.3 | 20 | Rectangular | 25 | 4.1 |
| Example 9 | R-9 | 20.5 | 20 | Rectangular | 25 | 4.6 |
| Example 10 | R-10 | 20.7 | 20 | Rectangular | 25 | 4.5 |
| Example 11 | R-11 | 20.4 | 20 | Rectangular | 25 | 4.6 |
| Example 12 | R-12 | 20.2 | 22.5 | Rectangular | 27.5 | 4.7 |
| Example 13 | R-13 | 20.9 | 20 | Rectangular | 25 | 4.7 |
| Comparative Example 1 | R-14 | 22.1 | 30 | Taper | 35 | 5.5 |

From the results shown in the above table, it was found that the composition according to the present invention was excellent in sensitivity, resolving power, a pattern shape, and LER performance, when EB exposure was performed.

<EUV Exposure; Negative-Type; and Alkali Development>

[Preparation of Resist Coating Solution]

The same resist solution as the resist solution used in the above-described EB exposure was prepared.

[Manufacture of Resist Film]

This resist coating solution was applied to the 6-inch wafer on which chrome oxide had been deposited using a spin coater Mark 8 manufactured by Tokyo Electron Limited, and dried on a hot plate at 110° C. for 90 seconds, whereby a resist film having a thickness of 50 nm was obtained. That is, a resist-coated mask blank was obtained.

[Manufacture of Negative-Type Resist Pattern]

Using EUV light (wavelength of 13 nm), exposure was performed on this resist film through a reflective mask of a line and space pattern in a ratio of 1:1 having a line width of 50 nm, followed by baking at 110° C. for 90 seconds. Thereafter, development was performed using a 2.38% by mass tetramethylammonium hydroxide (TMAH) solution.

[Evaluation of Resist Pattern]

Evaluations of the sensitivity, the resolving power, the pattern shape, and the line edge roughness (LER) were performed on the obtained resist pattern by the following methods.

[Sensitivity]

The sectional shape of the obtained pattern was observed by using a scanning electron microscope (S-4300 manufactured by Hitachi, Ltd.). The exposure amount when the resist pattern of the line and space in a ratio of 1:1 having a line width of 50 nm was resolved was taken as sensitivity. A smaller value indicates higher sensitivity.

[L/S Resolving Power]

The sectional shape of the obtained pattern was observed by using a scanning electron microscope (S-4300 manufactured by Hitachi, Ltd.). The marginal resolving power (a minimum line width at which a line and a space (line:space=1:1) are separately resolved) at the exposure amount when resolving a resist pattern of a line and space in a ratio of 1:1 having a line width of 50 nm was taken as a resolving power (nm).

[Pattern Shape]

A sectional shape of the line and space pattern in a ratio of 1:1 having a line width of 50 nm at the exposure amount at which the above sensitivity was exhibited was observed using a scanning electron microscope (S-4300 manufactured by Hitachi, Ltd.). In the sectional shape of the line pattern, a case where the ratio represented by [line width at the top portion (surface portion) of a line pattern/line width at the center portion (height position at half the height of a line pattern) of a line pattern] was less than 0.85 was evaluated as "taper", a case where the ratio was less than 0.95 and 0.85 or greater was evaluated as "slight taper", and a case where the ratio was 0.95 or greater and 1.05 or less was evaluated as "rectangle".

[Line Edge Roughness (LER)]

At the exposure amount at which the above sensitivity was exhibited, a line and space pattern in a ratio of 1:1 having a line width of 50 nm was formed. For arbitrary 30 points included in the longitudinal direction of 50 pin, a distance from a base line where the edge was supposed to be present was measured using a scanning electron microscope (S-9220 manufactured by Hitachi, Ltd.). The standard deviation of the distance was determined, and 3σ was calculated. A smaller value indicates a better performance.

TABLE 3

EUV/alkali development/negative

| Examples | Resist composition | Sensitivity ($mJ/cm^2$) | LS resolving power [nm] | Pattern shape | LER [nm] |
|---|---|---|---|---|---|
| Example 14 | R-1 | 15.9 | 20 | Rectangular | 4.1 |
| Example 15 | R-2 | 15.7 | 20 | Rectangular | 4.1 |
| Example 16 | R-3 | 15.9 | 21 | Rectangular | 4.4 |
| Example 17 | R-4 | 15.7 | 21 | Rectangular | 4.3 |
| Example 18 | R-5 | 15.8 | 24 | Slightly taper | 4.9 |
| Example 19 | R-6 | 15.6 | 20 | Rectangular | 4 |
| Example 20 | R-7 | 16.1 | 18 | Rectangular | 4.5 |
| Example 21 | R-8 | 15.5 | 19 | Rectangular | 4.1 |
| Example 22 | R-9 | 15.7 | 20 | Rectangular | 4.2 |
| Example 23 | R-10 | 15.8 | 21 | Rectangular | 4.1 |
| Example 24 | R-11 | 15.8 | 21 | Rectangular | 4.3 |
| Example 25 | R-12 | 15.6 | 23 | Rectangular | 4.6 |
| Example 26 | R-13 | 15.7 | 21 | Rectangular | 4.1 |
| Comparative Example 2 | R-14 | 16.3 | 31 | Taper | 5.3 |

From the results shown in the above table, it was found that the composition according to the present invention was excellent in sensitivity, resolving power, a pattern shape, and LER performance, when EUV exposure was performed.

<EUV Exposure; Negative-Type; and Organic Solvent Development>

[Preparation of Resist Coating Solution]

The same resist solution as the resist solution used in the above-described EB and EUV exposure was prepared.

[Manufacture of Resist Film]

This resist composition was applied to a 6-inch Si wafer subjected to a hexamethyldisilazane (HMDS) treatment in advance using a spin coater Mark 8 manufactured by Tokyo Electron Limited, and dried on a hot plate at 100° C. for 60 seconds, whereby a resist film having a thickness of 50 nm was obtained.

[Manufacture of Negative-Type Resist Pattern]

Using EUV light (wavelength of 13 nm), exposure was performed on the obtained resist film through a reflective mask of a line and space pattern in a ratio of 1:1 having a line width of 50 nm, followed by baking at 110° C. for 90 seconds, then, the resultant product was developed by paddling the organic-based developer described in the table for 30 seconds, and rinsed by using the rinse liquid described in the same table. The wafer was rotated for 30 seconds at a rotation speed of 4000 rpm, and heated at 90° C. for 60 seconds, whereby a resist pattern of a line and space pattern in a ratio of 1:1 having a line width of 50 nm was obtained.

[Evaluation of Resist Pattern]

Evaluations of the sensitivity, the resolving power, the pattern shape, and the line edge roughness (LER) were performed on the obtained resist pattern by the same methods as those in the case of EUV exposure described above. The results thereof are shown below.

TABLE 4

| | | | | | LS resolving | | |
| Examples | Resist composition | Developer | Rinse liquid | Sensitivity (mJ/cm$^2$) | power [nm] | Pattern shape | LER [nm] |
| --- | --- | --- | --- | --- | --- | --- | --- |
| Example 27 | R-1 | S-8 | S-12 | 15.9 | 21 | Rectangular | 4.1 |
| Example 28 | R-2 | S-9 | S-8 | 15.6 | 20 | Rectangular | 4.2 |
| Example 29 | R-3 | S-8 | S-12 | 15.8 | 22 | Rectangular | 4.4 |
| Example 30 | R-4 | S-9 | S-8 | 15.6 | 21 | Rectangular | 4.3 |
| Example 31 | R-5 | S-10 | S-12 | 15.8 | 23 | Slightly taper | 4.7 |
| Example 32 | R-6 | S-11 | S-9 | 15.5 | 20 | Rectangular | 4.4 |
| Example 33 | R-7 | S-9 | S-12 | 15.9 | 18 | Rectangular | 4.3 |
| Example 34 | R-8 | S-8 | S-12 | 15.4 | 19 | Rectangular | 4.3 |
| Example 35 | R-9 | S-8 | S-12 | 15.6 | 20 | Rectangular | 4.2 |
| Example 36 | R-10 | S-9 | S-12 | 15.8 | 21 | Rectangular | 4.3 |
| Example 37 | R-11 | S-11 | S-9 | 15.7 | 22 | Rectangular | 4.3 |
| Example 38 | R-12 | S-11 | S-12 | 15.6 | 20 | Rectangular | 4.4 |
| Example 39 | R-13 | S-8 | S-12 | 15.9 | 21 | Rectangular | 4.1 |
| Comparative Example 3 | R-14 | S-8 | S-12 | 16.2 | 30 | Taper | 5.5 |

The abbreviations of components which were used but not described in the above examples and comparative examples are listed below.

[Developer and Rinse Liquid]

S-8: butyl acetate

S-9: isobutyl acetate

S-10: anisole

S-11: 2-heptanone

S-12: methylisobutylcarbinol

From the results shown in the above table, it was found that the composition according to the present invention was excellent in sensitivity, resolving power, a pattern shape, and LER performance, when EUV exposure was performed.

What is claimed is:

1. An active light sensitive or radiation sensitive resin composition, comprising:
   (A) an alkali soluble resin;
   (B) a compound that generates an acid by irradiation with active light or radiation; and
   (C) at least one cross-linking agent selected from the group of compounds represented by the following General Formula (1-0) or General Formula (1-1),

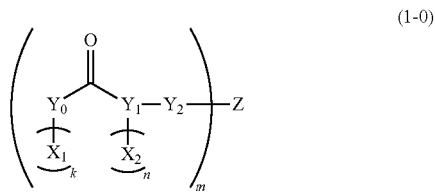

(1-0)

wherein, in the General Formula (1-0), each of $X_1$ and $X_2$ independently represents a hydrogen atom, an alkyl group, a hydroxymethyl group, or an alkoxymethyl group, each of $Y_0$ and $Y_1$ independently represents a carbon atom, a nitrogen atom, or an oxygen atom, at least one of k $X_1$'s and n $X_2$'s is a hydroxymethyl group or an alkoxymethyl group, and at least one of $Y_0$ and $Y_1$ is a nitrogen atom substituted with the hydroxymethyl group or the alkoxymethyl group, $Y_2$ represents a single bond or an alkylene group, Z represents an m valent connecting group, k is 3 when $Y_0$ is a carbon atom, is 2 when $Y_0$ is a nitrogen atom, and is 1 when $Y_0$ is an oxygen atom, n is 2 when $Y_1$ is a carbon atom, is 1 when $Y_1$ is a nitrogen atom, and is 0 when $Y_1$ is an oxygen atom, m represents an integer of 2 to 6, and two of $X_1$, $X_2$, and $Y_2$ may be bonded to each other to form a ring, provided that, in a case where $X_1$ and $Y_2$ are bonded to each other to form a ring, Z is a connecting group selected from the group consisting of a linear or branched alkylene group, a cycloalkylene group an arylene group, an ether bond, a thioether bond, an amide bond, a urethane bond, a urea bond, and a group obtained by combining two or more thereof

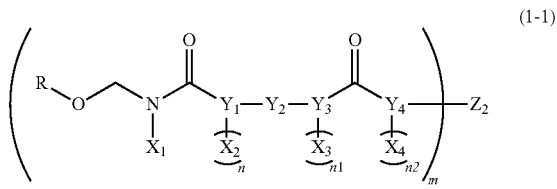

(1-1)

wherein, in the General Formula (1-1),

R represents a hydrogen atom or an alkyl group, each of $X_1$ and $X_2$ independently represents a hydrogen atom, an alkyl group, a hydroxymethyl group, or an alkoxymethyl group, at least one of $X_1$ and n $X_2$'s is a hydroxymethyl group or an alkoxymethyl group, and at least one of a nitrogen atom substituted with $X_1$ and $Y_1$ is a nitrogen atom substituted with the hydroxymethyl group or the alkoxymethyl group, $Y_1$ represents a carbon atom, a nitrogen atom, or an oxygen atom, $Y_2$ represents a single bond or an alkylene group, each of $Y_3$ and $Y_4$ independently represents a single bond, a carbon atom, a nitrogen atom, or an oxygen atom, each of $X_3$ and $X_4$ independently represents a hydrogen atom or an alkyl group, $Z_2$ represents a chain or cyclic saturated hydrocarbon group, an aromatic hydrocarbon group, or a group obtained by combining two or more thereof, n is 2 when $Y_1$ is a carbon atom, is 1 when $Y_1$ is a nitrogen atom, and is 0 when $Y_1$ is an oxygen atom, n1 is 0 when $Y_3$ is a single bond or an oxygen atom, is 1 when $Y_3$ is a nitrogen atom, and is 2 when $Y_3$ is a carbon atom, n2 is 0 when $Y_4$ is a single bond or an oxygen atom, is 1 when $Y_4$ is a nitrogen atom, and is 2 when $Y_4$ is a carbon atom, m represents an integer of 2 to 6, and two of $X_1$, $X_2$, and $Y_2$ may be bonded to each other to form a ring, provided that, in a case where $X_1$ and $Y_2$ are bonded to each other to form a ring, $Z_2$ represents a chain or cyclic saturated hydrocarbon group, or an aromatic hydrocarbon group, and wherein the molecular weight of the cross-linking agent (C) is 450 to 1500.

2. The active light sensitive or radiation sensitive resin composition according to claim 1, wherein the cross-linking agent (C) is represented by the following General Formula (1),

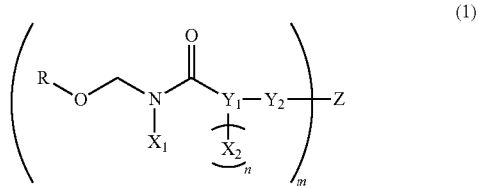

(1)

wherein, in the formula,

R represents a hydrogen atom or an alkyl group, each of $X_1$ and $X_2$ independently represents a hydrogen atom, an alkyl group, a hydroxymethyl group, or an alkoxymethyl group, $Y_1$ represents a carbon atom, a nitrogen atom, or an oxygen atom, $Y_2$ represents a single bond or an alkylene group, Z represents an m valent connecting group, n is 2 when $Y_1$ is a carbon atom, is 1 when $Y_1$ is a nitrogen atom, and is 0 when $Y_1$ is an oxygen atom, m represents an integer of 2 to 6, and two of $X_1$, $X_2$, and $Y_2$ may be bonded to each other to form a ring, provided that, in a case where $X_1$ and $Y_2$ are bonded to each other to form a ring, Z is a connecting group selected from the group consisting of a linear or branched alkylene group, a cycloalkylene group, an arylene group, an ether bond, a thioether bond, an amide bond, a urethane bond, a urea bond, and a group obtained by combining two or more thereof.

3. The active light sensitive or radiation sensitive resin composition according to claim 2, wherein, in General Formula (1), Z is represented by the following General Formula (2), and

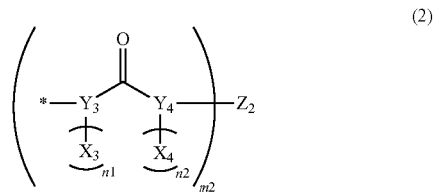

(2)

wherein, in the formula, each of $Y_3$ and $Y_4$ independently represents a single bond, a carbon atom, a nitrogen atom, or an oxygen atom, each of $X_3$ and $X_4$ independently represents a hydrogen atom or an alkyl group, when $Y_3$ and $Y_4$ are single bonds or oxygen atoms, each of n1 and n2 is 0, when $Y_3$ and $Y_4$ are nitrogen atoms, each of n1 and n2 is 1, and when $Y_3$ and $Y_4$ are carbon atoms, each of n1 and n2 is 2, $Z_2$ represents a chain or cyclic saturated hydrocarbon group, an aromatic hydrocarbon group, or a group obtained by combining two or more thereof, m2 represents an integer of 2 to 6, and corresponds to m in General Formula (1), and

* represents a linking site with $Y_2$ in General Formula (1).

4. The active light sensitive or radiation sensitive resin composition according to claim 3, wherein, in General Formula (2), m2 is 2 or 3.

5. The active light sensitive or radiation sensitive resin composition according to claim 3, wherein, in General Formula (2), $Z_2$ represents a cyclic saturated hydrocarbon group, an aromatic hydrocarbon group, or a combination of a cyclic saturated hydrocarbon group and an aromatic hydrocarbon group.

6. The active light sensitive or radiation sensitive resin composition according to claim 2, wherein, in General Formula (1), m is 2 or 3.

7. The active light sensitive or radiation sensitive resin composition according to claim 1,
wherein the compound (B) that generates an acid by irradiation with active light or radiation is a sulfonium salt.

8. An active light sensitive or radiation sensitive film which is formed of the active light sensitive or radiation sensitive resin composition according to claim 1.

9. A mask blank provided with the active light sensitive or radiation sensitive film according to claim 8.

10. A pattern forming method, comprising:
a step of forming a film by applying the active light sensitive or radiation sensitive resin composition claim 1 to a substrate;
a step of exposing the film; and
a step of forming a negative-type pattern by developing the exposed film.

11. A method for manufacturing an electronic device, comprising:
the pattern forming method according to claim 10.

12. The active light sensitive or radiation sensitive resin composition according to claim 1,
wherein the compound (B) is a compound that generates an acid having a volume of 130 Å$^3$ or greater.

13. The active light sensitive or radiation sensitive resin composition according to claim 1,
wherein the content of the compound (B) is 0.1% by mass to 35% by mass based on the total solid content of the composition.

14. The active light sensitive or radiation sensitive resin composition according to claim 1,
wherein the content of the cross-linking agent (C) is 3% by mass to 65% by mass based on the solid content of the composition.

15. The active light sensitive or radiation sensitive resin composition according to claim 1,
wherein the at least one cross-linking agent (C) is selected from the group of compounds consisting of:

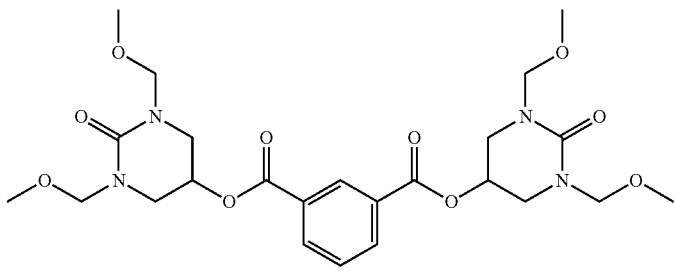

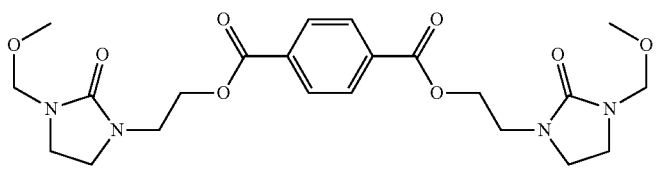

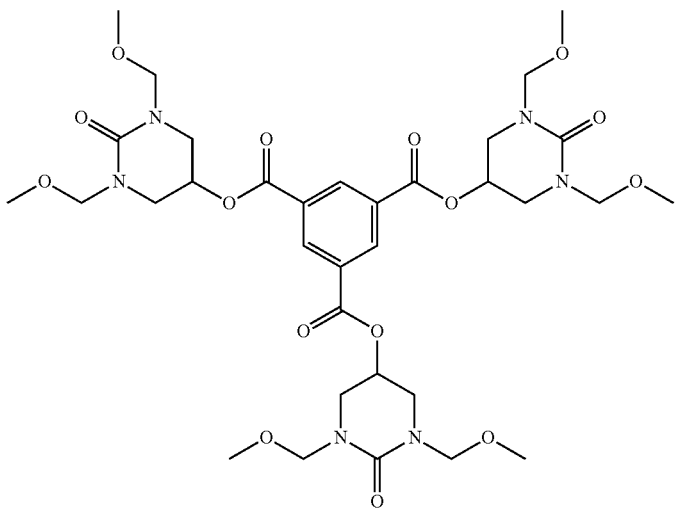

-continued
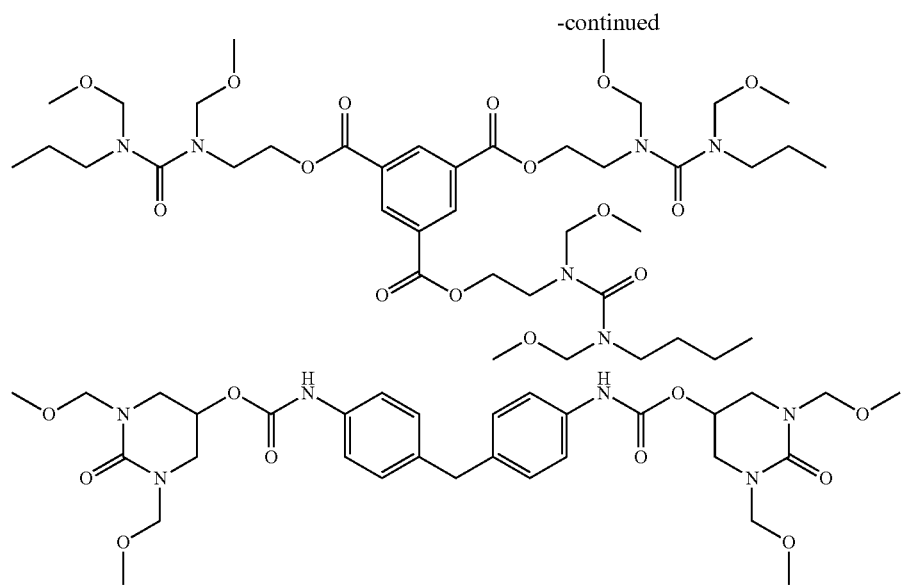
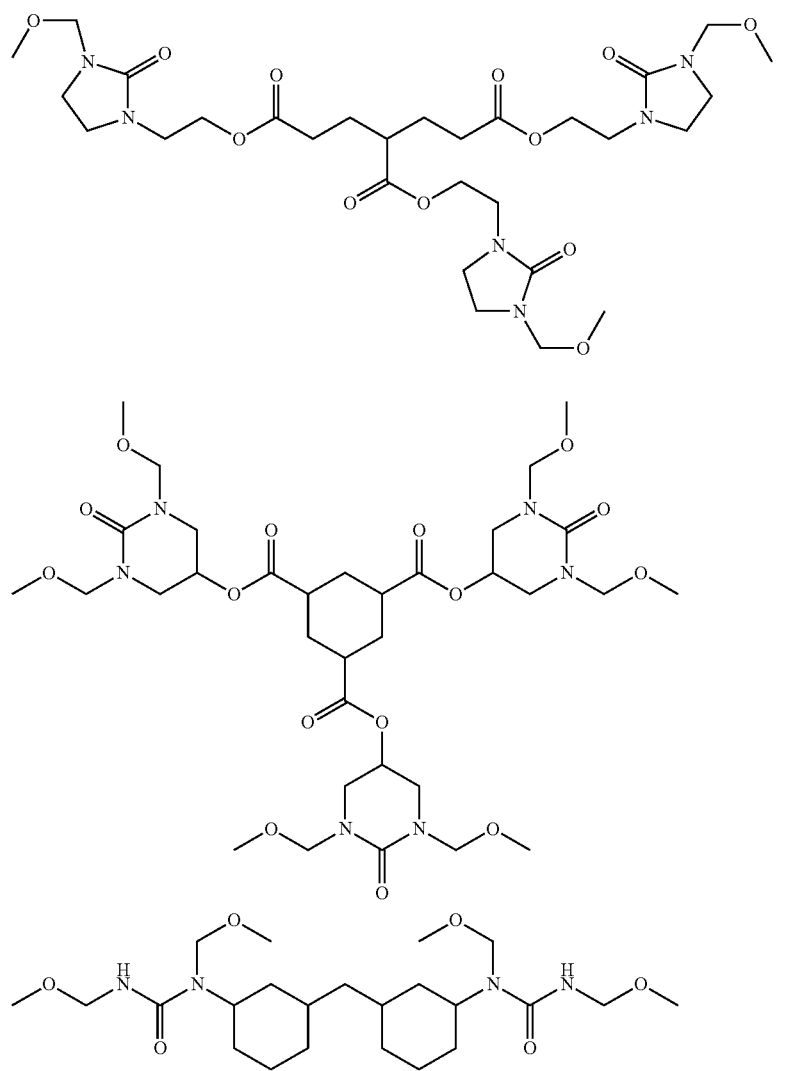

163
-continued
164
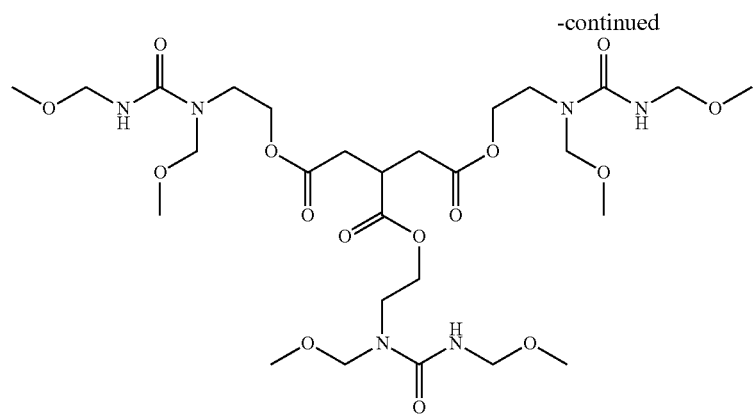
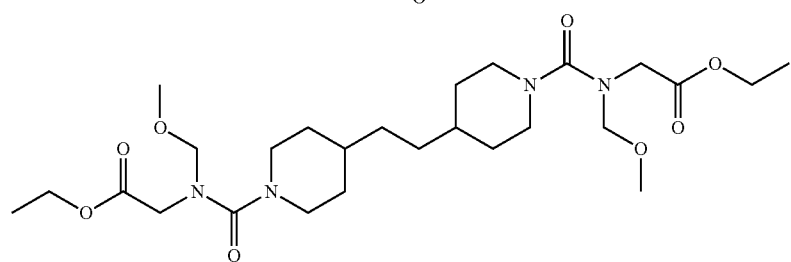
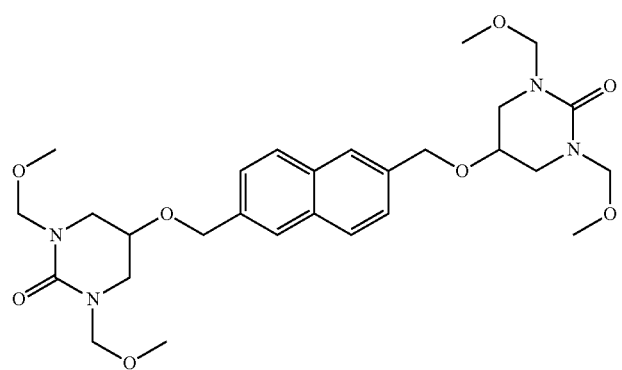
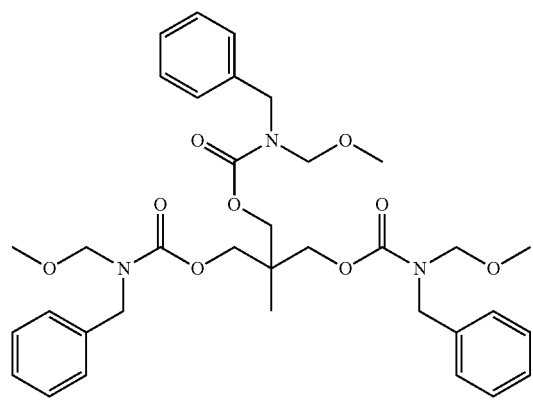
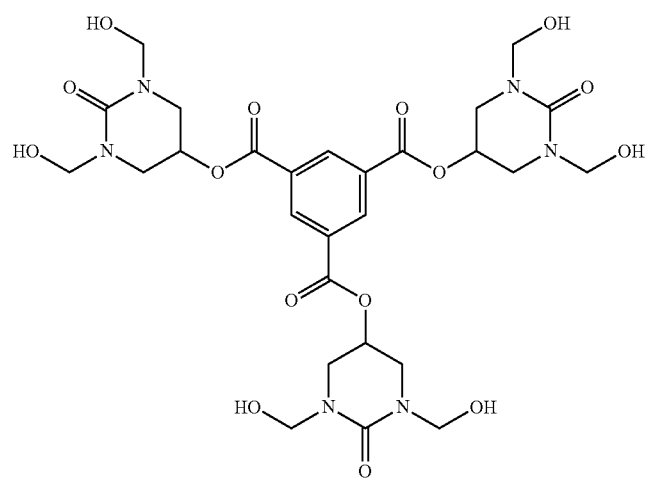

-continued

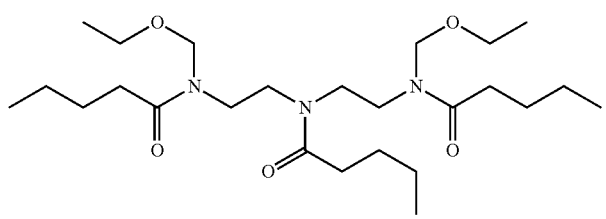
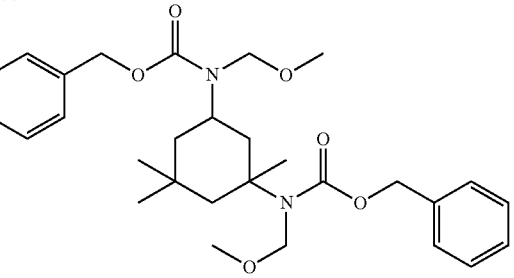

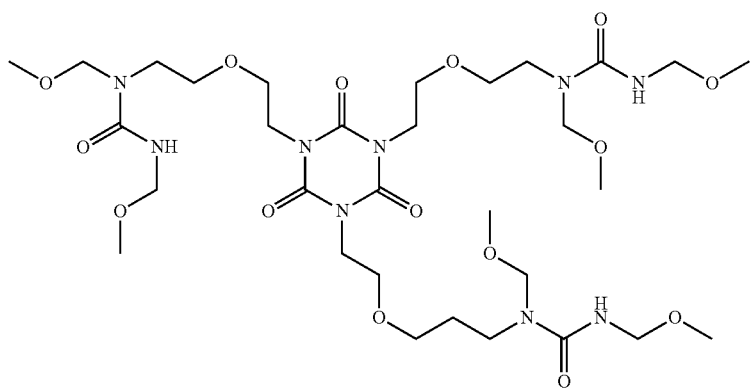

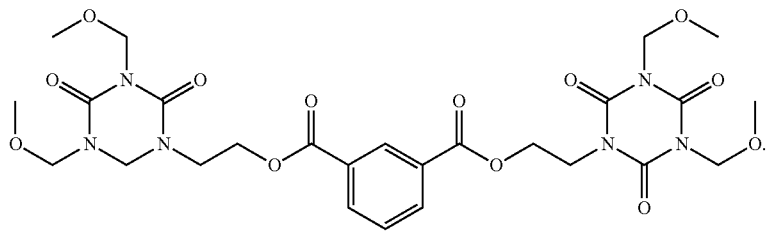

16. The active light sensitive or radiation sensitive resin composition according to claim 1,
   wherein, in General Formula (1-0) or General Formula (1-1), m is 2 or 3.

17. The active light sensitive or radiation sensitive resin composition according to claim 1,
   wherein, in General Formula (1-0), $Y_0$ represents a carbon atom, a nitrogen atom, or an oxygen atom, and $Y_1$ represents a nitrogen atom, or an oxygen atom.

18. The active light sensitive or radiation sensitive resin composition according to claim 1,
   wherein the compound that generates an acid by irradiation with active light or radiation (B) is represented by the following General Formula (7),

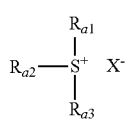

(7)

wherein each of $R_{a1}$, $R_{a2}$, and $R_{a3}$ independently represents an organic group, and
   $X^-$ represents an organic anion.

19. The active light sensitive or radiation sensitive resin composition according to claim 18,
   wherein at least one of $R_{a1}$, $R_{a2}$, and $R_{a3}$ is an aryl group.

20. The active light sensitive or radiation sensitive resin composition according to claim 19,
   wherein the aryl group is selected from the group consisting of a phenyl group, and a naphthyl group.

21. The active light sensitive or radiation sensitive resin composition according to claim 18,
   wherein, in General Formula (7), the organic anion $X^-$ is selected from the group consisting of a sulfonate anion, a carboxylate anion, a bis(alkylsulfonyl)amide anion, and a tris(alkylsulfonyl)methide anion.

22. An active light sensitive or radiation sensitive resin composition, comprising:
   (A) an alkali soluble resin; and
   (B) a compound that generates an acid by irradiation with active light or radiation;
   (C) at least one cross-linking agent selected from the group of compounds consisting of:

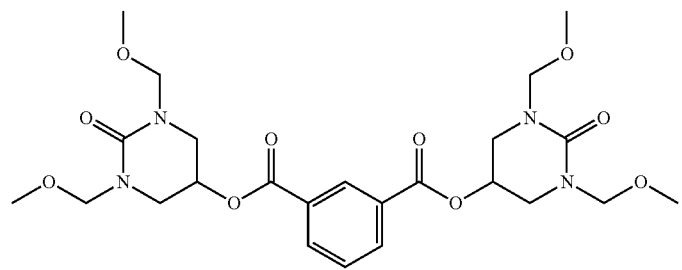
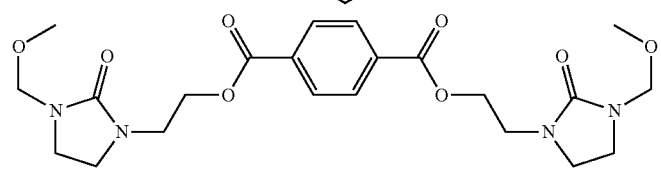
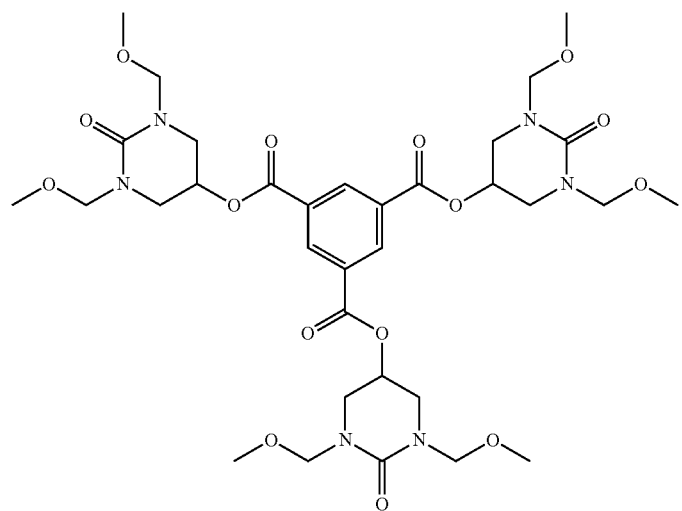
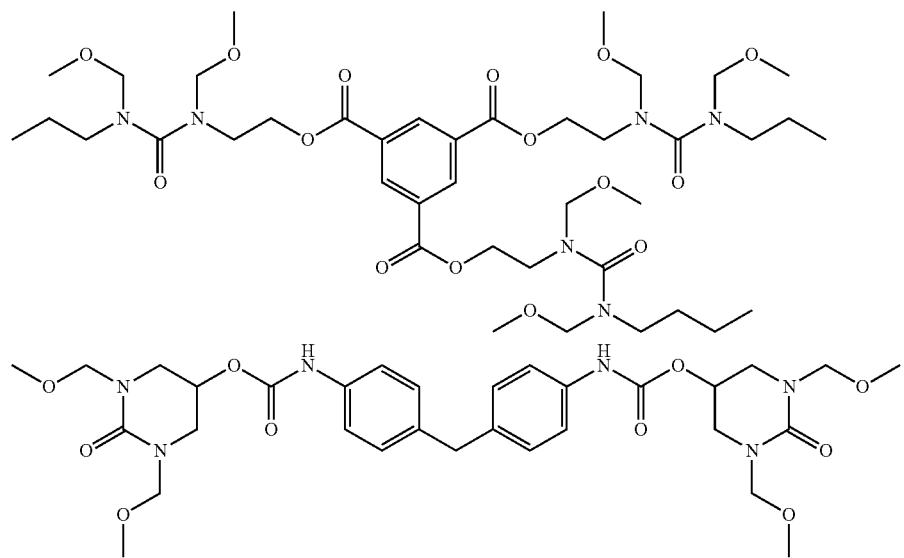

-continued
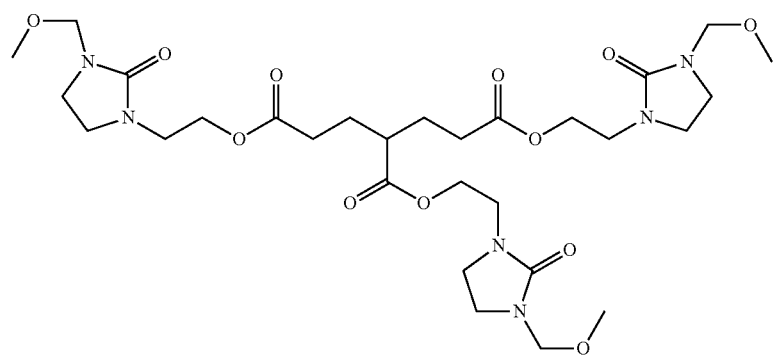
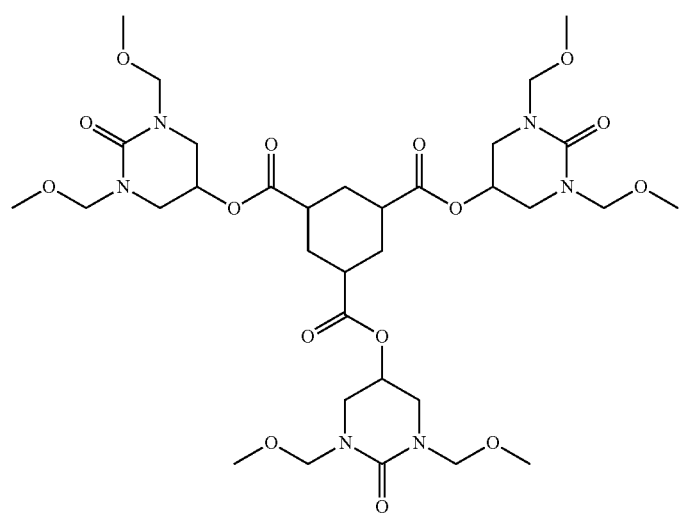
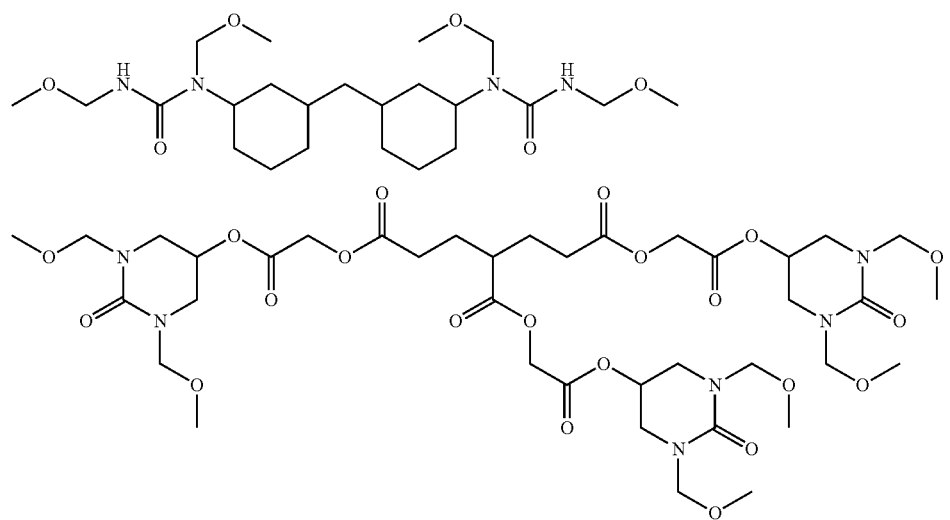

-continued
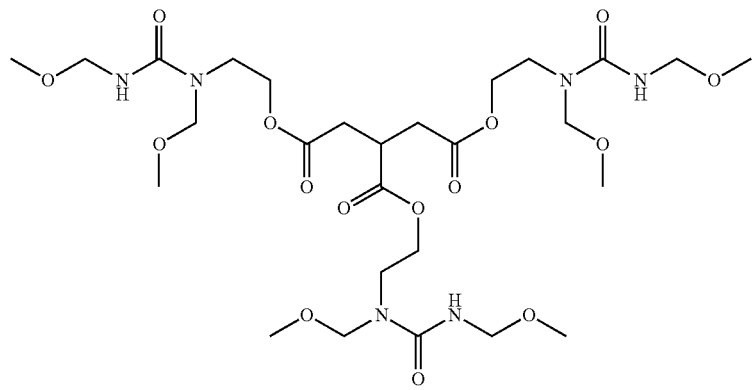
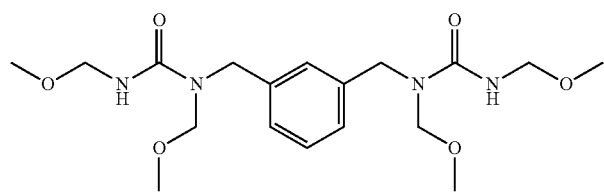
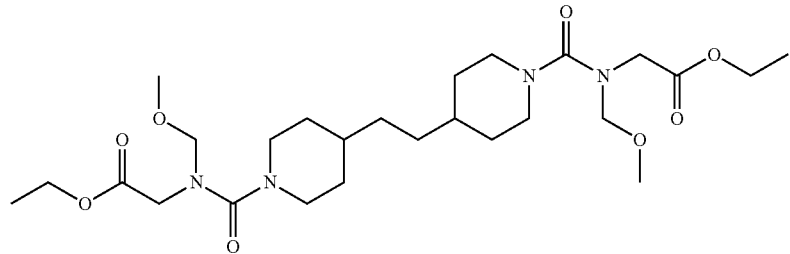
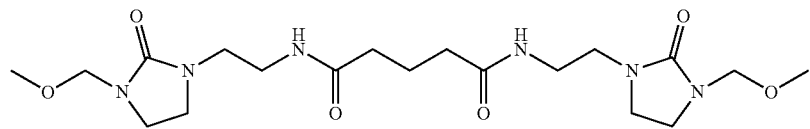
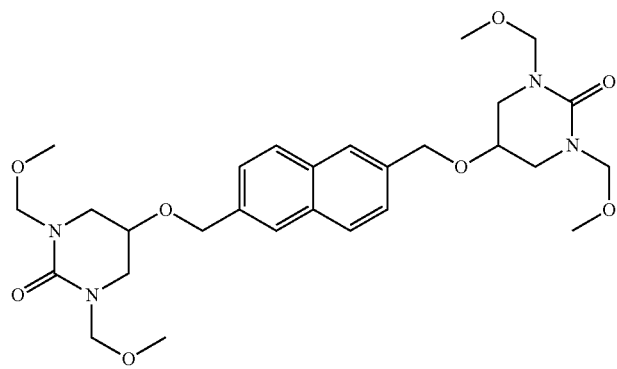
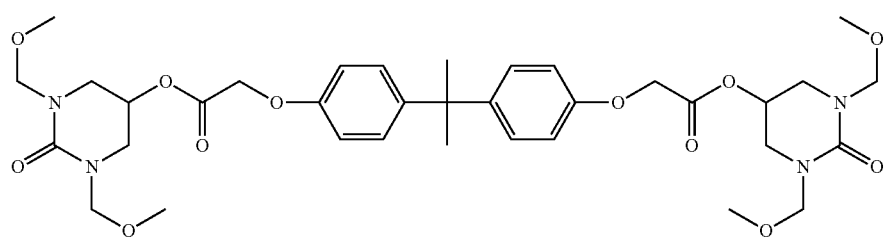

-continued
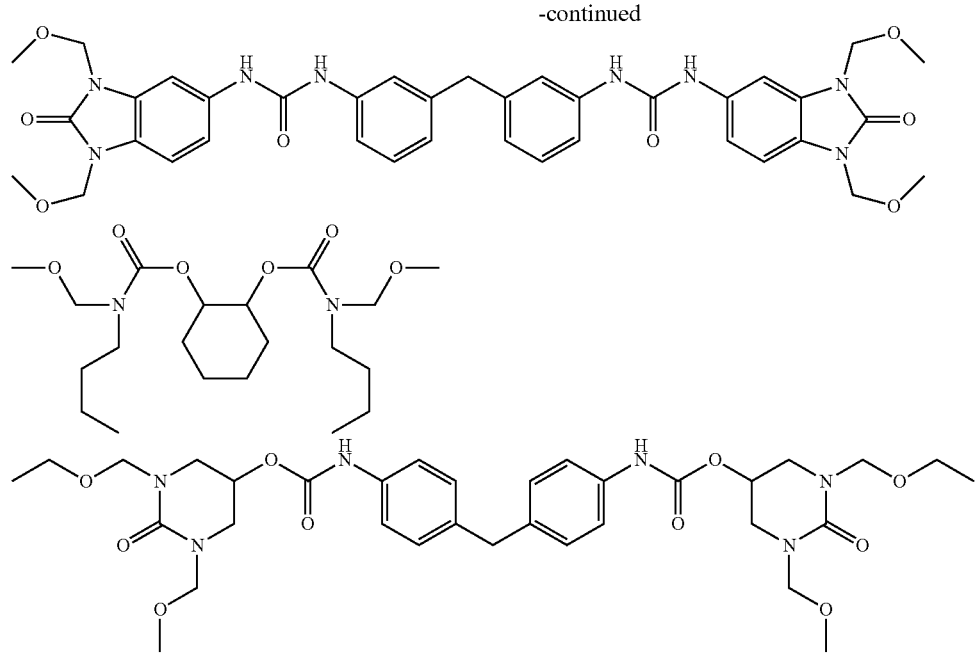
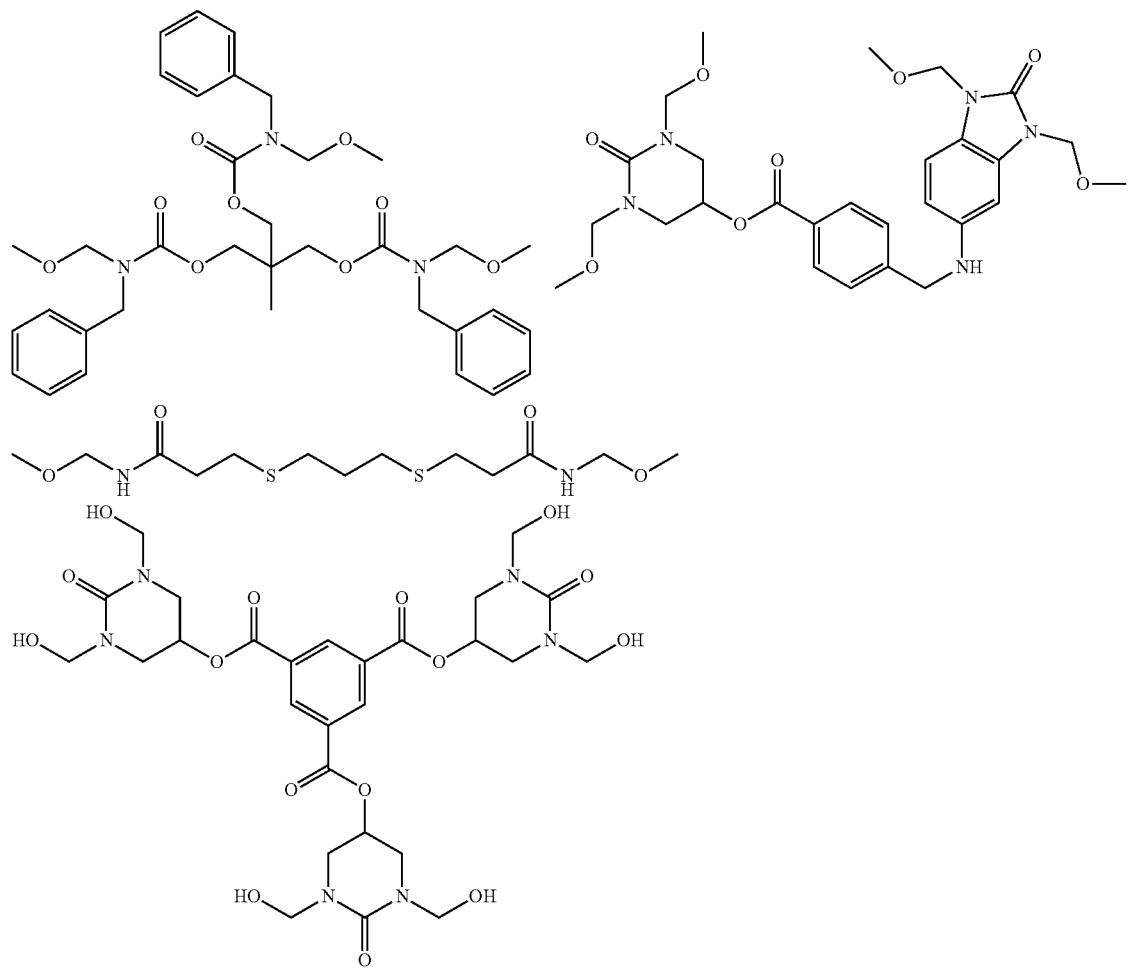

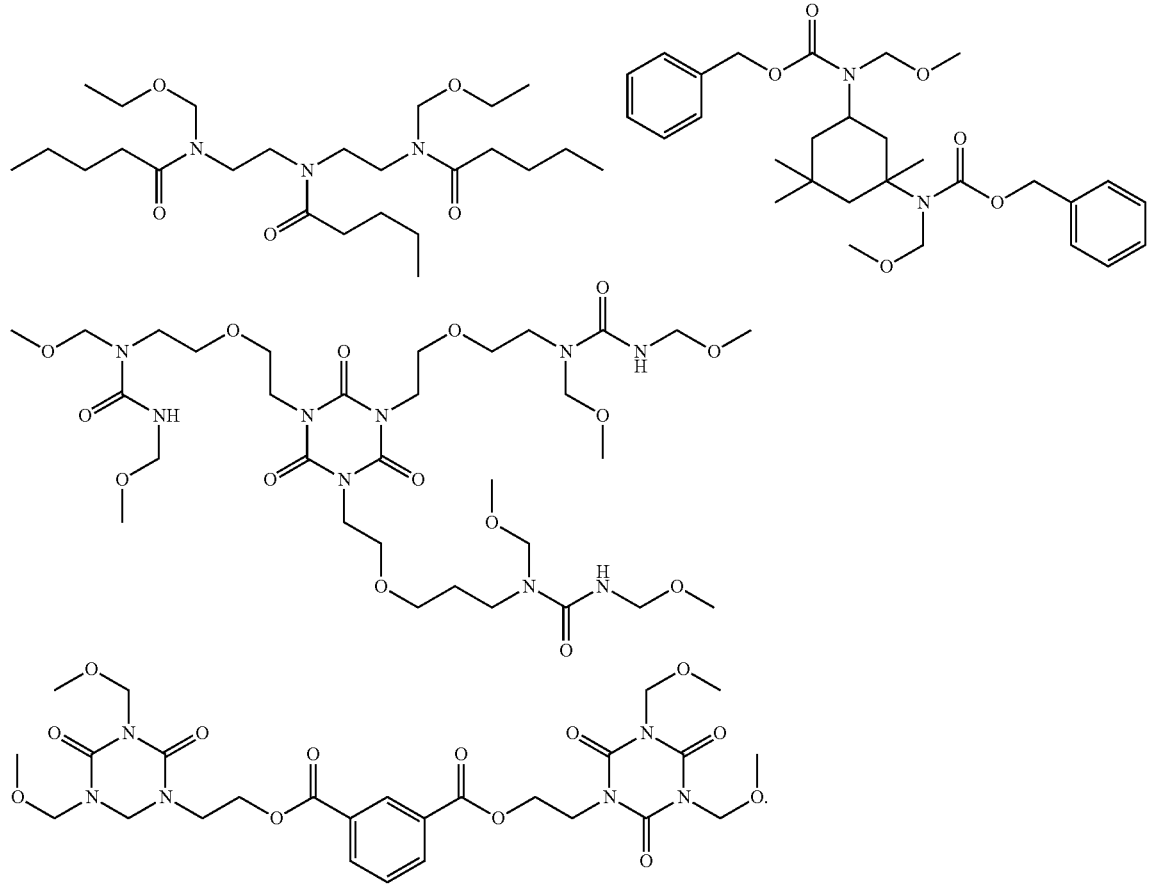
* * * * *